(12) United States Patent
Miller et al.

(10) Patent No.: US 9,583,803 B2
(45) Date of Patent: Feb. 28, 2017

(54) SHIELDING RECEPTABLE FOR BATTERY CELLS

(71) Applicant: Enovate Medical, LLC, Murfreesboro, TN (US)

(72) Inventors: David R. Miller, Murfreesboro, TN (US); Allen Kilbourne, Canton, MI (US); Gordon Waid, Murfreesboro, TN (US); Kou Yang, Canton, MI (US); Michael Mason, Canton, MI (US); Joseph Moody, American Fork, UT (US)

(73) Assignee: Enovate Medical LLC, Murfreesboro, TN (US)

( * ) Notice: Subject to any disclaimer, the term of this patent is extended or adjusted under 35 U.S.C. 154(b) by 223 days.

(21) Appl. No.: 14/323,589

(22) Filed: Jul. 3, 2014

(65) Prior Publication Data

US 2015/0364799 A1 Dec. 17, 2015

Related U.S. Application Data

(60) Provisional application No. 62/010,921, filed on Jun. 11, 2014.

(51) Int. Cl.
| | | |
|---|---|---|
| *H02J 7/00* | (2006.01) | |
| *H02J 7/04* | (2006.01) | |
| *H01M 10/659* | (2014.01) | |
| *H02J 5/00* | (2016.01) | |
| *H02J 7/02* | (2016.01) | |
| *H01M 10/658* | (2014.01) | |
| *H01M 2/10* | (2006.01) | |
| *H01M 2/12* | (2006.01) | |

(Continued)

(52) U.S. Cl.
CPC ....... *H01M 10/659* (2015.04); *H01M 2/1022* (2013.01); *H01M 2/1264* (2013.01); *H01M 2/348* (2013.01); *H01M 10/46* (2013.01); *H01M 10/482* (2013.01); *H01M 10/486* (2013.01); *H01M 10/658* (2015.04); *H02J 5/005* (2013.01); *H02J 7/007* (2013.01); *H02J 7/0021* (2013.01); *H02J 7/0047* (2013.01); *H02J 7/025* (2013.01); *H02J 17/00* (2013.01); *H04B 5/0037* (2013.01); *H04Q 9/00* (2013.01); *G01V 3/12* (2013.01); *H01M 2200/10* (2013.01); *H01M 2200/103* (2013.01); *H01M 2220/30* (2013.01); *Y10T 307/469* (2015.04)

(58) Field of Classification Search
USPC ....... 320/134, 108, 107, 101, 112, 128, 120; 307/66; 429/120, 163, 144, 156, 99, 82, 429/100, 146, 145, 149
See application file for complete search history.

(56) References Cited

U.S. PATENT DOCUMENTS

| | | | |
|---|---|---|---|
| 2003/0096160 A1* | 5/2003 | Sugiura | ............... H01M 2/1022 429/120 |
| 2003/0193315 A1* | 10/2003 | Madjar | .................. H01M 6/44 320/112 |

(Continued)

*Primary Examiner* — Alexis A Boateng
(74) *Attorney, Agent, or Firm* — Waller Lansden Dortch & Davis LLP; Nathan J. Bailey; Blake M. Bernard

(57) ABSTRACT

A thermally shielded receptacle for a rechargeable battery. The thermally shielded receptacle can include a material having a heat deflection rate of greater than 50 degrees Celsius to contain a catastrophic runaway of one or more of a plurality of individual battery cells. The thermally shielded receptacle can include material sized and shaped to receive the plurality of individual battery cells and separate each of the plurality of individual battery cells from adjacent individual battery cells.

17 Claims, 37 Drawing Sheets

(51) Int. Cl.
*H01M 2/34* (2006.01)
*H01M 10/48* (2006.01)
*H04B 5/00* (2006.01)
*H02J 17/00* (2006.01)
*H04Q 9/00* (2006.01)
*H01M 10/46* (2006.01)
*G01V 3/12* (2006.01)

(56) References Cited

U.S. PATENT DOCUMENTS

| | | | |
|---|---|---|---|
| 2004/0232891 A1* | 11/2004 | Kimoto | H01M 2/1077 320/150 |
| 2006/0164795 A1* | 7/2006 | Jones | H01M 2/1094 361/600 |
| 2009/0208835 A1* | 8/2009 | Horiuchi | H01M 2/0202 429/156 |
| 2010/0136405 A1* | 6/2010 | Johnson | H01M 2/105 429/120 |
| 2011/0195284 A1* | 8/2011 | Yasui | H01M 2/0242 429/82 |
| 2011/0274951 A1* | 11/2011 | Yasui | H01M 2/1016 429/53 |
| 2014/0272517 A1* | 9/2014 | Glasgow | H01M 10/5053 429/120 |
| 2015/0171396 A1* | 6/2015 | Okuno | H01M 2/1686 701/22 |
| 2015/0357684 A1* | 12/2015 | Willgert | H01M 10/46 320/112 |

* cited by examiner

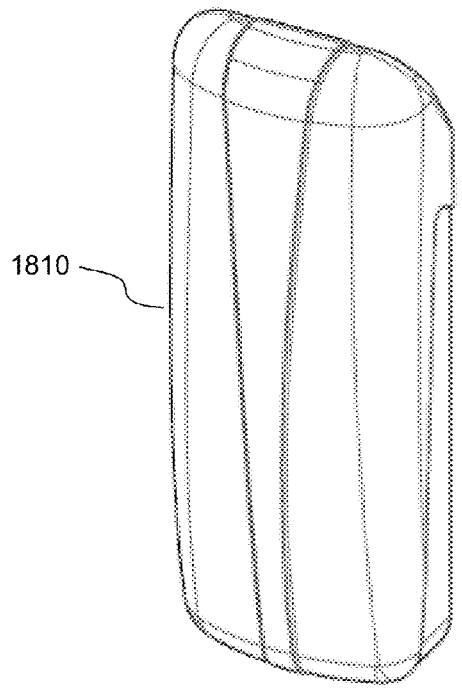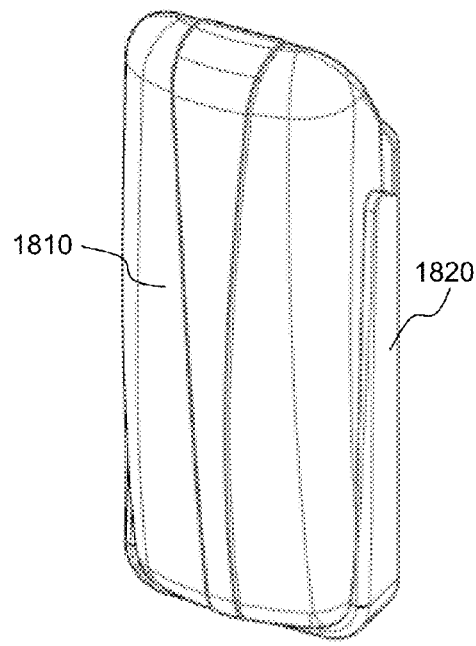
FIG.18b
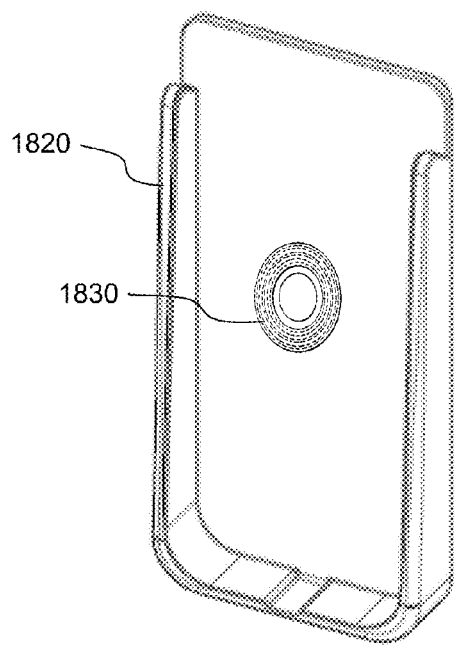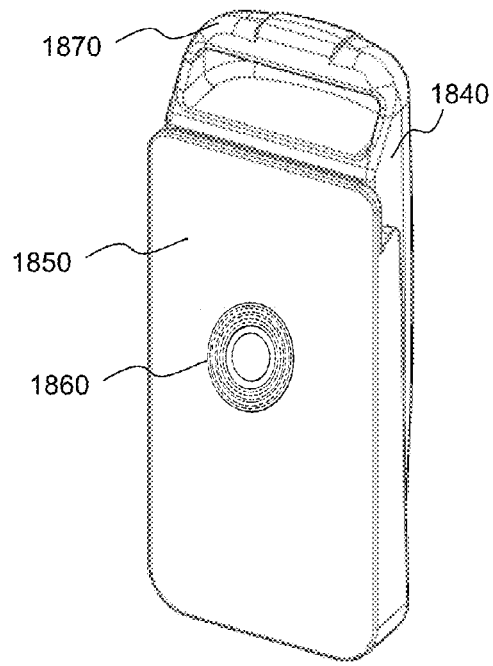
FIG.18a
FIG.18c

SHIELDING RECEPTABLE FOR BATTERY CELLS

This application claims the benefit of U.S. Provisional Application No. 62/010,921, filed Jun. 11, 2014, the entire disclosure of which is incorporated herein by this reference.

BACKGROUND

With an increase of portable equipment, transportation, and communication markets, the battery industry is continually expanding to meet the increasing energy need. Typically, batteries can be broadly classified into two categories: primary batteries and secondary batteries. A primary battery, also known as a disposable battery, can be used once until the battery is depleted, after which the disposable battery can be replaced with a new battery. A secondary battery, also known as a rechargeable battery, can be capable of repeated recharging and reuse. Some advantages of rechargeable batteries are that they can be cost effective, environmentally friendly, and easier to use compared to disposable batteries.

While rechargeable batteries offer a number of advantages over disposable batteries, rechargeable batteries also have several drawbacks. Typically, battery chemistries used for rechargeable batteries tend to be less stable than battery chemistries used in disposable batteries. The relatively unstable chemistries of rechargeable batteries can require special handling during fabrication. Additionally, rechargeable batteries such as lithium-ion cell batteries have a higher risk of thermal runaway compared to cells of disposable batteries. Thermal runaway can occur when an internal reaction rate of a battery cell increases beyond a point that heat generated by the cell can be withdrawn, causing a further increase in both reaction rate and heat generation of the cell. Heat generated by a thermal runaway can lead to combustion of the battery as well as materials adjacent to the battery. Causes of thermal runaway can include: a short circuit within a battery cell, improper cell use, physical abuse of a cell or battery, over charging, internal shorts, manufacturing defects, exposure of the cell to extreme external temperatures, non-functioning safety systems, and so forth.

When a battery experiences a thermal runaway, the battery may emit a large quantity of smoke, flaming liquid electrolyte, and sufficient heat to cause combustion and destruction of materials adjacent to the cell. If a cell experiencing thermal runaway is adjacent to one or more additional cells, as can be typical in a battery pack, then the thermal runaway event can cause a thermal runaway of multiple cells which, in turn, can lead to an increase in collateral damage.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIG. 18a depicts a side perspective view of another wireless transfer station and a receptacle in accordance with an example;

FIG. 18b depicts another side perspective view of a wireless transfer station coupled to a receptacle in accordance with an example;

FIG. 18c depicts a back perspective view of a wireless transfer station coupled to a receptacle in accordance with an example;

Figure 1:
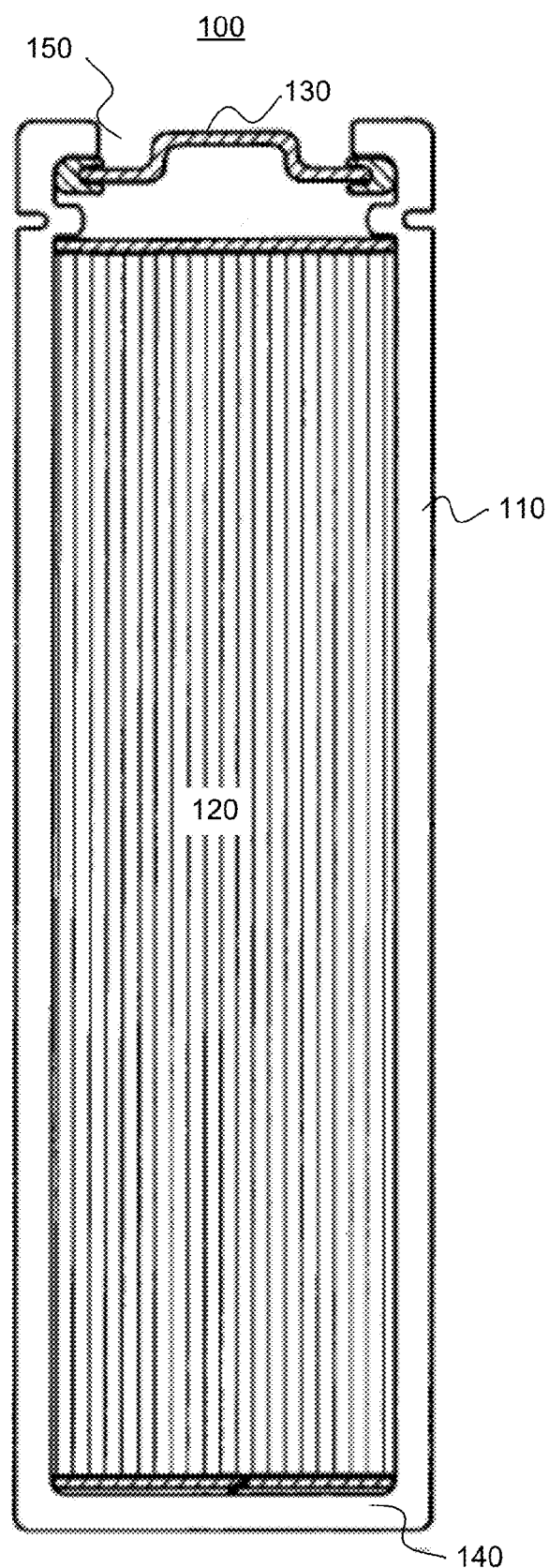
FIG. 1 depicts a cross-sectional view of a battery in accordance with an example.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

The terms battery, cell, and/or battery cell as used herein can be used interchangeably and can refer to any of a variety of different cell chemistries and configurations. In one embodiment the cell chemistries and configurations can include, but are not limited to, lithium ion (e.g., lithium iron phosphate, lithium cobalt oxide, other lithium metal oxides, etc.), lithium ion polymer, nickel metal hydride, nickel cadmium, nickel hydrogen, nickel zinc, silver zinc, or other battery type/configuration.

The term battery pack as used herein can refer to: multiple individual batteries contained within a single piece housing or multi-piece housing and the individual batteries electrically interconnected to achieve a selected energy level and capacity.

Rechargeable batteries are produced in a number of variations. In one example, a rechargeable battery can be a lithium-ion based battery, which has a high energy density and uses a cobalt or nickel-cobalt oxide cathode. One disadvantage of rechargeable batteries can be that the rechargeable batteries can create their own internal supply of oxygen when the rechargeable batteries overheat. More specifically for lithium-ion based batteries, oxygen is liberated from the oxide material of a cathode of a lithium-ion based battery at elevated temperatures. In one example, the elevated temperatures can have a variety of causes, such as an internal short circuit, overcharging, or other causes. Since oxygen and fuel are both internally available to the lithium-ion based battery cells, a fire can start within a single battery cell and can be difficult to extinguish with conventional methods. In some cases the fire can continue until all the flammable materials in a battery pack have been exhausted.

There are several schemes to reduce a probability of a thermal runaway of rechargeable batteries. In one embodiment, a thermal runaway issue can be reduced or eliminated by developing new cell chemistries and/or modifying existing cell chemistries. In one example, to reduce a probability of a thermal runaway of rechargeable batteries, the batteries and/or battery packs can be designed to reduce possible causes of the thermal runaway. In one example, the batteries and/or battery packs can be designed to reduce battery cells from shorting out during storage and/or handling. In another example, batteries or battery cells of a battery pack can be properly stored, such as by insulating the battery terminals and/or designed battery storage containers. Although cell chemistries and cell designs can reduce a probability of a thermal runaway, currently cell chemistries and cell designs can only reduce, not eliminate, a probability of a thermal runaway.

When a cell enters into thermal runaway, the cell and/or battery pack may no longer be viable. In one embodiment, the battery pack can be designed to contain the thermal runaway event of a cell to minimize or eliminate the cell thermal runaway from affecting neighboring cells, potentially causing a cascading event of a thermal runaway of multiple cells.

In one embodiment, the battery pack can include a thermal runaway detector to determine precursor events that increase a probability of a thermal runaway. In another embodiment, the thermal runaway detector can be a temperature-measuring device (such as a thermal couple) attached to each battery cell to detect a thermal runaway of the cell by monitoring an internal temperature of the cell.

FIG. 1 shows a cross-sectional view of a battery 100, for example a lithium ion battery utilizing an 18650 battery form-factor. The battery 100 can include: a case 110, such as a cylindrical case, one or more electrodes 120, and a cap 130. In one embodiment, the case 110 can be made of a metal, such as nickel-plated steel, that can be non-reactive with battery materials, such as an electrolyte or the one or more electrodes 120. In one embodiment, a bottom surface 140 of the case 110 can be seamlessly integrated with the remainder of the case 110. In one embodiment, a top end 150 of the case 110 can be open ended. In another embodiment, the cap 130 can be located at the top end of the case 110. In another embodiment, the top end 150 can be a positive electrical terminal of the battery 100 and the bottom end 140 can be a negative electrical terminal. In one example, the positive electrical terminal and the negative electrical terminal of the battery 100 can be connected to a wireless transfer station to provide energy to the wireless transfer station (as discussed in the proceeding paragraphs). In another embodiment, a plurality of batteries can be connected in series and/or in parallel. In one embodiment, the battery 100 can be connected to a power management module, such as the power management modules in FIGS. 7, 9a, and 9b.

In one embodiment, the wireless transfer station can include one or more wireless transfer coils to transfer energy and/or data with other wireless transfer stations. The wireless transfer coil can include one or more power management modules to control the energy transfers and/or data transfers with the other wireless transfer stations.

Examples of a wireless transfer station includes a wireless energy rechargeable battery pack, a wireless energy transfer platform and/or data transceiver integrated into a medical cart, a wireless energy transfer platform and/or data transceiver integrated into an electronic device, a wireless energy transfer platform and/or data transceiver integrated into a piece of furniture, a wireless energy transfer platform and/or data transceiver integrated into a plate mounted to a wall, a wireless energy transfer platform and/or data transceiver integrated into a device (such as a medical device or medical equipment), and so forth.

In one example, the wireless transfer station can be a wireless energy battery pack that can be attached to a device, such as a medical cart or medical equipment. The wireless transfer station that transfers energy and/or data with the device can also relay the energy and/or data with other devices and/or wireless transfer stations. These examples are not intended to be limiting. The wireless transfer station can be implemented in a variety of electronic devices and mounting locations.

In one embodiment, thermal runaway of a cell in a battery, such as the cell shown in FIG. 1, can be caused a variety of different abusive operating or charging conditions and/or manufacturing defects. Thermal runaway occurs where an amount of heat generated in a cell exceeds an amount of heat that can effectively be withdrawn from the cell. When the heat cannot be effectively withdrawn from the cell, a large amount of thermal energy is rapidly released, heating the entire cell up to a temperature of 900 degrees Celsius or more and causing formations of localized hot spots that can reach temperatures exceeding 1500 degrees Celsius. Associated with the temperature increase of the thermal runaway, gas can also be released causing a pressure within the cell to increase.

Traditionally, when multiple cells are stacked together, it is difficult to remove heat from cells located in the inner part of the multiple cell stack and this configuration can cause localized cycling of the battery, which can lead to premature aging.

Figure 2:
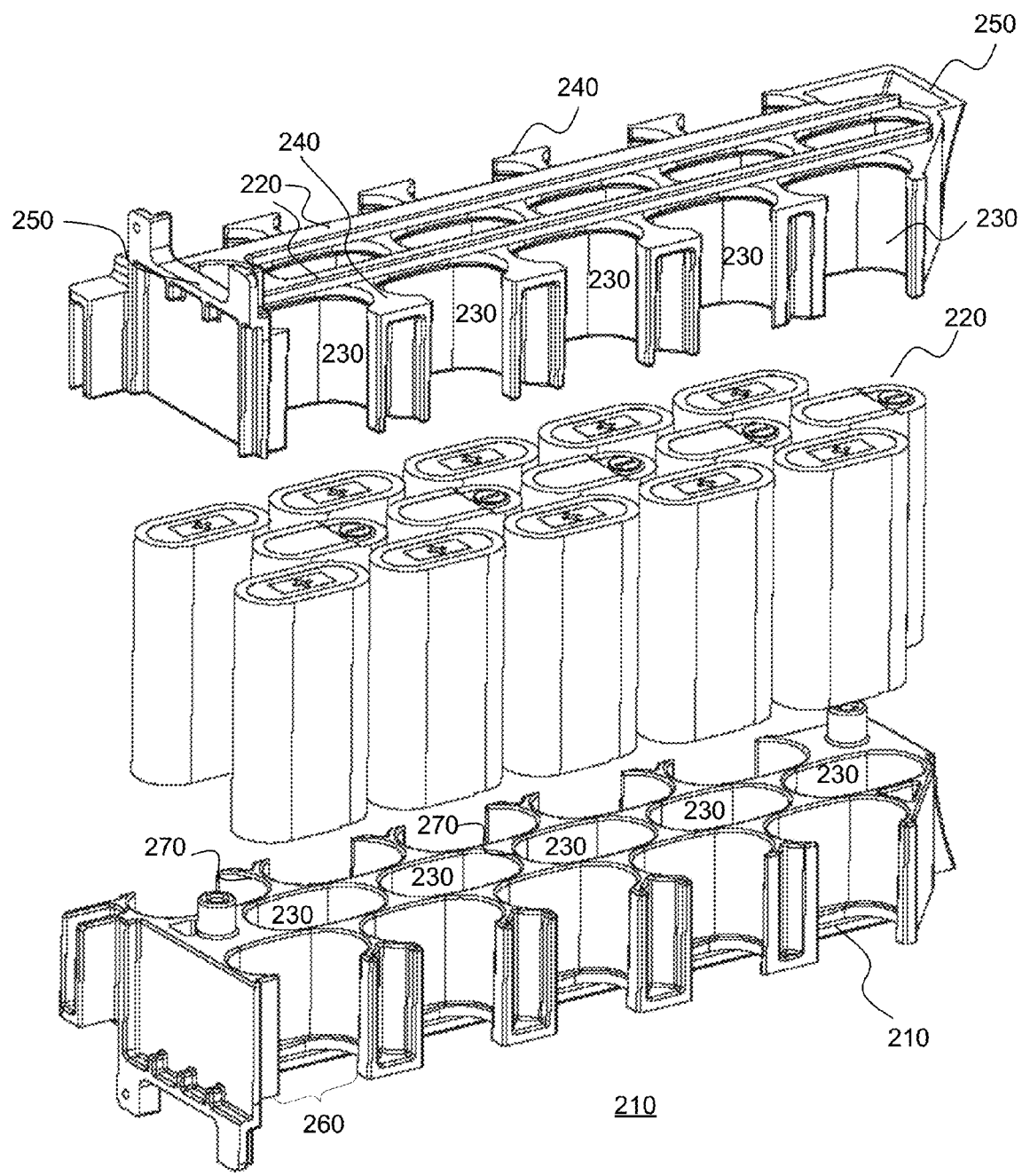
FIG. 2 depicts an exploded view of a shielding receptacle sized and shaped to receive a plurality of individual battery cells in accordance with an example.

In one embodiment a shielding receptacle can be sized and shaped to receive a plurality of individual battery cells (as in FIG. 2). In another embodiment, the shielding receptacle can include a plurality of cell pockets and a plurality of walls along the exterior of the shielding receptacle (as in FIG. 2).

FIG. 2 shows an exploded view of a shielding receptacle 210 sized and shaped to receive a plurality of individual battery cells 220. FIG. 2 further illustrates that the shielding receptacle can include a plurality of cell pockets 230 and a plurality of walls along the exterior of the shielding receptacle 210. In another embodiment, the shielding receptacle 210 can include four walls 240 and 250, where two opposite walls are side walls 240 and two opposite walls are end walls 250. In another embodiment, the end walls 250 of the shielding receptacle 210 can be substantially parallel to each other and the side walls 240 of the shielding receptacle 210 can be substantially parallel to each other. In another embodiment, the two side walls 240 can include one or more openings or gaps 260. In another embodiment, the shielding receptacle 210 can include one or more walls along the interior of the shielding receptacle 220 (e.g. interior walls). In another embodiment, the cell pockets 230 can be located between at least two of the walls 240, 250, and/or 220. In another embodiment, each cell pocket can be separated from other cell pockets 230 by a shielding barrier 270. In another embodiment, a cell pocket 230 can be defined as a region between at least two shielding barriers 270 or by a region between a side wall 240 or an end wall 250 and at least one shielding barrier 270.

In one embodiment, the side walls 240, end walls 250, interior walls 220, and/or shielding barriers 270 can divide the interior of the shielding receptacle 210 into the plurality of cell pockets 230. In another embodiment, the shielding receptacle 210 can be formed using injection molding. In one example, the shielding receptacle 210 can include fixed cell pockets 230 where the shielding barriers 270 are integrally formed with at least one of the walls 240, 250, and/or 220 of the shielding receptacle 210 as a one-piece construction. In another embodiment, the fixed cell pockets 230 can be integrally formed with two opposing walls 240 or 250 (such as two side walls 240) as a one-piece construction. In another embodiment, the fixed cell pockets 230, all four of the walls 240 and 250 (i.e., the two side walls 240 and the two end walls 250), and the interior walls 220 are all a one-piece construction.

In another embodiment, the shielding receptacle 210 can comprise side walls 240, end walls 250, and/or interior walls 220 with insertable shielding barriers 270 inserted between the side walls 240, end walls 250, and/or interior walls 220. In another embodiment, the shielding receptacle 210 can comprise side walls 240, end walls 250, and/or interior walls 220 with insertable shielding barriers 270 and fixed shielding barriers 270.

In one embodiment, the cell pockets 230 can be substantially circular or spherical in form. In another embodiment, the cell pockets 230 can be substantially rectangular in form. In another embodiment, each cell pocket 230 can form a substantially liquid-proof and/or air-proof compartment.

Figure 3:
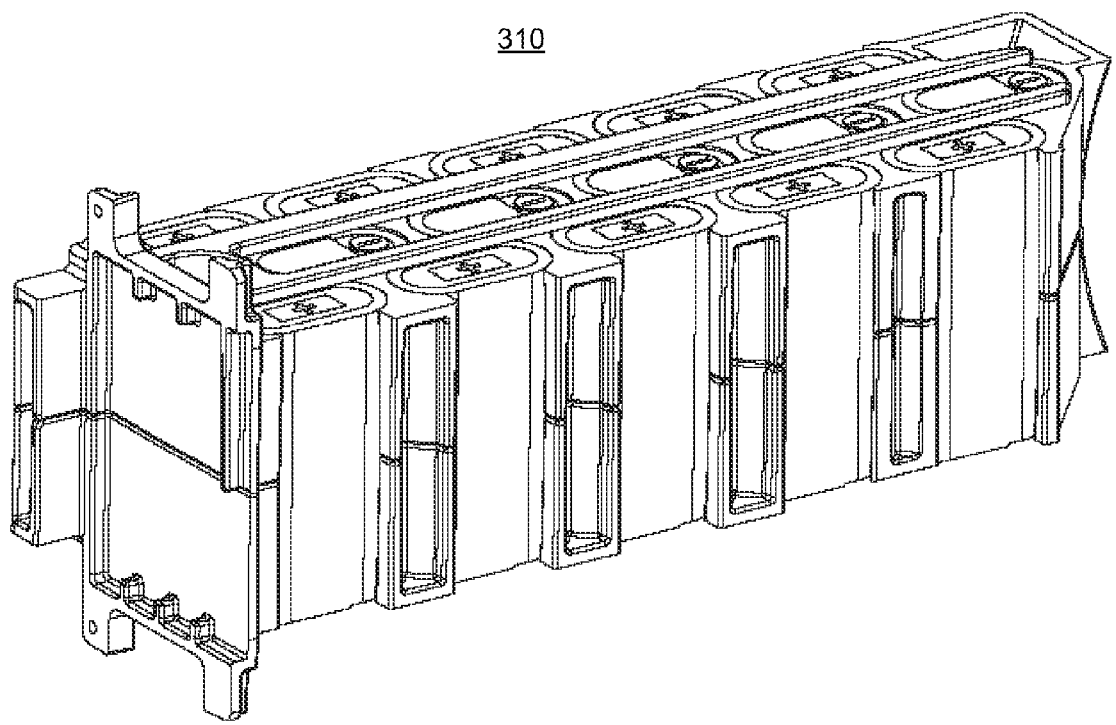
FIG. 3 depicts an assembled view of a shielding receptacle sized and shaped to receive a plurality of individual battery cells in accordance with an example.

In one embodiment, the cell pockets 230 can be oriented substantially parallel to the end walls 250 of the shielding receptacle 210. In another embodiment, the cell pockets 230 can be substantially parallel to the side walls 240 of the shielding receptacle 210. In another embodiment the shielding receptacle 210 can be a polymer, such as a high temperature resistant polymer, that has a high heat deflection rate and is injection moldable. In one embodiment the shielding receptacle 210 can be a polymer, such as a high temperature resistant polymer, that has a high heat deflection rate and is injection moldable. FIG. 3 shows an assembled view of a shielding receptacle 310 sized and shaped to receive a plurality of individual battery cells as described in FIG. 2. FIG. 3 is the same as FIG. 2 in all other aspects.

Figure 4A:
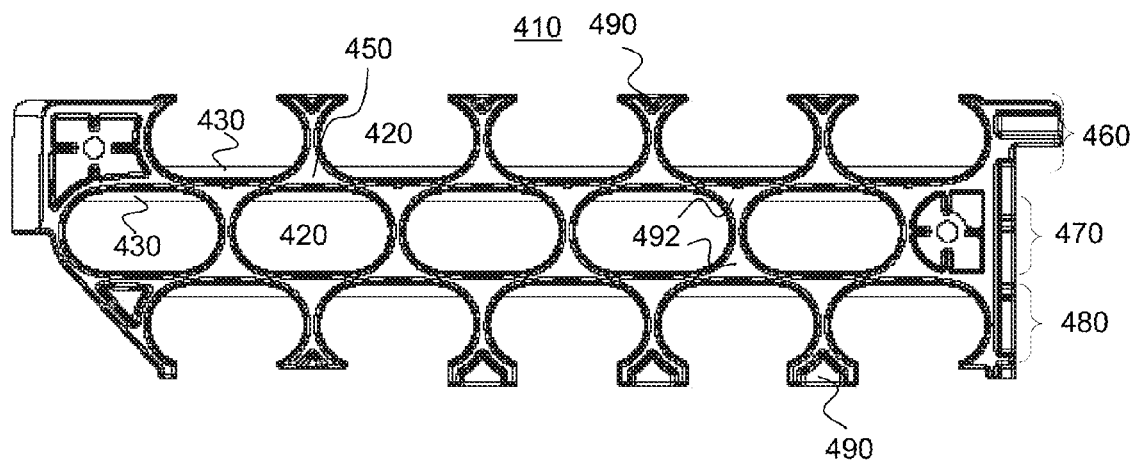
FIG. 4a depicts a shielding receptacle with a cell pocket that includes a swelling cavity in accordance with an example.
Figure 4B:
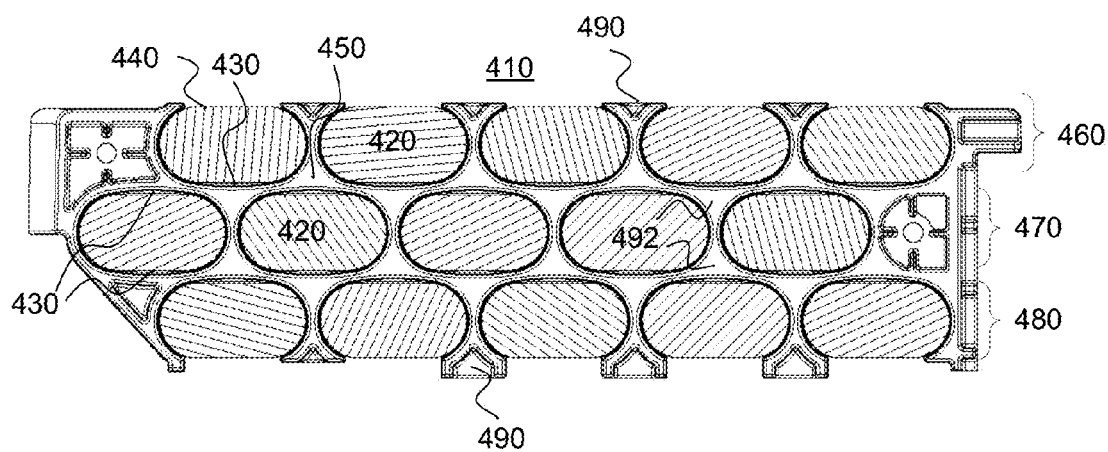
FIG. 4b depicts a shielding receptacle with a cell pocket that includes a battery cell that has partially expanded into the swelling cavity in accordance with an example.

FIGS. 4a and 4b illustrate a shielding receptacle 410 with one or more cell pockets 420 with swelling cavities 430. A lithium-ion battery can have a current limit, e.g. a maximum amount of current that can be put through a lithium-ion cell. In one example, when a lithium-ion battery is being recharged and the recharge current exceeds the current limit, the lithium-ion battery can be overcharged. When a lithium-ion battery is being overcharged, lithium can build up faster than the lithium can be dissipated from a battery cell. When lithium builds up faster than the lithium can dissipate from a battery cell, metallic lithium plates can form on an anode of the battery cell and a cathode can become an oxidizing agent. When the metallic lithium plates form, the battery cell can lose stability.

In one embodiment, when the metallic lithium plates form on the anode and the cathode becomes an oxidizing agent and loses stability, the lithium-ion battery can emit warm gasses (e.g. heat) and cause the lithium ion battery to swell. In another embodiment, a battery pack can include a charging module to limit an amount of current during recharging of a battery cell and prevent overcharging the battery cell. In one example, when the charging module detects overcharging, the charging module can stop the recharging of the battery pack.

FIGS. 4a and 4b show the shielding receptacle 410 that includes the swelling cavity or area 430 for a battery cell 440, such as a lithium ion battery, to swell or expand. In one example, the shielding receptacle 410 can have a swelling cavity 420 of dead space or air space for the battery 440 to expand or swell into. FIG. 4a shows a shielding receptacle 410 with a cell pocket 420 that includes a swelling cavity 430. FIG. 4b shows a shielding receptacle 410 with a cell pocket 420 that includes a battery cell 440 that has partially expanded into the swelling cavity 430. In another embodiment, the one or more of the cell pockets 420 can include one or more swelling cavities or areas 430 for a battery 440 to swell or expand into. In another embodiment, the shielding receptacle 410 can include a heat sink and/or thermal material 450 to absorb heat emitted from a battery cell 440. In one example, the thermal material 450 can be heat shielding material integrated into the shielding receptacle and separating cell pocket. In another embodiment, a cell pocket of a shielding receptacle can be coated with heat resistive materials, such as an acrylonitrile butadiene styrene material.

FIGS. 4a and 4b further illustrate that the shielding receptacle 410 can include one or more rows, such as rows 460, 470, and/or 480, of cell pockets 420. In one embodiment, one or more cell pockets 420 of a first row 460 can be offset from one or more cell pockets 420 of a second row 470. In another embodiment, the one or more cell pockets 420 of the shielding receptacle 410 can be configured in a honeycomb pattern. In one example, the honeycomb pattern can be comprised of small chambers, each completely separate from all other chambers. In another embodiment, the shielding receptacle 410 can be divided into an array of cell pockets 420.

In one embodiment, one or more rows (such as rows 460 or 480) of cell pockets 420 can be located along an exterior wall 490 of the shielding receptacle 410 and one or more rows (such as rows 470) can be located between interior walls 492 of the shielding receptacle 410. In another embodiment, a cell pocket 420 and/or a shielding barrier can include coolant channels. In another embodiment, a cell pocket 420 and/or a shielding barrier can include extinguishing materials.

In one embodiment, each cell pocket 420 can hold an individual battery cell 440. In another embodiment, the shielding receptacle 410 can also include a plurality of walls along the outer parameter of the shielding receptacle 410. In another embodiment, a battery pack can include one or more shielding receptacles 410 with one or more cell pockets 420.

Figure 5:
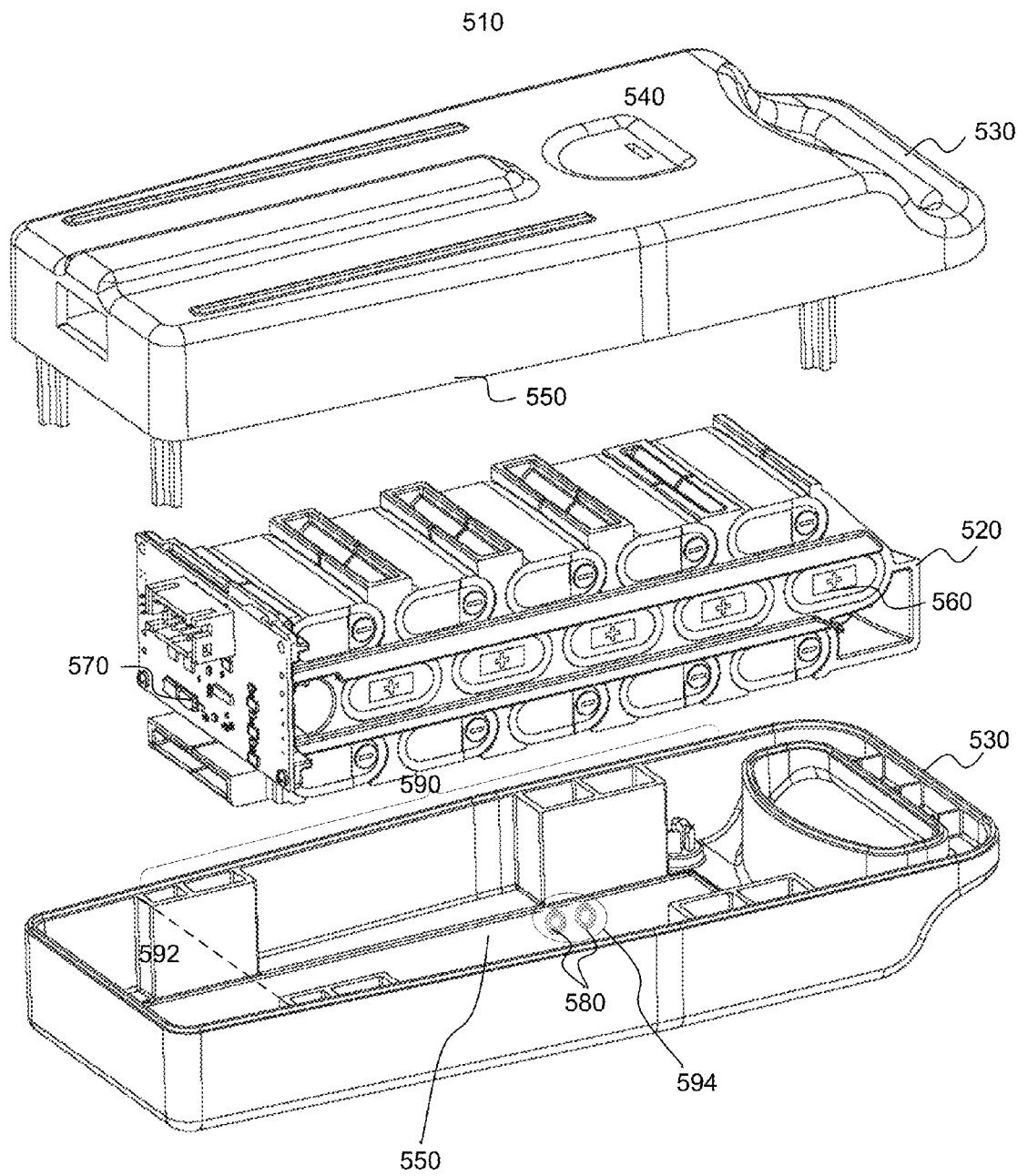
FIG. 5 depicts an exploded view of a battery pack that includes a shielding receptacle in accordance with an example.

FIG. 5 shows an exploded view of a battery pack 510 that includes a shielding receptacle 520. In one embodiment, the battery pack can comprise a housing 530. In another embodiment, the housing 530 can comprise an outer surface 540 and an inner cavity 550. In another embodiment, the inner cavity 550 can be divided into a plurality of sections or compartments. In another embodiment, the battery pack can contain one or more battery energy cells 560, power management module 570, and one or more wireless transfer coils 580. In another embodiment, the sections or compartments can include a battery bay 590, a power management compartment 592, and/or a wireless transfer station compartment 594. In one embodiment, the shielding receptacle 520 and one or more battery cells 560 can be located in the battery bay 590. In one embodiment, one or more of the plurality of sections or compartments can be separated by heat resistant or heat reflective material to reduce heat transfer between one or more of the sections or compartments. In one embodiment, the power management module 570 can be located within the power management compartment 592.

In one embodiment, a wireless transfer station can be located in the wireless transfer station compartment 594. In one example, a wireless transfer station can include wireless transfer coils 580, such as transmitting coils and/or receiving coils, which can be coupled to the battery pack 530 or integrated into the battery pack 530 and fully sealed or enclosed. In another embodiment, the wireless transfer station can be configured to transfer energy and/or data to another battery pack, another wireless transfer station, and/or a device using the wireless transfer coils 580. In one example, the battery pack 530 with the integrated wireless transfer coils 580 can have no physical electrical contact points or physical electrical connection points for charging the battery pack 530, communication information, data transfer, and/or power management control.

One advantage of separating the battery pack 530 into different section or compartments can be to disperse heat generated by components located in each compartment. In one example, one or more batteries or battery cells can be baked or prematurely aged when exposed to exterior heat from a battery pack component such as the power management module 570.

In one embodiment, the battery pack 530 can be completely sealed or hermetically sealed. In another embodiment, a battery pack can be sealed against water, solvents, cleaning supplies, dust, and other particulates by hermetically sealing the battery pack. For example, a hermetically sealed battery pack can be airtight, e.g. impervious to air and/or gas.

In one embodiment, the battery pack case can include an injection hole extending from the exterior surface of the battery pack to the inner cavity of the battery pack. In one embodiment, the battery pack case can be hermetically sealed by placing the battery energy cells, power management module, the transmission coil, and/or the receiving coil in the battery pack case and welding (such as ultrasonic welding) the battery pack case closed. When the battery pack case is welded closed, material, such as a liquid or a foam, can be injected through the injection hole to the battery pack case to encapsulate the battery energy cells, power management module, the transmission coils, and/or the receiving coils in a waterproof material. In another embodiment, the battery pack case can be a waterproof housing enclosure. In another embodiment, the battery pack case can be hermetically sealed by placing the battery energy cells, power management module, the transmission coil, and/or the receiving coil in the battery pack case and using an O-ring to seal two or more pieces of the battery together. In another embodiment, the battery pack case can be sealed using a silicon over mold gasket around one or more seams of the battery pack case, such as exterior seams of the battery pack case.

Figure 6:
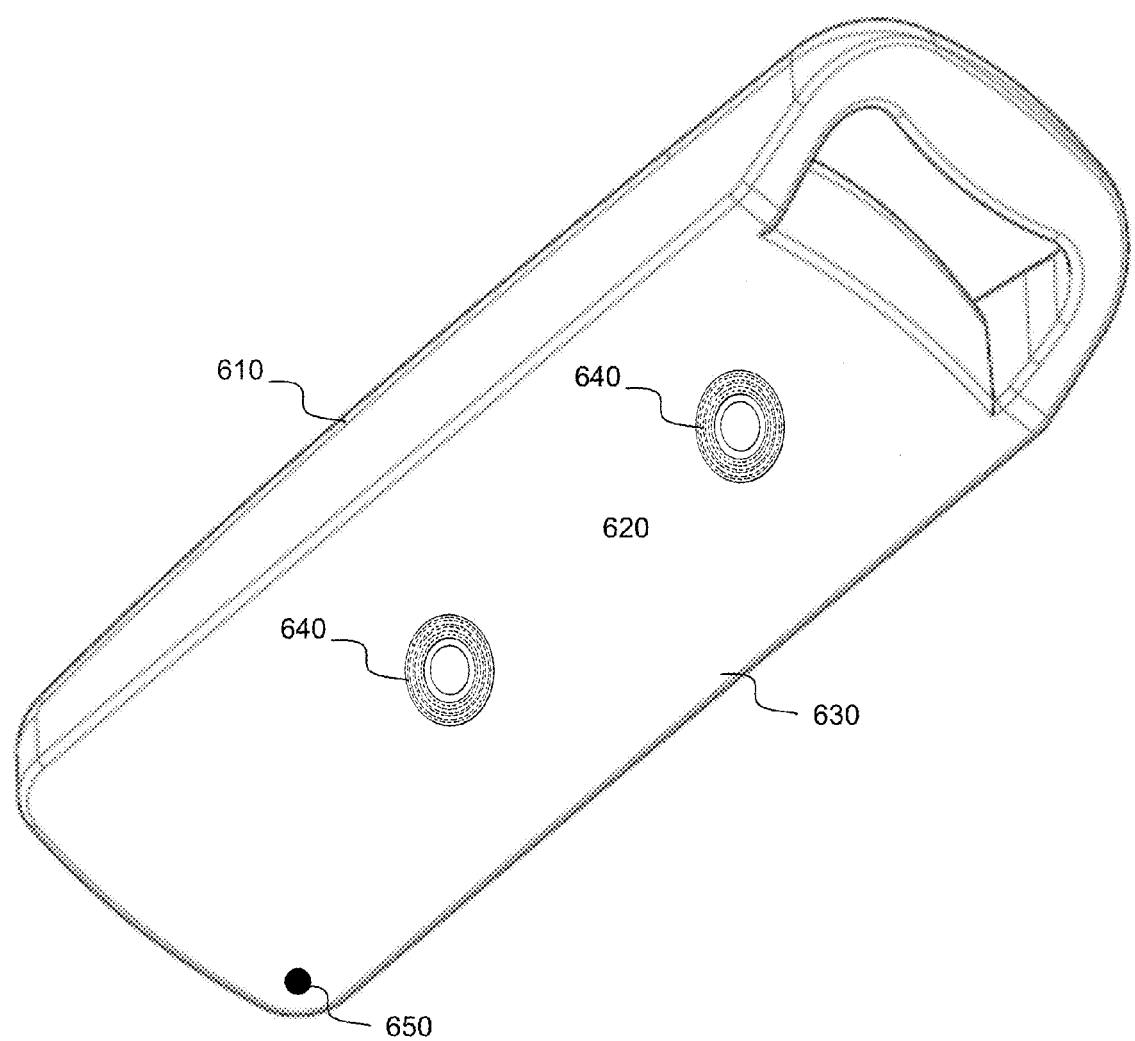
FIG. 6 depicts a wireless transfer station case in accordance with an example.

FIG. 6 illustrates one exemplary embodiment of a wireless transfer station case 610. In one embodiment, the wireless transfer station can be a battery pack. FIG. 6 further illustrates that the wireless transfer station case 610 can include a flat surface 620 along part of an exterior surface of a housing 630 of the wireless transfer station case 610. In one embodiment, one or more wireless transfer coils 640 can be integrated into the flat surface 620 of the wireless transfer station case 610 beneath the exterior surface. One advantage of a wireless transfer station case 610 with flat surface 620 along part of the exterior surface is that the one or more wireless transfer coils 640 of the wireless transfer station case 610 can abut next to a wireless transfer station with one or more wireless transfer coils to minimize the distance between the one or more wireless transfer coils 640 of the wireless transfer station case 610 and the one or more wireless transfer coils of the wireless transfer station.

In one embodiment, the wireless transfer station case 610 can include an injection hole 650 extending from the exterior surface of the wireless transfer station case 610 to an inner cavity of the wireless transfer station case 610. In one embodiment, the wireless transfer station case 610 can be hermetically sealed by placing the battery energy cells, power management module, and/or the wireless transfer station (as shown in FIG. 1) in the wireless transfer station case 610 and welding (such as ultrasonic welding) the wireless transfer station case 610 closed. When the wireless transfer station case 610 is welded closed, material, such as a liquid or a foam, can be injected into the injection hole 650 of the wireless transfer station case 610 to encapsulate the battery energy cells, the power management module, and/or the wireless transfer station in a waterproof material.

Often, rechargeable batteries are used as a replenishable energy source for electronic devices. In one embodiment, a battery pack can include one or more rechargeable batteries. In one example, the one or more rechargeable batteries can be a lead-based battery, a lithium-based battery, a nickel based battery, or another type of chemical storage battery. Traditionally, a rechargeable battery pack provides energy to an electronic device using physical electrically conductive connections between the rechargeable battery pack and the electronic device. When the traditional rechargeable batteries of the rechargeable battery pack are depleted, the rechargeable batteries can be replenished by connecting physical electrically conductive contacts between the rechargeable battery pack and a battery charger.

In one embodiment of the present invention, a wireless transfer station can receive energy and/or send energy to another device, such as another wireless transfer station, using a wireless energy transfer scheme (e.g. transfer energy without wires). A wireless energy transfer scheme can be any form of wireless energy transfer associated with the use of electric fields, magnetic fields, electromagnetic fields, and so forth that allows electrical energy to be transmitted between two or more wireless transfer elements without using physical electrical contacts. In one example, a wireless energy transfer of wireless energy can be a transfer of electrical energy from an energy source to an electrical load without the use of interconnecting wires or physical electrical contacts.

In one embodiment, the wireless transfer station can include one or more wireless transfer coils to transfer energy and/or data with other wireless transfer stations. The wireless transfer coil can include one or more power management modules to control the energy transfers and/or data transfers with the other wireless transfer stations.

Examples of a wireless transfer station includes a wireless energy rechargeable battery pack, a wireless energy transfer platform and/or data transceiver integrated into a medical cart, a wireless energy transfer platform and/or data transceiver integrated into an electronic device, a wireless energy transfer platform and/or data transceiver integrated into a piece of furniture, a wireless energy transfer platform and/or data transceiver integrated into a plate mounted to a wall, a wireless energy transfer platform and/or data transceiver integrated into a device (such as a medical device or medical equipment), and so forth.

In one example, the wireless transfer station can be a wireless energy battery pack that can be attached to a device, such as a medical cart or medical equipment. The wireless transfer station that transfers energy and/or data with the device can also relay the energy and/or data with other devices and/or wireless transfer stations. These examples are not intended to be limiting. The wireless transfer station can be implemented in a variety of electronic devices and mounting locations.

In one embodiment, the wireless transfer station can receive data from and/or send data or information to another device, such as another wireless transfer station, using a wireless data transfer scheme. In another embodiment, the wireless data transfer scheme can be any form of data transfer associated with a communications network. In another embodiment, the communications network can be a cellular network. The cellular network can be configured to operate based on a cellular standard, such as the third generation partnership projection (3GPP) long term evolution (LTE) Rel. 8, 9, 10, 11, or 12 standard, or the institute of electronic and electrical engineers (IEEE) 802.16p, 802.16n, 802.16m-2011, 802.16h-2010, 802.16j-2009, or 802.16-2009 standard. In another embodiment, the communications network can be a wireless local area network (such as a wireless fidelity network (Wi-Fi)) that can be configured to operate using a standard such as the IEEE 802.11-2012, IEEE 802.11ac, or IEEE 802.11ad standard. In another embodiment, the communications network can be configured to operate using a Bluetooth standard such as Bluetooth v1.0, Bluetooth v2.0, Bluetooth v3.0, or Bluetooth v4.0. In another embodiment, the communications network can be configured to operate using a ZigBee standard, such as the IEEE 802.15.4-2003 (ZigBee 2003), IEEE 802.15.4-2006 (ZigBee 2006), or IEEE 802.15.4-2007 (ZigBee Pro) standard. In another embodiment, the wireless data transfer scheme can be any form of data transfer associated with electric fields, magnetic fields, or electromagnetic fields that is transmitted between two or more wireless transfer elements without using physical electrical contacts.

In one embodiment, the wireless transfer station can include one or more wireless transfer elements. In one example, a wireless transfer element can be a wireless transfer coil. In one embodiment, the wireless transfer coil can be a coil used for transmitting and/or receiving energy and/or data using magnetic inductance and/or magnetic resonance.

Figure 7:
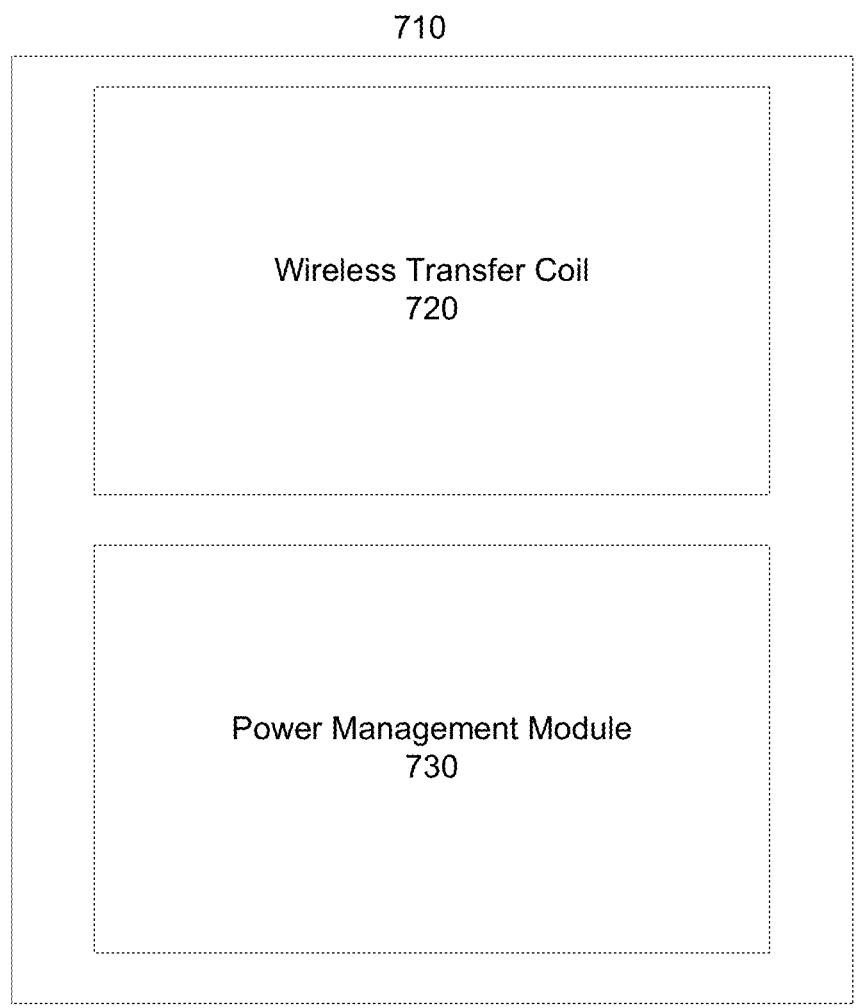
FIG. 7 depicts another wireless transfer station case in accordance with an example.

FIG. 7 illustrates a wireless transfer station 770. FIG. 7 further illustrates that the wireless transfer station 770 can include a wireless transfer coil 720 and a power management module 730. In one example, the power management module 730 can convert energy received from an energy source, such as another wireless transfer station or an alternating current (AC) energy outlet, a selected current level, a selected voltage level, and/or a selected wattage level. In another embodiment, the wireless transfer station 770 can include one or more batteries, such as rechargeable batteries. In one embodiment, the wireless transfer coil 720 can comprise a transmitting coil and/or a receiving coil.

Figure 8:
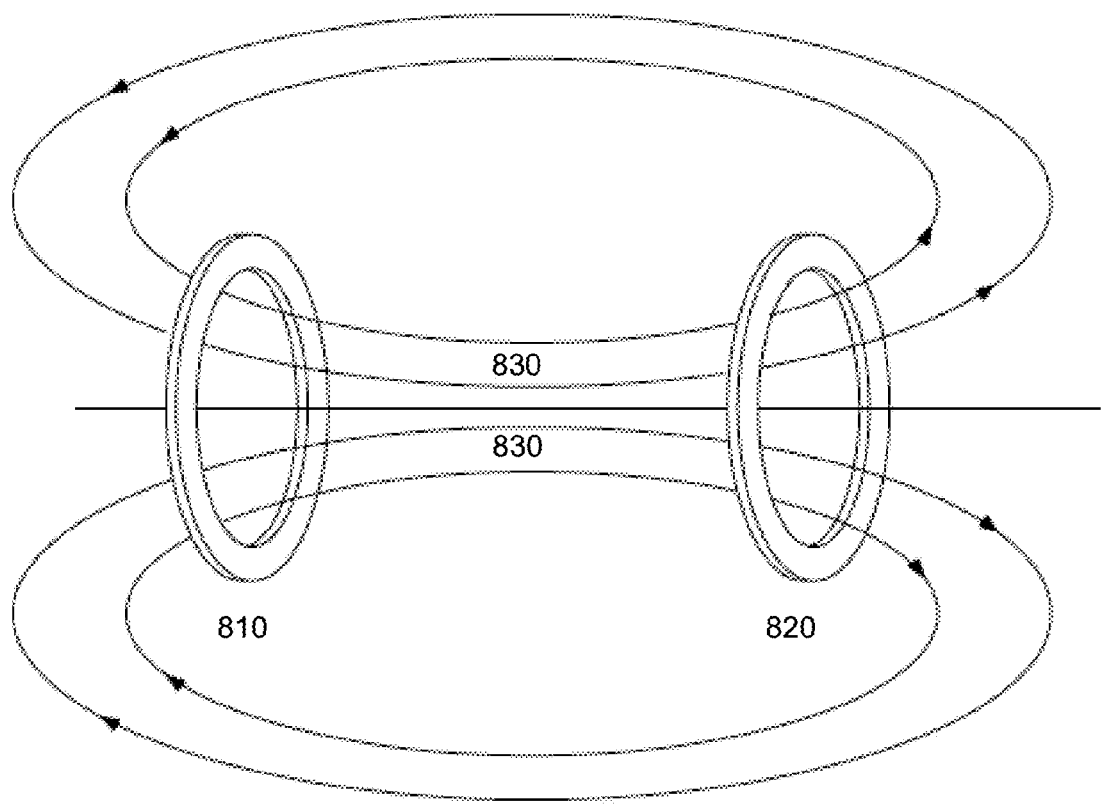
FIG. 8 depicts a transferring of energy or data between a plurality of wireless transfer coils in accordance with an example.

FIG. 8 illustrates an example of transferring energy or data between a plurality of wireless transfer coils 810 and 880. FIG. 8 further illustrates that one of the plurality of wireless transfer coils 810 can be a transmitting coil 810 and another one of the plurality of wireless transfer coils 880 can be a receiving coil 880. In one embodiment, energy and/or data can be transferred from the transmitting coil 810 to the receiving coil 880 by coupling the transmitting coil 810 with the receiving coil 880 to enable the energy or data to be transferred over a gap or distance. In one example, wireless energy can be transferred by generating a magnetic field 830 (such as an electromagnetic field) at the transmitting coil 810 and positioning the receiving coil 880 within the magnetic field 830 to induce a current at the receiving coil 880. The process of inducing a current at the receiving coil is referred to as coupling the receiving coil 880 to the transmitting coil 810. In one embodiment, the wireless transfer coil coupling for wireless energy or data transfer can be a magnetic induction coupling. In another embodiment, the wireless transfer coil coupling for wireless energy transfer can be a magnetic resonant coupling.

In one embodiment, the transmitting coil 810 can be a transmitting induction coil and the receiving coil 880 can be a receiving induction coil. The wireless transfer station can use a magnetic field to transfer energy between the transmitting coil 810 coupled to a first object (such as a wireless transfer station) and a receiving coil 880 of a second object (such as another wireless transfer station) without any direct contact between the transmitting coil 810 and the receiving coil 880, e.g. inductive coupling.

In one embodiment, inductive coupling can occur when the transmitting coil 810 creates a magnetic field 830 (such as an alternating electromagnetic field) using an energy source, such as an alternating current (AC) energy outlet or a direct current (DC) battery. A current can be induced at the receiving coil 880 using the magnetic field when the receiving coil 880 is located within the magnetic field 830.

In one example, when the transmitting coil 810 and the receiving coil 880 are within a threshold proximity distance, the transmitting coil 810 and the receiving coil 880 can couple to form an electric transformer. In one embodiment, current from the receiving coil 880 can be transferred to a battery or an electronic device. In another embodiment, the current can be stored in one or more energy sources of the wireless transfer station, such as a battery. In another embodiment, the current can be transferred to a device coupled to the wireless transfer station. In one embodiment, an impedance of one or more transmitting coils 810 can be substantially matched with an impedance of one or more receiving coils 880.

In one embodiment, the transmitting coil 810 can be a transmitting resonant coil and the receiving coil 880 can be a receiving resonant coil. A wireless resonant transfer can be a resonant transmission of energy or data between at least one transmitting coil 810 and at least one receiving coil 880. In another embodiment, at least one transmitting coil 810 and at least one receiving coil 880 can be tuned to resonate at a same frequency or a substantially same frequency.

In one example, resonant transmission of wireless energy can occur when the transmitting coil and the receiving coil are constructed to resonate at the same frequency or approximately the same frequency. The transmitting coil 810 can be configured to oscillate current at the resonant frequency of the coils to transfer energy and/or data. The oscillating current of the transmitting coil 810 can generate an oscillating magnetic field at the selected resonant frequency of the receiving coil. When the receiving coil 880 is positioned adjacent to the oscillating magnetic field and constructed to operate at the same frequency or substantially the same frequency as the transmitting coil 810, the receiving coil 880 can receive energy and/or data from the oscillating magnetic field.

In another embodiment, an impedance of one or more transmitting coils 810 can be substantially matched with an impedance of one or more receiving coils 880 for energy and/or data transfer. In another embodiment, the transmitting coil and the receiving coil can be positioned such that the receiving coil is within the near field of the magnetic field of the transmitting coil. The near field can be based within the Fraunhofer region, which can be approximately within $1/8\pi$ times the wavelength of the electromagnetic field.

One advantage of placing the receiving coil within the near field for wireless energy transfer is to reduce an amount of energy that may be radiated or leaked from the wireless transfer coils 810 and 880, e.g. energy not received at the receiving coil 880. In one embodiment, energy in a magnetic field falls off as the inverse squared of a distance ($1/d^2$) between the transmitting coil 810 and the receiving coil 880 within the near field. In one example, magnetic resonant coupling can be used to transfer energy at relatively high energy levels between the transmitting coil 810 and the receiving coil 880 and to minimize or reduce energy leaking away from the wireless transfer coils 810 and 880.

Another advantage of using a near field or a non-radiating field for wireless energy transfer can be that the near field or the non-radiating field can be used in areas adjacent to biological material, such as humans or other biological entities, with minimal or no effects to the biological material from the wireless energy transfer. In another embodiment, a wireless transfer station, such as in FIG. 7, can use a radio frequency (RF) signal, ultrasound, and/or laser beams to wirelessly transfer energy and/or data between a transmitting device and a receiving device.

Figure 9A:
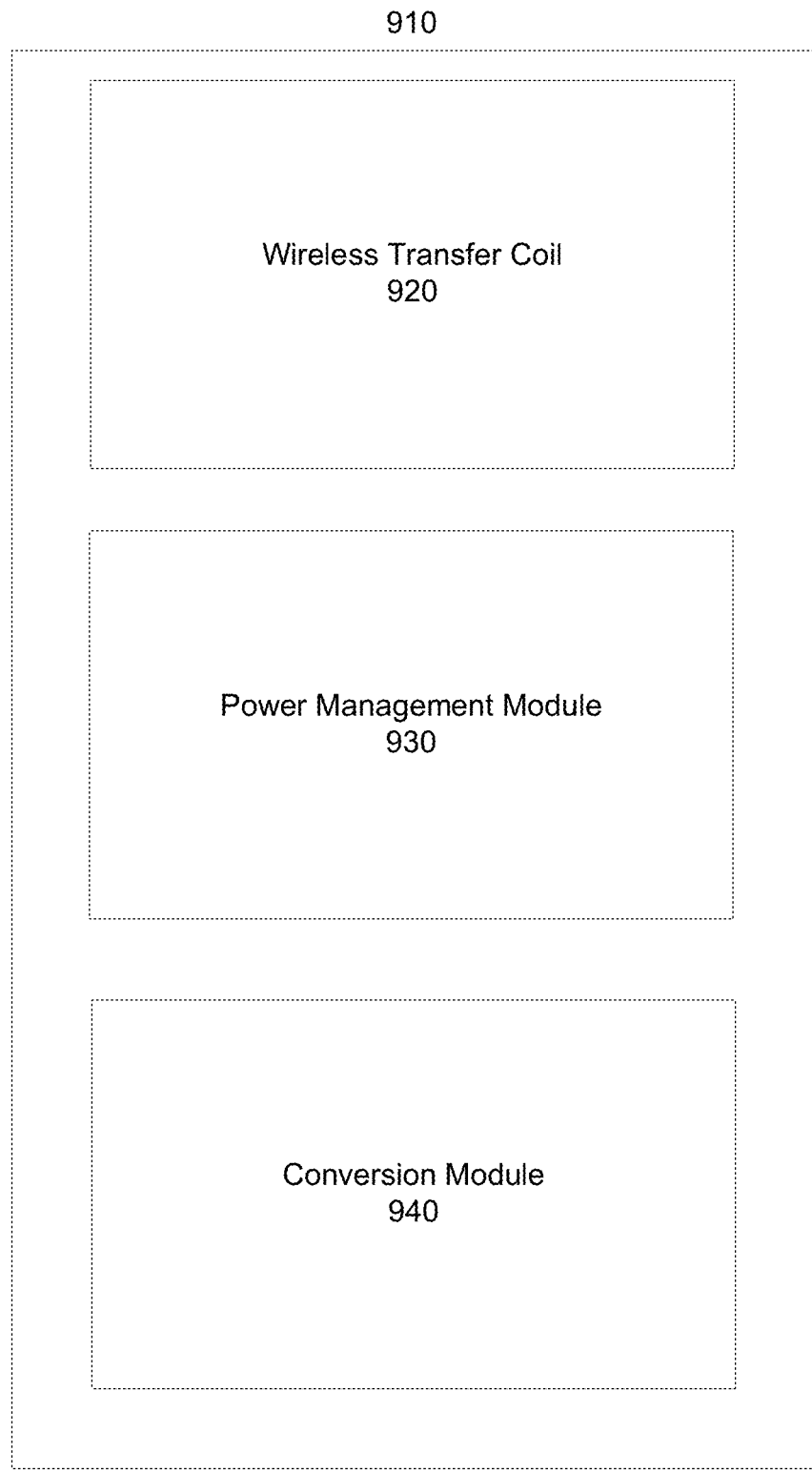
FIG. 9a depicts another wireless transfer station case in accordance with an example.

FIG. 9a shows a wireless transfer station 910 that can include: a wireless transfer coil 920, a power management module 930, and a conversion module 940. In one embodiment, the wireless transfer coil 920 can be used for resonance coupling and/or induction coupling. In one example, the conversion module 940 can be coupled to the wireless transfer coil 920 and used to switch the wireless transfer coil 920 from a resonance mode (i.e. transferring wireless energy and/or data using magnetic resonance coupling) to an induction mode (i.e. transferring wireless energy and/or data using magnetic induction coupling), or vice versa.

In one embodiment, the wireless transfer coil 920 of the wireless transfer station 910 can be used for transmitting wireless energy and/or receiving wireless energy. In one example, the conversion module 940 can be coupled to the wireless transfer coil 920 and used to switch the wireless transfer coil 920 from a receiving mode (i.e. receiving wireless energy and/or data) to a transmitting mode (i.e. transmitting wireless energy and/or data), or vice versa.

In one embodiment, when the conversion module 940 of the wireless transfer station 910 is in the transmitting mode, the conversion module 940 or the power management module 930 can convert energy received from an energy source (such as a power outlet or a battery) at a selected voltage into a high frequency alternating current and transmit the high frequency alternating current to a wireless transfer coil of another wireless transfer station. The high frequency alternating current can flow through one or more loops of the wireless transfer coil 920 and create a varying magnetic field that can induce a current in the other wireless transfer coil. In another embodiment, when the conversion module 940 is switched to the receiving mode, a varying magnetic field from another wireless transfer station can induce an alternating current flowing through the one or more loops of the wireless transfer coil 920. The current flowing through the one or more loops can be converted into a direct current (DC) by the conversion module 940 or the power management module 930 and directed to a battery coupled to the wireless transfer station 910 or a device that is electrically coupled to the wireless transfer station 910.

In one embodiment, each wireless transfer coil 920 of a wireless transfer station 910 can be coupled to a separate conversion module 940. In another embodiment, one or more conversion modules 940 can be coupled to one or more selected groups of wireless transfer coils 920. One advantage of using a conversion module 940 for switching a wireless transfer coil 920 between transmitting mode and receiving mode can be to reduce a complexity of design and/or size of a wireless transfer station 910 by reducing a number of wireless transfer coils 920 used to transmit and/or receive wireless energy. Another advantage of using a conversion module 940 for switching a wireless transfer coil between a transmitting mode and receiving mode is to provide a dual functionality to a wireless transfer station of both transmitting and receiving wireless energy.

In one embodiment, the power management module 930 can include a current interrupt device (CID). In another embodiment, the power management module 930 can include a poly switch temperature coefficient (PTC) that can break a current flow between one or more battery cells, the power management module 930, and/or the wireless transfer coil 920 when a temperature of the one or more battery cells, the power management module 930, and/or the wireless transfer coil 920 exceeds a selected threshold.

In one embodiment, each battery cell in the wireless transfer station 910 can be connected to the power management module 930 using a current line to monitor a current of each cell and a separate voltage line to monitor a voltage of each cell. In one embodiment, the power management module 930 can include chemical fuses to provide permanent circuit interruption for selected events. In one embodiment, the chemical fuses can be controlled by the cell monitoring and cutoff circuits. When the chemical fuse is activated, the fuse can permanently disable the wireless transfer station 910 and prevent current flow. In one example, the selected events can include battery overcharge, over-current, or deep discharge conditions. In another embodiment, the power management module 930 can include a plurality of chemical fuses in parallel. In another embodiment, the wireless transfer station 910 can monitor the charge and discharge vents to determine when to activate the chemical fuse. In one example, the wireless transfer station 910 can determine when a discharge vent is open or closed. In one embodiment, when a discharge vent is closed when one or more battery cells are receiving current, the power management module 930 can activate the chemical fuse.

In one embodiment, the wireless transfer coil 920 of the wireless transfer station 910 can be used for transmitting wireless energy and/or receiving wireless energy. In one example, the conversion module 940 can be coupled to the wireless transfer coil 920 and used to switch the wireless transfer coil 920 from a receiving mode (i.e. receiving wireless energy and/or data) to a transmitting mode (i.e. transmitting wireless energy and/or data), or vice versa.

In one embodiment, when the conversion module 940 of the wireless transfer station 910 is in the transmitting mode, the conversion module 940 or the power management module 930 can convert voltage received from an energy source (such as an energy outlet or a battery) into a high frequency alternating current and send the high frequency alternating current to a wireless transfer coil of another wireless transfer station. The high frequency alternating current can flow through one or more loops of the wireless transfer coil 920 and create a magnetic field that can be received by the other wireless transfer coil. In another embodiment, when the conversion module 940 is switched to the receiving mode, a magnetic field can generate current flowing through the one or more loops of the wireless transfer coil 920. In another embodiment, the current flowing through the one or more loops can be converted into direct current (DC) by the conversion module 940 or the power management module 930 and directed to a battery coupled to the wireless transfer station 910 or a coupled device to the wireless transfer station 910.

In one embodiment, each wireless transfer coil 920 of a wireless transfer station 910 can be coupled to a separate conversion module 940. In another embodiment, one or more conversion modules 940 can be coupled to one or more selected groups of wireless transfer coils 920. One advantage of using a conversion module 940 for switching a wireless transfer coil 920 between transmitting mode and receiving mode can be to reduce a complexity of design and/or size of a wireless transfer station 910 by reducing a number of wireless transfer coil 920 required to transmit and/or receive wireless energy. Another advantage of using a conversion module 940 for switching a wireless transfer coil between a transmitting mode and receiving mode is to provide a dual functionality of a wireless transfer station of both transmitting and receiving wireless energy.

Figure 9B:
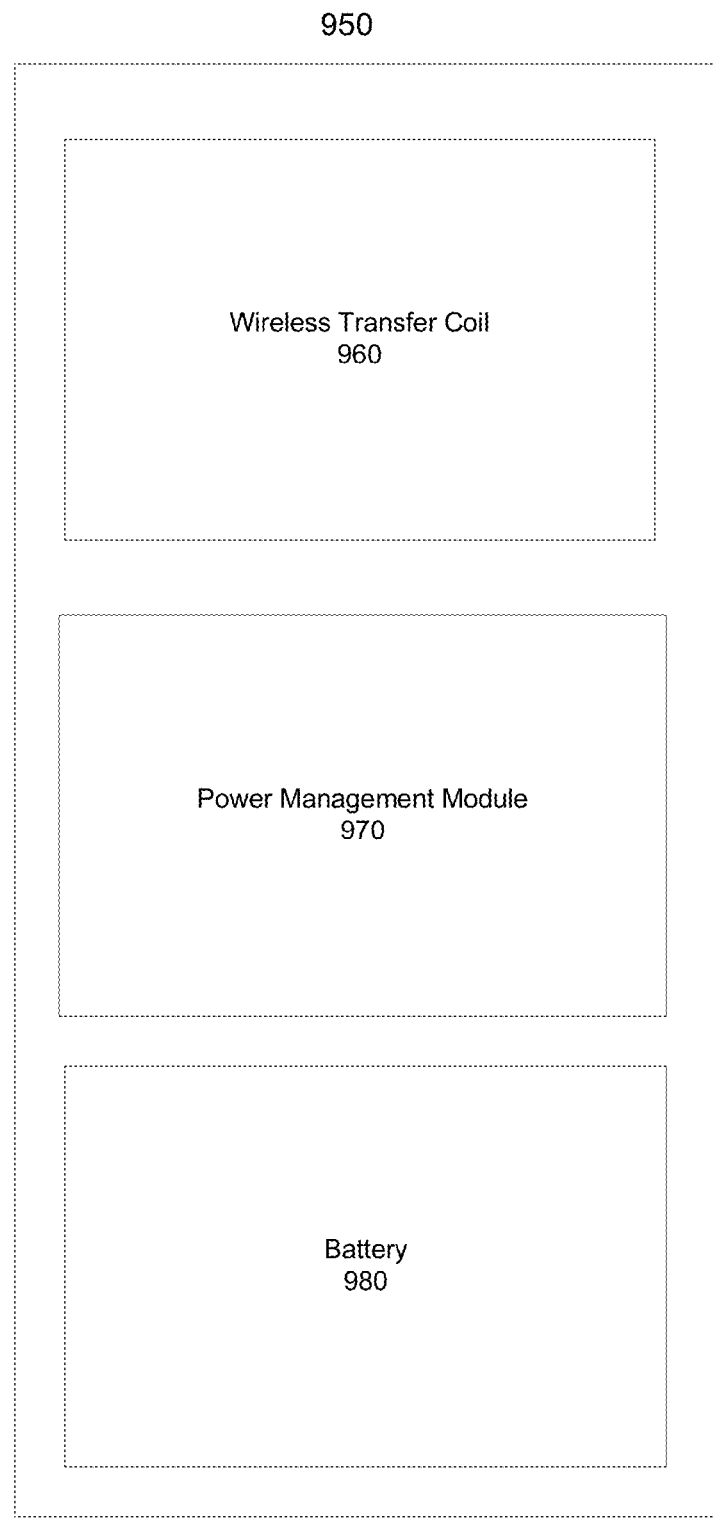
FIG. 9b depicts another wireless transfer station case in accordance with an example.

FIG. 9b illustrates a wireless transfer station 950. FIG. 9b further illustrates that the wireless transfer station 950 can include: a wireless transfer coil 960; a power management module 970; and a battery 980. The battery 980 can comprise a plurality of batteries, such as rechargeable batteries. In one example, the power management module 970 can convert energy received using the wireless transfer coil 960 from an energy source, such as another wireless transfer station or an alternating current (AC) energy outlet, to a selected current level at a selected voltage level to provide a selected wattage level. In one embodiment, the power management module can transfer the converted energy to the battery 980 to store the energy.

Figure 10:
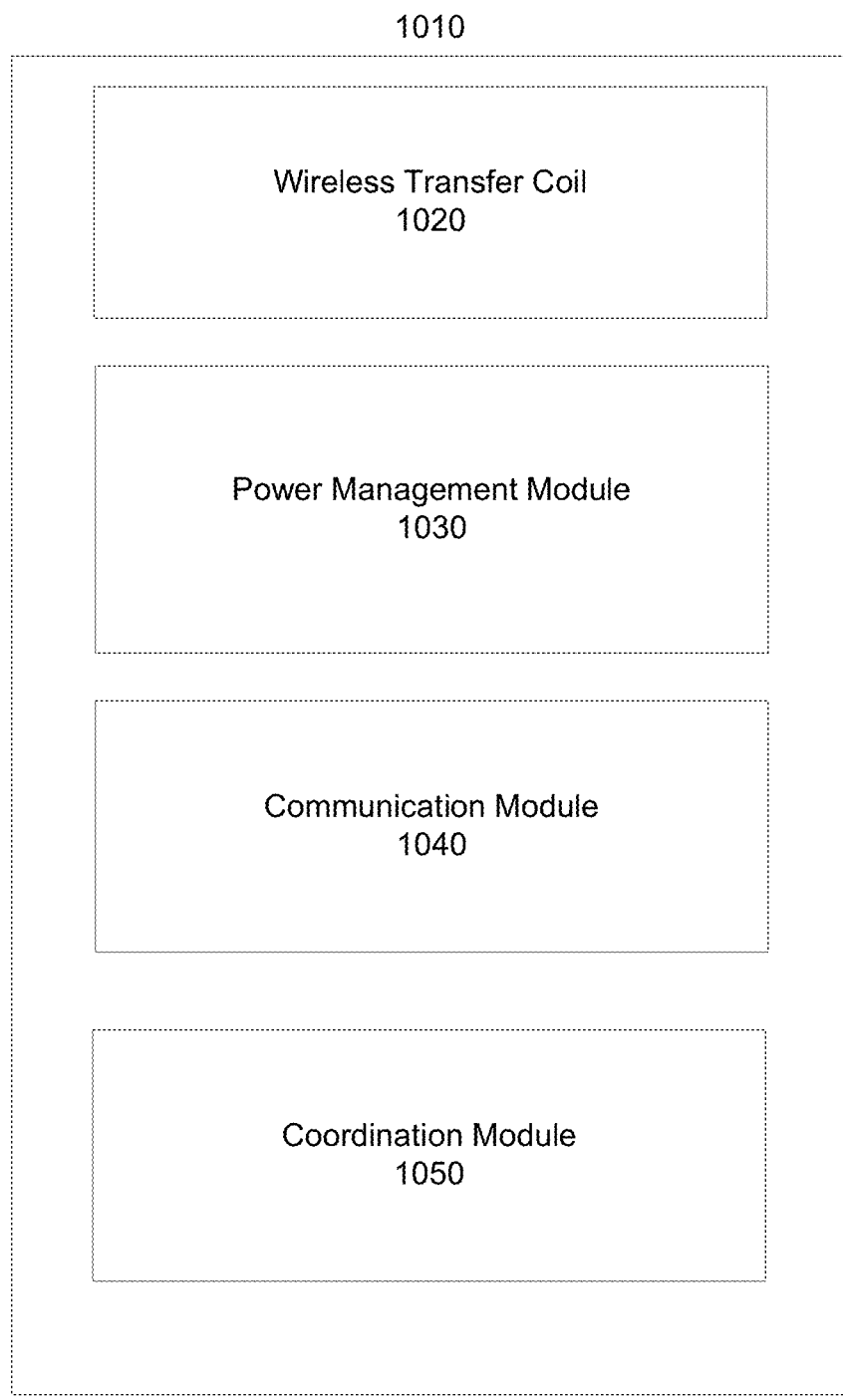
FIG. 10 depicts another wireless transfer station case in accordance with an example.

FIG. 10 shows a wireless transfer station 1010 that can include: a wireless transfer coil 1020, a power management module 1030, a communications module 1040, and/or a coordination module 1050. In one embodiment, the wireless transfer station 1010 can communicate with one or more other wireless transfer stations or one or more devices using the communication module 1040.

In one embodiment, the communication module 1040 of the wireless transfer station 1010 can use a communications network to communicate the data to a device and/or another wireless transfer station. In another embodiment, the communications network can be a cellular network that may be a 3GPP LTE Rel. 8, 9, 10, 11, or 12 or IEEE 802.16p, 802.16n, 802.16m-2011, 802.16h-2010, 802.16j-2009, 802.16-2009. In another embodiment, communications network can be a wireless network (such as a wireless fidelity network (Wi-Fi)) that may follow a standard such as the Institute of Electronics and Electrical Engineers (IEEE) 802.11-2012, IEEE 802.11ac, or IEEE 802.11ad standard. In another embodiment, the communications network can be a Bluetooth connection such as Bluetooth v1.0, Bluetooth v2.0, Bluetooth v3.0, or Bluetooth v4.0. In another embodiment, the communications network can be a ZigBee connection such as IEEE 802.15.4-2003 (ZigBee 2003), IEEE 802.15.4-2006 (ZigBee 2006), IEEE 802.15.4-2007 (ZigBee Pro).

In one embodiment, the wireless transfer station 1010 can transfer energy to one or more other wireless transfer stations, receive energy from one or more other wireless transfer stations, and/or communicate data or information with one or more other wireless transfer stations. In another embodiment, the coordination module 1050 of the wireless transfer station 1010 can coordinate when energy is transferred between wireless transfer stations and/or when data is communicated between wireless transfer stations. In another embodiment, the coordination module 1050 can use the communications module 1040 to communicate with one or more other wireless transfer stations to coordinate energy and/or data transfer between the wireless transfer station 1010 and the one or more other wireless transfer stations.

One advantage of transferring energy and/or data using a wireless transfer station 1010 is to provide a single connection point between the wireless transfer station 1010 and other wireless transfer stations and/or other devices. Another advantage of transferring energy and/or data using the wireless transfer station 1010 can be to enable a single step for both transferring energy between the wireless transfer station 1010 and other wireless transfer stations and communicate or synchronize data communicated between the wireless transfer station 1010 and other wireless transfer stations. In one example, when a first wireless transfer station (such as a wireless transfer station integrated into a medical cart) is located adjacent to a second wireless transfer station (such as a wireless transfer station integrated into a plate mounted to a wall or a floor mat), the first wireless transfer station can both receive energy from the second wireless transfer station and synchronize information with the second wireless transfer station.

In one embodiment, the coordination module 1050 can communicate with a conversion module, as in FIG. 9a, to coordinate when one or more wireless transfer coils 1020 of the wireless transfer station 1010 can transmit and/or receive wireless energy and/or data. In one example, the coordination module 1050 communicates with a conversion module, as in FIG. 9a, to coordinate transmitting and/or receiving wireless energy and/or data by coordinating when one or more wireless transfer coils 1020 are in a transmitting mode or a receiving mode, as discussed in the preceding paragraphs.

Figure 11A:
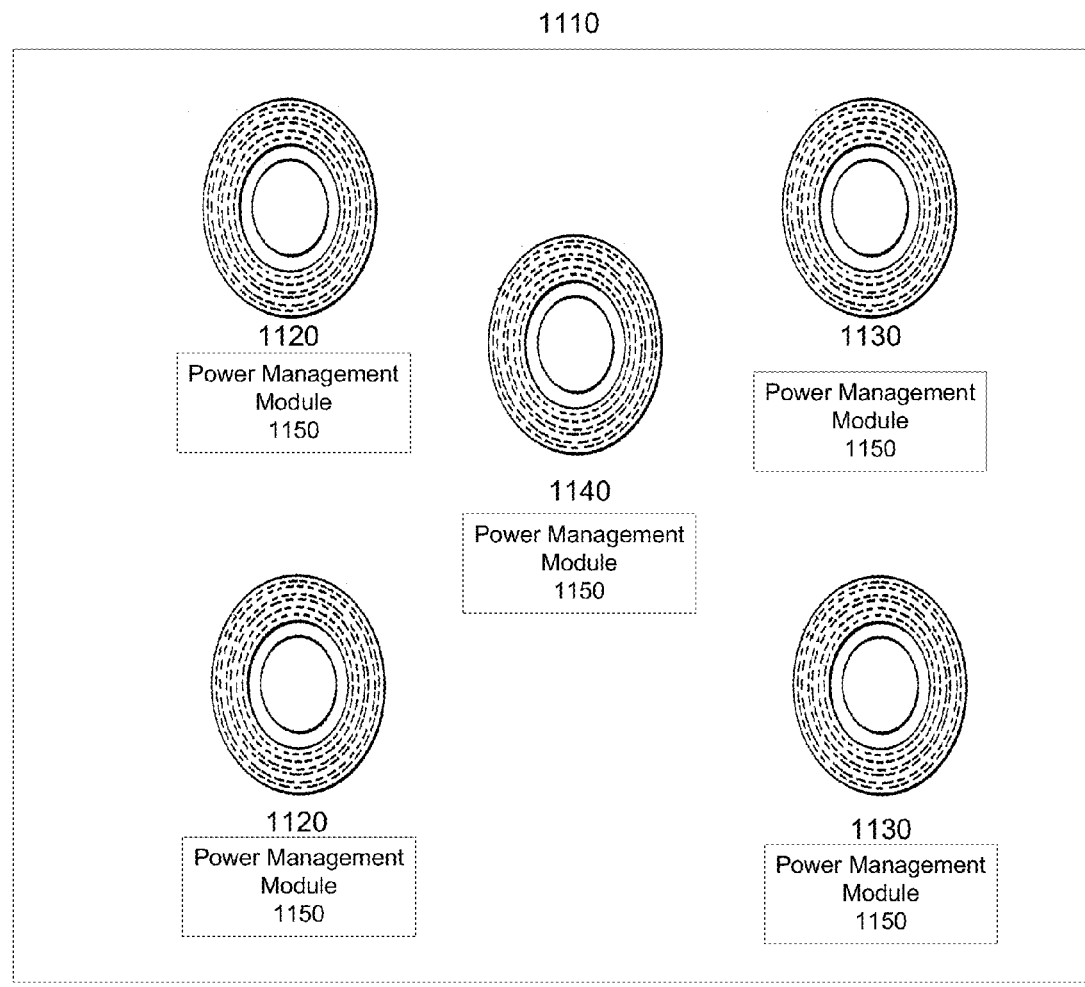
FIG. 11a depicts a wireless transfer station that includes one or more resonant wireless transfer coils or one or more induction wireless transfer coils in accordance with an example.

FIG. 11a shows a wireless transfer station 1110 that includes one or more resonant wireless transfer coils 1120 and/or one or more induction wireless transfer coils 1130. In one example, the wireless transfer station 1110 can have a resonant wireless transfer coil 1120 and can transfer energy to a resonant wireless transfer coil of a first wireless transfer station and can have an induction wireless transfer coil 1130 and can transfer energy to an induction wireless transfer coil of a second wireless transfer station. One advantage of the wireless transfer station having both resonant wireless transfer coils 1120 and induction wireless transfer coils 1130 can be to provide energy and/or data to wireless transfer stations and/or devices with only one of the resonant wireless transfer coils or the induction wireless transfer coils, thereby enabling more devices to transfer energy to the wireless transfer station.

In one embodiment, a device or another wireless transfer station can include one or more resonant wireless transfer coils and/or one or more induction wireless transfer coils. In one embodiment, the device or the other wireless transfer station receiving energy from the wireless transfer station 1110 can select whether to receive wireless energy from the one or more resonant wireless transfer coils 1120 or the one or more induction wireless transfer coils 1130 of the wireless transfer station 1110. In another embodiment, the wireless transfer station 1110 can be configured to select whether to transmit wireless energy using the one or more resonant wireless transfer coils 1120 or the one or more induction wireless transfer coils 1130. In one example, a resonant transmitting coil and a resonant receiving coil pair can have a higher energy transfer efficiency than an induction transmitting coil and an induction receiving coil pair. In this example, when the device or the other wireless transfer station includes a resonant receiving coil, the other wireless transfer station and/or the device or the wireless transfer station 1110 can be configured to use one or more resonant wireless transfer coils to perform an energy transfer.

In one embodiment, the one or more resonant wireless transfer coils 1120 and/or the one or more induction wireless transfer coils 1130 can be transmitting coils and/or receiving coils. In another embodiment, the wireless transfer station 1110 can include one or more repeater coils 1140. In one example, the repeater coil 1140 can enhance wirelessly transmitted energy of a transmitting coil, e.g. providing additional transmission energy. In another example, the repeater coil 1140 can receive the wireless energy from a transmitting coil and relay or retransmit the received energy to another repeater coil 1140 or to a receiving coil. The repeater coils can be configured as inductive repeater coils or resonant repeater coils, and associated with transmit coils and receive coils of the same kind.

In one embodiment, the one or more resonant wireless transfer coils 1120, the one or more induction wireless transfer coils 1130, and/or the repeater coil 1140 can include a power management module 1150 configured to covert energy from an energy source to a varying magnetic field. In another embodiment, the one or more resonant wireless transfer coils 1120, the one or more induction wireless transfer coils 1130, and/or the repeater coil 1140 can be coupled to a power management module 1150 configured to convert a magnetic field into energy, such as energy at a selected current level, a voltage level, a wattage level, and/or an amperage level, and transfer the energy to a battery of the wireless transfer station 1110 or a device coupled to the wireless transfer station 1110.

Figure 11B:
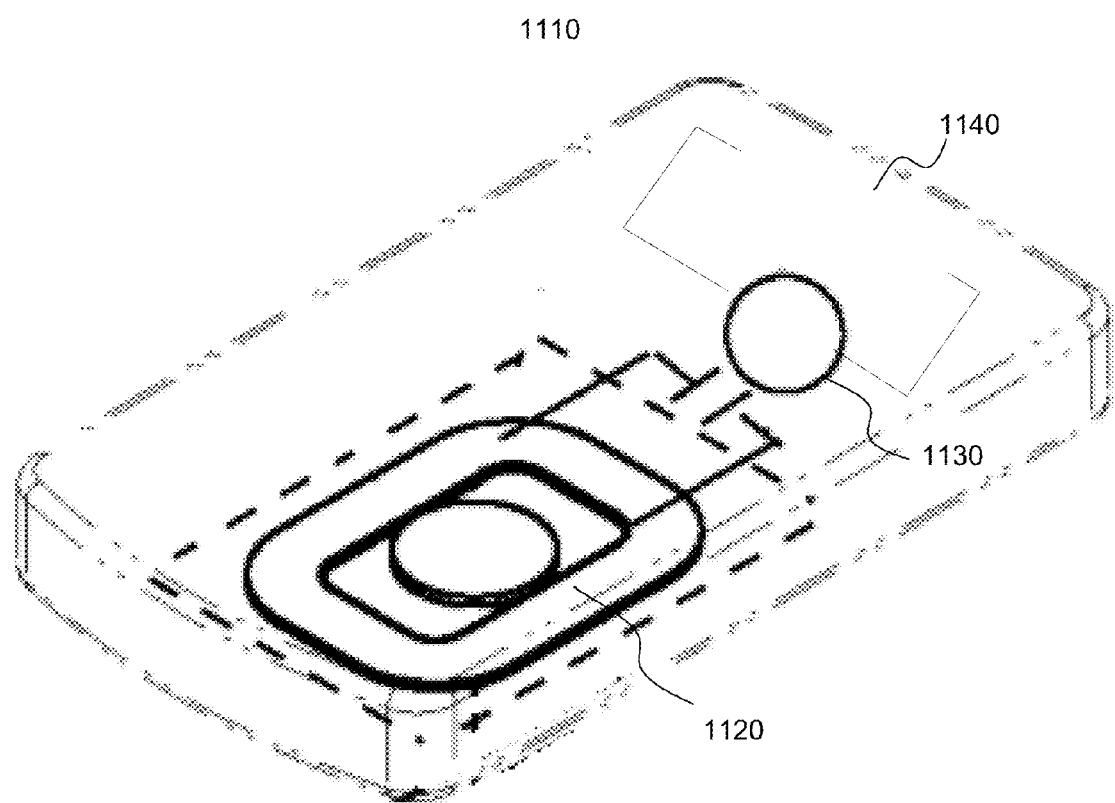
FIG. 11b depicts another wireless transfer station case in accordance with an example.

FIG. 11*b* illustrates one exemplary embodiment of the wireless transfer station 1110. In one embodiment, the wireless transfer station 1110 can be a stand-alone device used to transfer wireless energy to other devices. In another embodiment, the wireless transfer station 1110 can include a wireless transfer coil 1120 and a power management module 1130. In another embodiment, the wireless transfer station 1110 can direct energy received at the wireless transfer coil 1120 using the power management module 1130 to a device coupled to the wireless transfer station 1110.

In another embodiment, the wireless transfer station 1110 can transfer the energy received at the wireless transfer coil 1120 to the coupled device using physical electrical contacts. In another embodiment, the wireless transfer station 1110 can transfer the energy to the coupled device using the wireless transfer coil 1120. In one embodiment, the wireless transfer station 1110 can store received energy at a battery 1140.

Figure 11C:
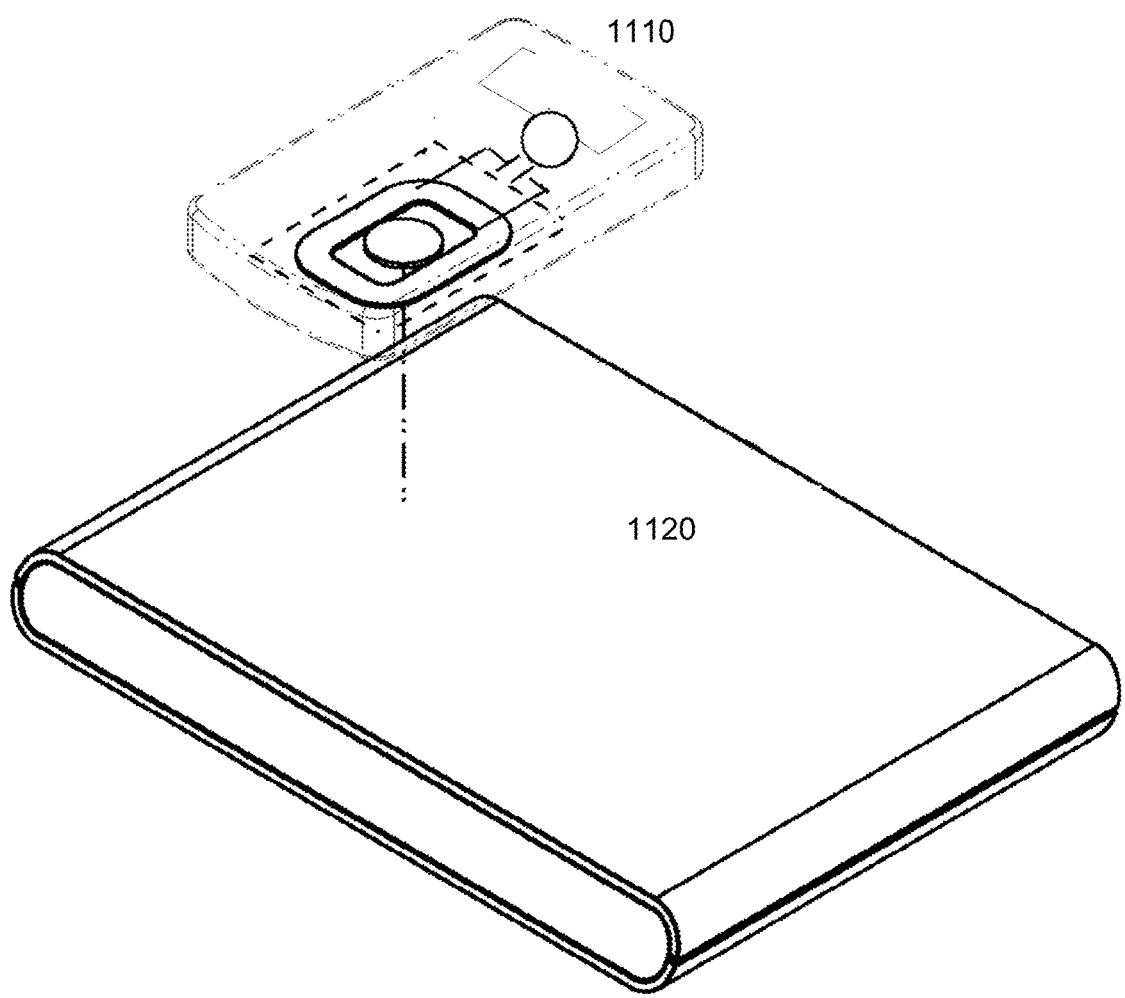
FIG. 11c depicts a wireless transfer station integrated into an object in accordance with an example.
Figure 11D:
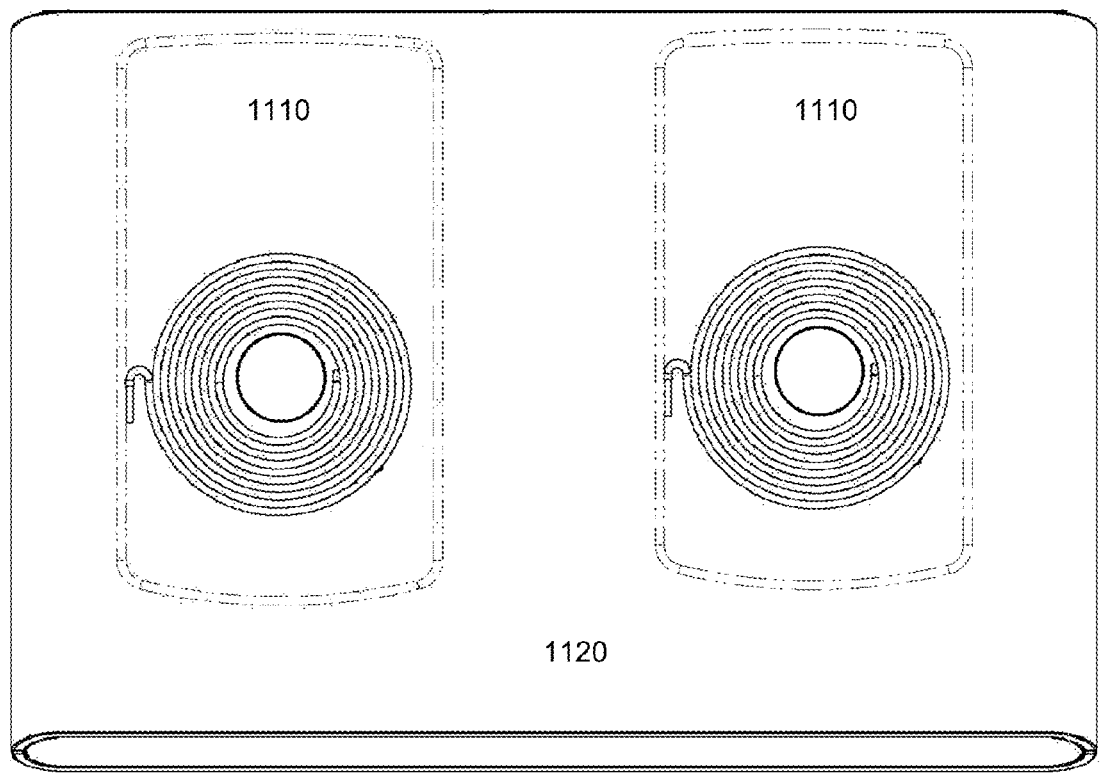
FIG. 11d depicts a plurality of wireless transfer stations integrated into an object in accordance with an example.

FIG. 11*c* illustrates one exemplary embodiment of the wireless transfer station 1110 integrated into an object 1120. In one embodiment, the object 1120 that the wireless transfer station 1110 can be integrated into can be an electronic device, such as a medical device or a wireless energy battery pack. In one example, the wireless transfer station 1110 can be integrated into a medical infusion pump and provide energy to the medical infusion pump. In another embodiment, the object 1120 can be integrated into a medical cart (such as a work surface of the medical cart), a floor mat, a floor surface, a plate mounted to a wall, a wall surface, chair railing, a room railing, a ceiling tile, a ceiling surface, and so forth. FIG. 11*d* illustrates that a plurality of wireless transfer stations 1110 can be integrated into an object 1120. FIG. 5*d* is the same as FIG. 5*c* in all other aspects.

Figure 12:
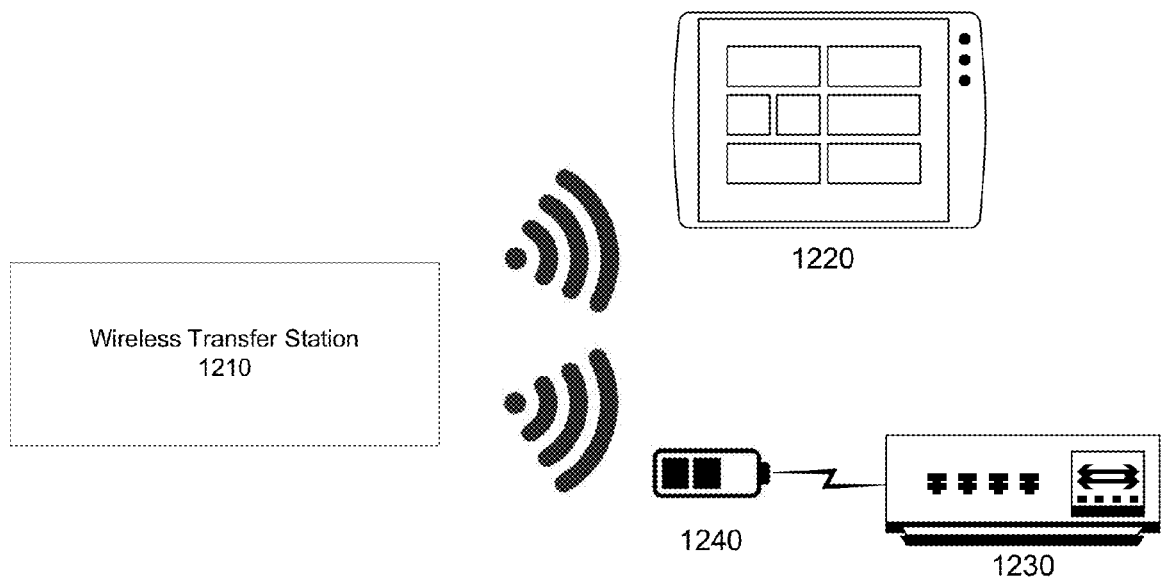
FIG. 12 depicts a wireless transfer station that can provide energy to one or more non-wire powered electronic devices or one or more recharge batteries coupled to a device in accordance with an example.

FIG. 12 shows a wireless transfer station 1210 that can provide energy to one or more non-wire powered electronic devices 1220 and/or one or more rechargeable batteries 1240 coupled to a device 1230. In another embodiment, the wireless transfer station 1210 can provide energy to different types of non-wire powered electronic devices, such as a monitoring device, a computing device, a medical device, and so forth. In one example, the wireless transfer station 1210 can provide a unified energy source for the devices 1220 and 1230 and/or the one or more rechargeable batteries 1240 coupled to the device 1230. In one embodiment, a unified energy source can be a power source that can provide power to a device, a wireless transfer station, and/or a battery without using different power connectors to provide the power to the device, the wireless transfer station, and/or the battery. In one embodiment, the wireless transfer stations can include an integrated wireless energy coil and a physical electrical energy connection terminal. In another embodiment, the wireless transfer station 1210 can transfer energy via an electrical energy connection terminal and/or an integrated wireless transfer coil.

Figure 13A:
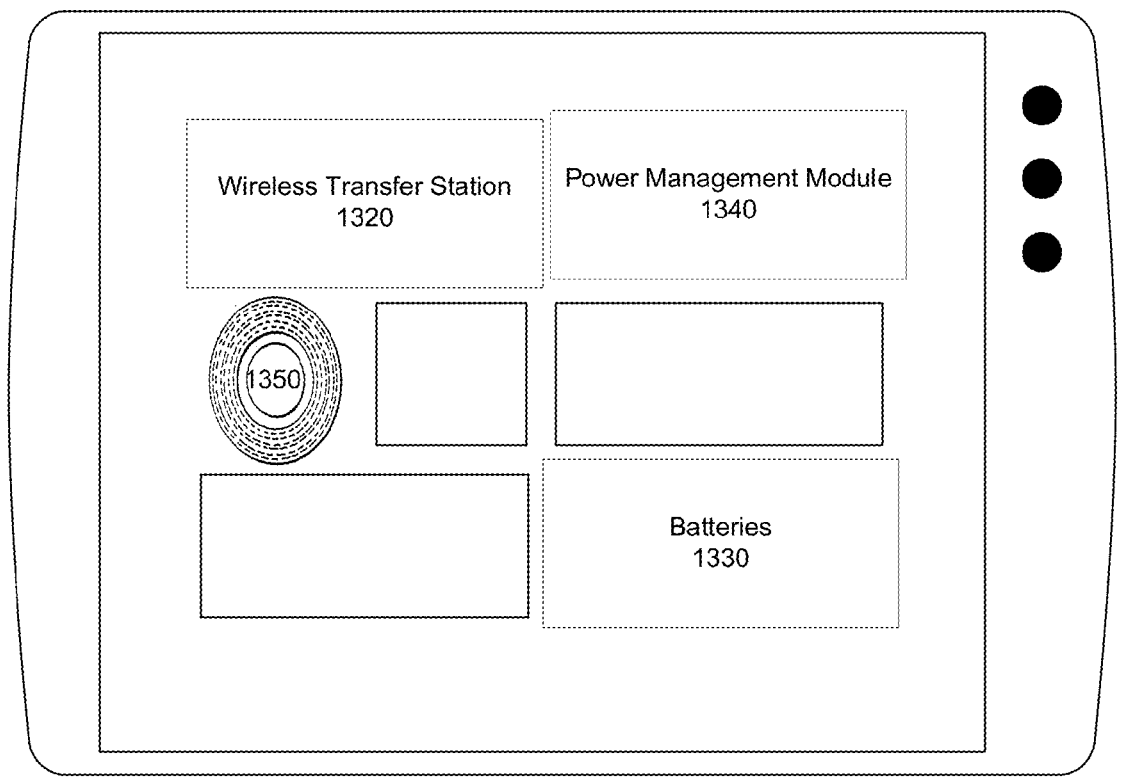
FIG. 13a depicts a device with a wireless transfer station coupled to the device or integrated into the device in accordance with an example.

FIG. 13*a* shows a device 1320 with a wireless transfer station 1320 coupled to the device 1310 or integrated into the device 1310. In one embodiment, the wireless transfer station 1320 can be configured to provide energy to batteries 1330 of the device 1310 and the batteries 1330 can provide energy to the device 1310. In another embodiment, the wireless transfer station 1320 can be configured to provide energy directly to the device 1310, e.g. without using batteries. In one example, a power management module 1340 can provide energy directly to the device 1310 by receiving energy at a wireless transfer coil 1350 of the wireless transfer station 1310 from a wireless transfer coil of another wireless transfer station and direct the energy via the power management module 1340 to the device 1310 and/or the batteries 1330.

Figure 13B:
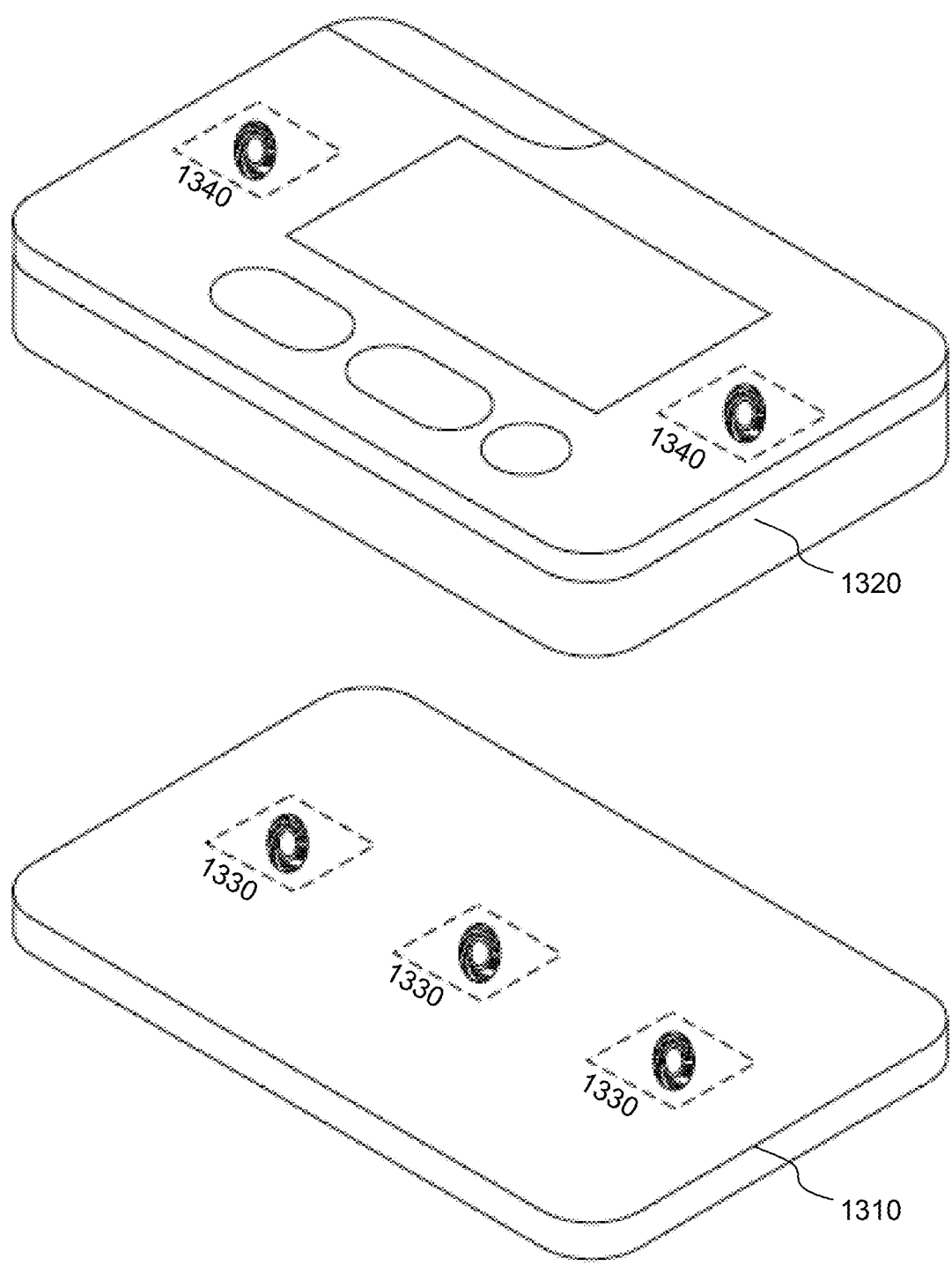
FIG. 13b depicts a wireless transfer station with a plurality of wireless transfer coils configured to transfer energy and/or data to an electronic device with one or more integrated wireless transfer stations in accordance with an example.

FIG. 13*b* illustrates a wireless transfer station 1310 with a plurality of wireless transfer coils 1330 configured to transfer energy and/or data to an electronic device 1320, such as a medical device. The medical device can include one or more integrated wireless transfer stations 1340. In one embodiment, the electronic device 1320 can be located adjacent to the wireless transfer station 1310. For example, a bottom surface of the electronic device 1320 can abut a top surface of the wireless transfer station 1310.

Figures 14A, 14B, 14C:
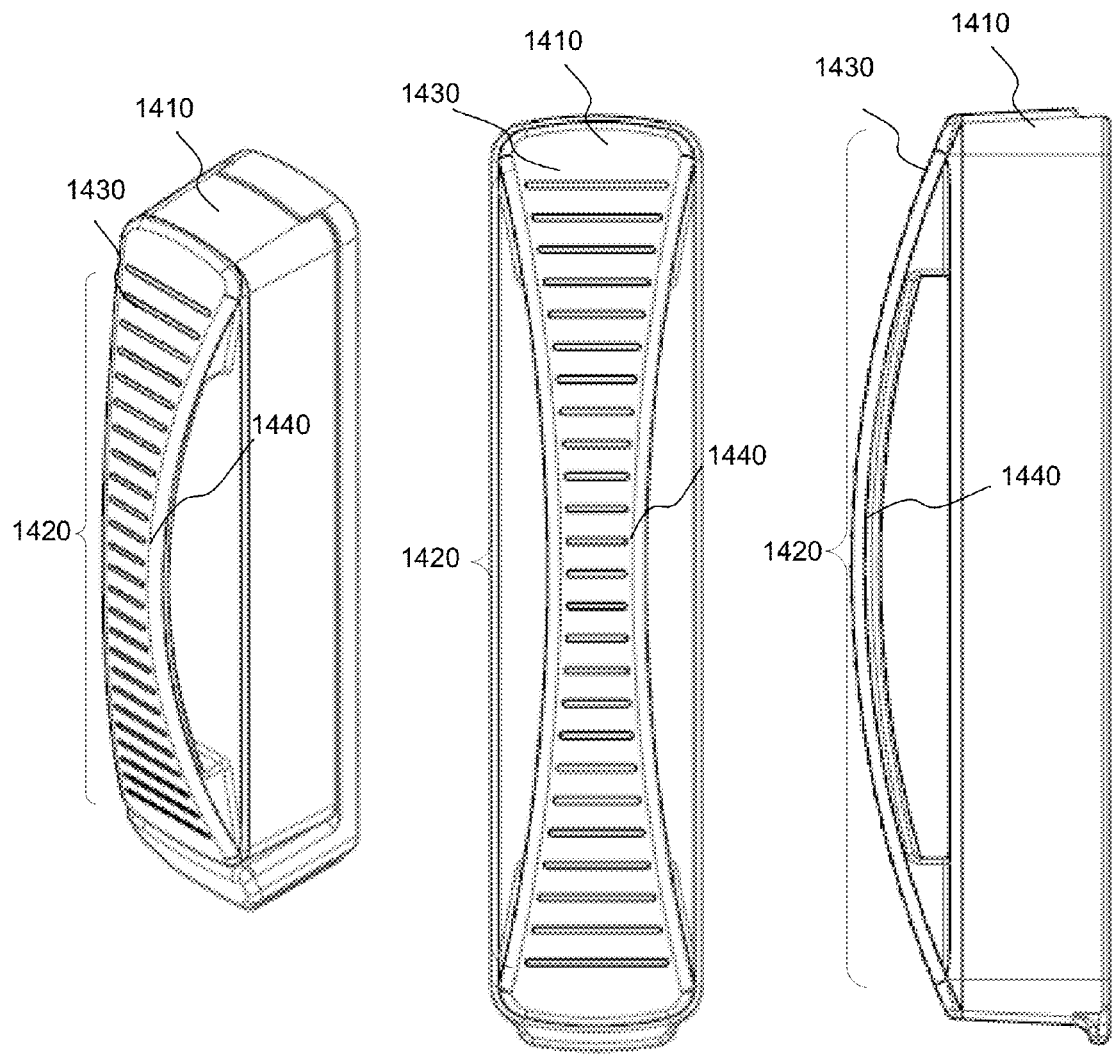
FIG. 14a depicts a perspective view of the wireless transfer station with display in accordance with an example.
FIG. 14b depicts a front view of the wireless transfer station with display in accordance with an example.
FIG. 14c depicts a side view of the wireless transfer station with display in accordance with an example.

FIGS. 14*a*, 14*b*, and 14*c* show a wireless transfer station 1410 with a display 1420. FIG. 14*a* shows a perspective view of the wireless transfer station 1410 with display 1420. FIG. 14*b* shows a front view of the wireless transfer station 1410 with display 1420. FIG. 14*c* shows a side view of the wireless transfer station 1410 with display 1420. FIGS. 14*a*, 14*b*, and 14*c* provide different views of the wireless transfer station 1410 with the display 1420 and the wireless transfer station 1410 and the display 1420 shown in FIGS. 14*a*, 14*b*, and 14*c* are the same in all other regards. In one embodiment, FIGS. 14*a*, 14*b*, and 14*c* show a display 1420 that can include one or more lighting sources 1430, such as light emitting diodes (LEDs), that can be integrated into the battery pack handle 1440 to indicate an energy level of the wireless transfer station 1410. In one embodiment, the display 1420 can indicate the energy level information of the wireless transfer station 1410 in selected increments, such as 5 percent energy level increments. In one example, the display 1420 can have 20 LEDs 1430 integrated into the wireless transfer station 1410 handle that can provide 5 percent energy level increment indications. In this example, when the wireless transfer station 1410 is at a full energy level, the 20 LEDs 1430 integrated into the handle 1440 of the wireless transfer station 1410 can each be illuminated. As the energy level of the wireless transfer station 1410 decreases, the 20 LEDs 1430 integrated into the handle 1440 can sequentially stop illuminating as the wireless transfer station 1410 decreases in energy at 5 percent increments.

In one embodiment, a brightness level, an illumination level, and/or the color of the one or more lighting sources integrated into the handle 1440 can be adjusted by the wireless transfer station 1410 based on selected illumination criteria. In one example, the selected illumination criteria can include a time of day, a location of the wireless transfer station 1410, a type of device that the wireless transfer station 1410 is attached to, a current energy level of the wireless transfer station 1410, when the wireless transfer station 1410 is receiving a charge, when the wireless transfer station 1410 is transferring energy, and so forth. In another example, the display 1420 can be a night light to indicate the location of the wireless transfer station 1410 during low light conditions and/or provide illuminating light to a surrounding environment during low light conditions.

In one embodiment, an optically viewable portion (as discussed in the preceding paragraphs) of the wireless transfer station 1410 can be located at a selected location on the handle 1440 with the display 1420 located beneath the optically viewable portion. In another embodiment, the display 1420 can be flush with an exterior surface of the wireless transfer station 1410 and can be located at a selected location on the handle 1440.

In one embodiment, one or more of the displays of a wireless transfer station can be a liquid crystal display (LCD), a resistive LCD display, a capacitive LCD display, a light emitting diode (LED) display, a liquid crystal on silicon (LCOS) display, an organic LED (OLED) display, an active-matrix OLED (AMOLED) display, a touch screen display, a haptic display, and/or a tactile display. In another embodiment, the one or more displays can be configured to display one or more colors, such as different colors based on the selected energy information.

Figure 15:
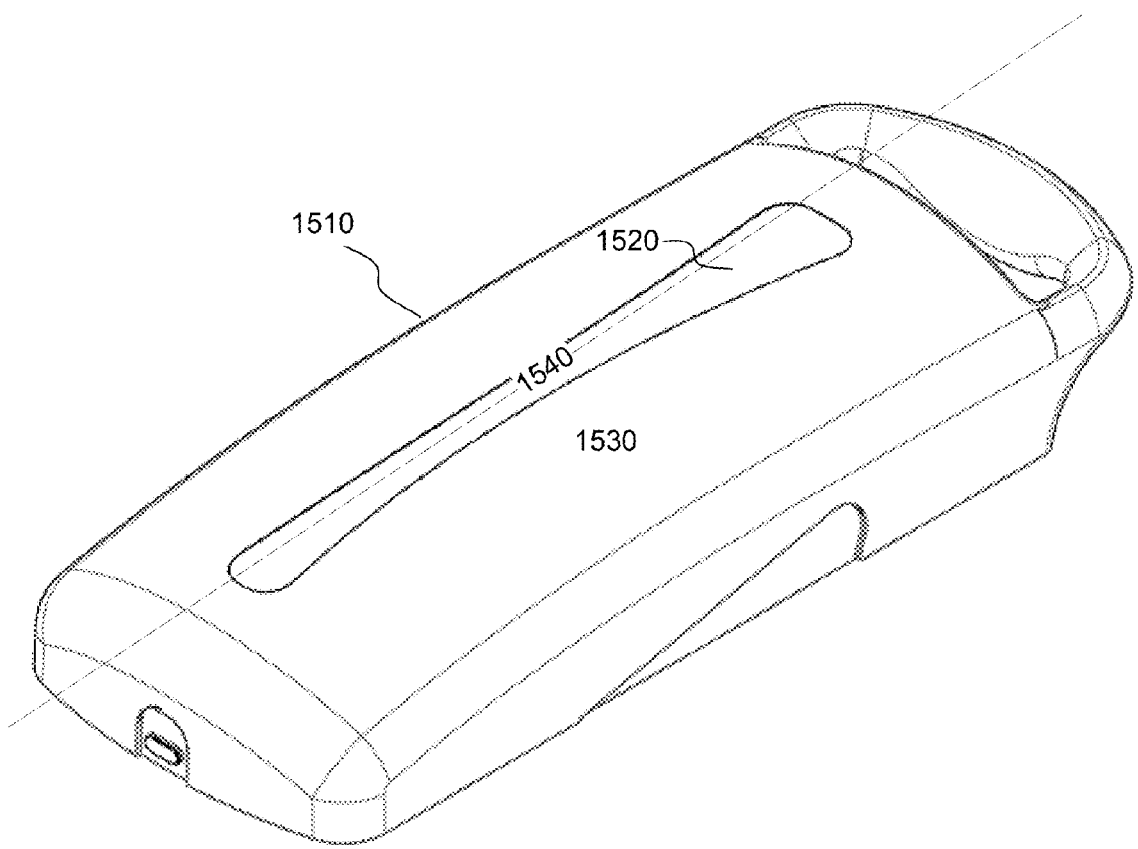
FIG. 15 depicts a top perspective view of the wireless transfer station with display in accordance with an example.

FIG. 15 shows a top perspective view of the wireless transfer station 1510 with display 1520. In one embodiment, the display 1520 that can include one or more lighting sources, such as a liquid crystal display (LCD), that can be integrated into an outer surface 1530 of the wireless transfer station 1510 to indicate selected information of the wireless transfer station 1510. In another embodiment, the display 1520 can run along a portion of a vertical axis 1540 of the wireless transfer station 1510. In another embodiment, the display 1520 can be substantially flush with the outer surface 1530 and form a hermetic seal with the outer surface 1530.

Figure 16:
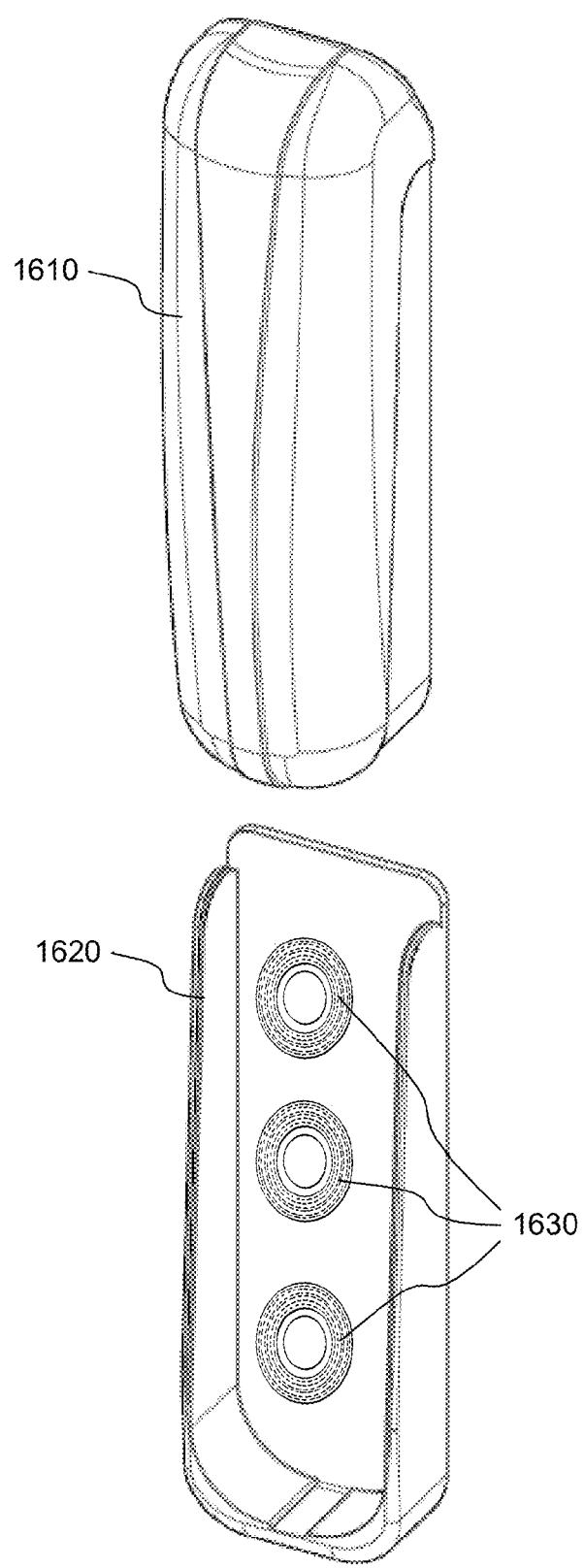
FIG. 16 depicts a side perspective view of a wireless transfer station and a receptacle in accordance with an example.

FIG. 16 shows a side perspective view of a wireless transfer station 1610 and a receptacle 1620. In one embodiment, the receptacle 1620 can include one or more wireless transfer coils 1630 used to transfer energy between a wireless transfer station 1610 and the receptacle 1620, a device, or another wireless transfer station. In one embodiment the receptacle 1620 can be shaped and formed to align one or more wireless transfer coils of the wireless transfer station 1610 with the one or more wireless transfer coils 1630 of the receptacle 1620. In one embodiment, the receptacle 1620 can be shaped and formed to receive wireless transfer stations of different shapes and/or sizes and align one or more wireless transfer coils of the wireless transfer stations of different shapes and/or sizes with the one or more wireless transfer coils 1630 of the receptacle 1620. In one embodiment the receptacle 1620 can be integrated into another wireless transfer station, such as a plate mounted to a wall or a floor mat.

Figure 17A:
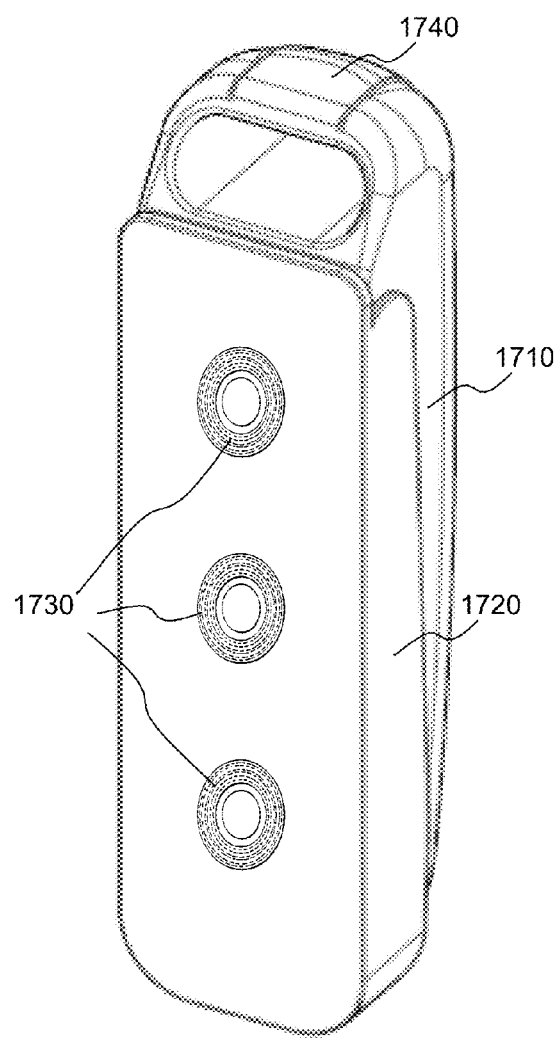
FIG. 17a depicts a wireless transfer station with a handle in accordance with an example.
Figure 17B:
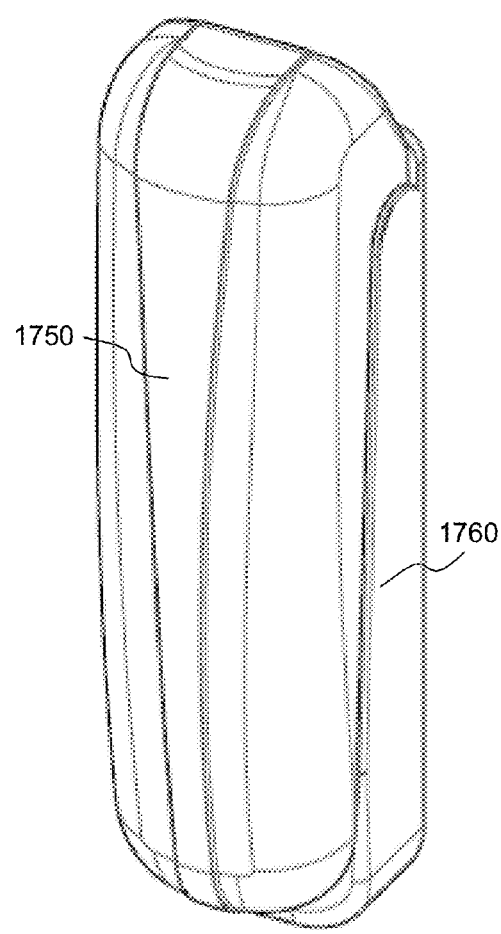
FIG. 17b depicts a side perspective view of a wireless transfer station coupled to a receptacle in accordance with an example.

FIG. 17*a* shows a back perspective view of a wireless transfer station 1710 coupled to a receptacle 1720 with one or more wireless transfer coils 1730. FIG. 17*a* further shows that the wireless transfer station 1710 can include a handle 1740. In one embodiment, the handle 1740 can be integrated into the wireless transfer station 1710 or molded into the wireless transfer station 1710. The wireless transfer station 1710 and receptacle 1720 shown in FIG. 17*a* are substantially similar to the wireless transfer station 1610 and the receptacle 1620 shown in FIG. 16 in all other aspects. FIG. 17*b* shows a side perspective view of a wireless transfer station 1750 coupled to a receptacle 1760. The wireless transfer station 1750 and receptacle 1760 shown in FIG. 17*b* are the same as the wireless transfer station 1610 and the receptacle 1620 shown in FIG. 16.

FIG. 18*a* shows a side perspective view of another wireless transfer station 1810 and a receptacle 1820. In one embodiment, the receptacle 1820 can include one or more wireless transfer coils 1830 used to transfer energy between a wireless transfer station 1810 and the receptacle 1820, a device, or another wireless transfer station. In one embodiment the receptacle 1820 can be shaped and formed to align one or more wireless transfer coils of the wireless transfer station 1810 with the one or more wireless transfer coils 1830 of the receptacle 1820. In one embodiment, the receptacle 1820 can be shaped and formed to receive wireless transfer stations of different shapes and/or sizes and align one or more wireless transfer coils of the wireless transfer stations of different shapes and/or sizes with the one or more wireless transfer coils 1830 of the receptacle 1820. In one embodiment the receptacle 1820 can be integrated into another wireless transfer station, such as a plate mounted to a wall or a floor mat. The wireless transfer station 1810 and receptacle 1820 shown in FIG. 18*a* have a different size and shape to the wireless transfer station and the receptacle shown in FIGS. 16 and 17*b* and are the same in all other aspects. FIG. 18*b* shows a side perspective view of a wireless transfer station 1810 coupled to a receptacle 1820. The wireless transfer station 1810 and receptacle 1820 shown in FIG. 18*b* have a different size and shape to the wireless transfer station and the receptacle shown in FIGS. 16 and 17*b* and are the same in all other aspects. FIG. 18*c* shows a back perspective view of a wireless transfer station 1840 coupled to a receptacle 1850. FIG. 18*c* further shows that the wireless transfer station 1840 can include a handle 1870. In one embodiment, the handle 1870 can be integrated in to the wireless transfer station 1870. In one embodiment, the receptacle 1850 can include one or more wireless transfer coils 1860 used to transfer energy between a wireless transfer station 1840 and the receptacle 1850, a device, or another wireless transfer station. The wireless transfer station 1840 and receptacle 1850 shown in FIG. 18*c* have a different size and shape to the wireless transfer station and the receptacle shown in FIG. 17*a* and are the same in all other aspects.

Figure 19B:
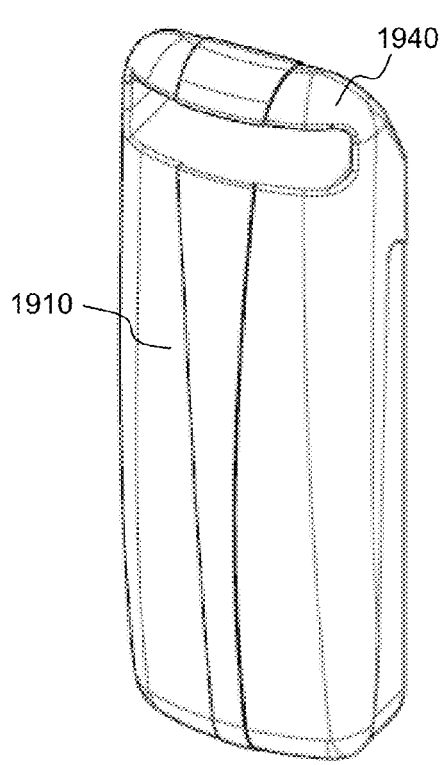
FIG. 19b depicts another side perspective view of wireless transfer station and a receptacle in accordance with an example.
Figure 19B:
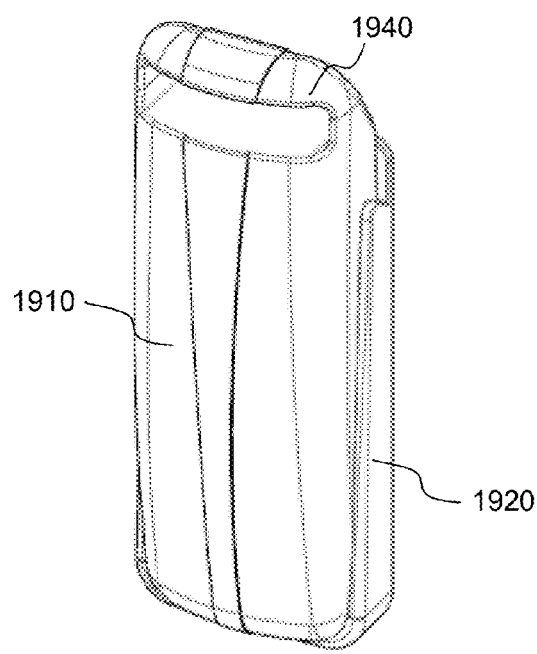
Figure 19A:
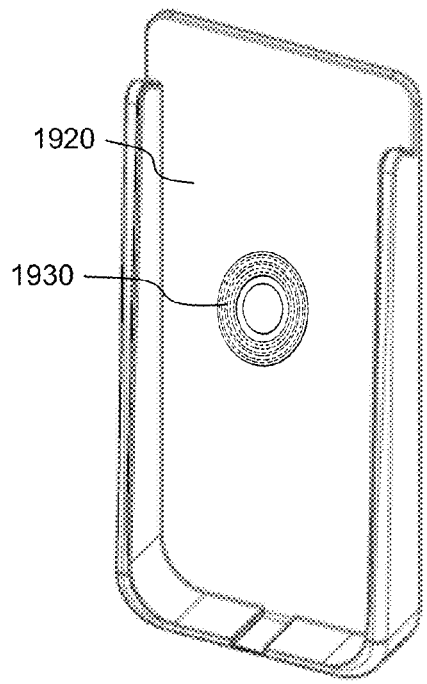
FIG. 19a depicts a side perspective view of wireless transfer station and a receptacle in accordance with an example.

FIG. 19*a* shows a side perspective view of a wireless transfer station 1910 and a receptacle 1920. In one embodiment, the wireless transfer station 1910 can include a handle 1940. In one embodiment, the handle 1940 can be integrated into the wireless transfer station 1910. In one embodiment, the receptacle 1920 can include one or more wireless transfer coils 1930 used to transfer energy between a wireless transfer station 1910 and the receptacle 1920, a device, or another wireless transfer station. In one embodiment the receptacle 1920 can be shaped and formed to align one or more wireless transfer coils of the wireless transfer station 1910 with the one or more wireless transfer coils 1930 of the receptacle 1920. In one embodiment, the receptacle 1920 can be shaped and formed to receive wireless transfer stations of different shapes and/or sizes and align one or more wireless transfer coils of the wireless transfer stations of different shapes and/or sizes with the one or more wireless transfer coils 1930 of the receptacle 1920. In one embodiment the receptacle 1920 can be integrated into another wireless transfer station, such as a plate mounted to a wall or a floor mat.

Figure 19C:
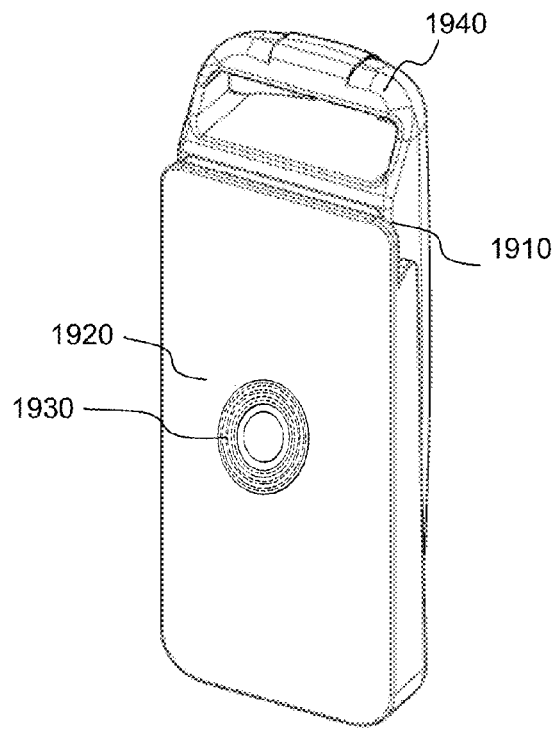
FIG. 19c depicts a back perspective view of a wireless transfer station with a handle coupled to a receptacle in accordance with an example.
Figure 19D:
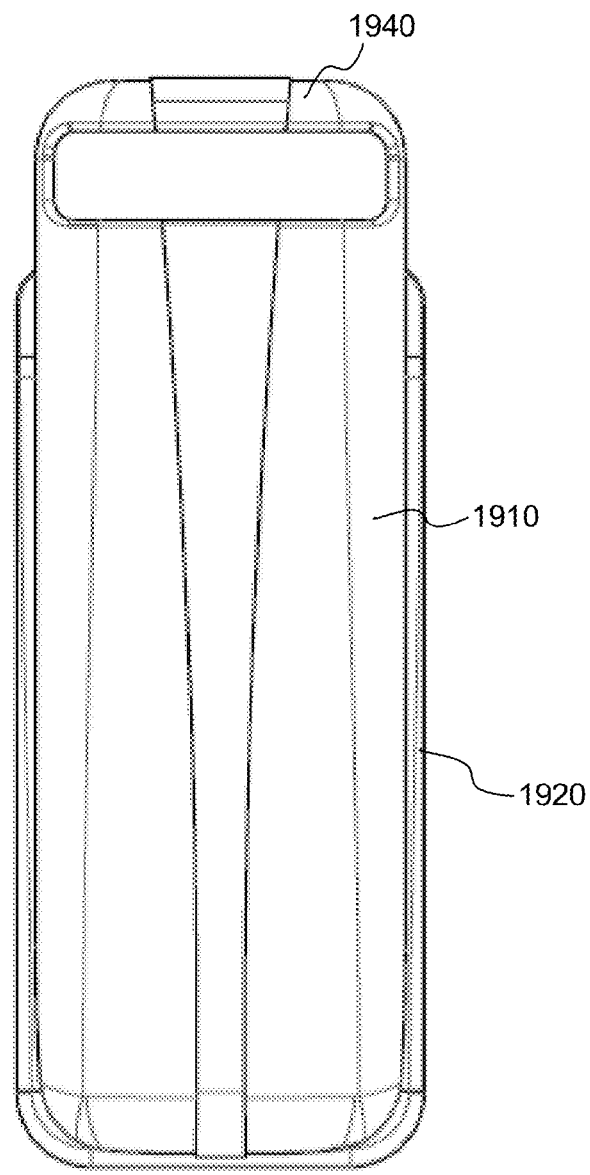
FIG. 19d depicts a front perspective view of a wireless transfer station with a handle coupled to a receptacle in accordance with an example.
Figure 19E:
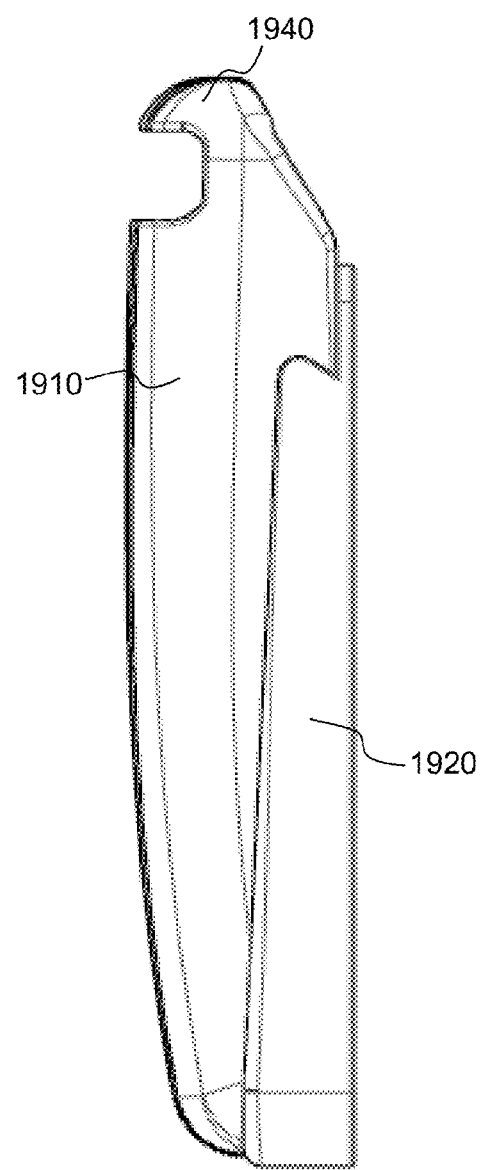
FIG. 19e depicts another side perspective view of a wireless transfer station with a handle coupled to a receptacle in accordance with an example.

FIG. 19*b* shows a side perspective view of a wireless transfer station 1910 with a handle 1940 coupled to a receptacle 1920. The wireless transfer station 1910 and receptacle 1920 shown in FIG. 19*b* is the same as the wireless transfer station 1910 and receptacle 1920 shown in FIG. 19*a*. FIG. 19*c* shows a back perspective view of a wireless transfer station 1910 with a handle 1940 coupled to a receptacle 1920. In one embodiment, the receptacle 1910 can include one or more wireless transfer coils 1930 used to transfer energy between a wireless transfer station 1910 and the receptacle 1920, a device, or another wireless transfer station. The wireless transfer station 1910 and receptacle 1920 shown in FIG. 19c is the same as the wireless transfer station 1910 and receptacle 1920 shown in FIGS. 19a and 19b. FIG. 19d shows a front perspective view of a wireless transfer station 1910 with a handle 1940 coupled to a receptacle 1920. The wireless transfer station 1910 and receptacle 1920 shown in FIG. 19d is the same as the wireless transfer station 1910 and receptacle 1920 shown in FIGS. 19a, 19b, and 19c. FIG. 19e shows a side perspective view of a wireless transfer station 1910 with a handle 1940 coupled to a receptacle 1920. The wireless transfer station 1910 and receptacle 1920 shown in FIG. 19e is the same as the wireless transfer station 1910 and receptacle 1920 shown in FIGS. 19a, 19b, 19c, and 19d.

Figure 20B:
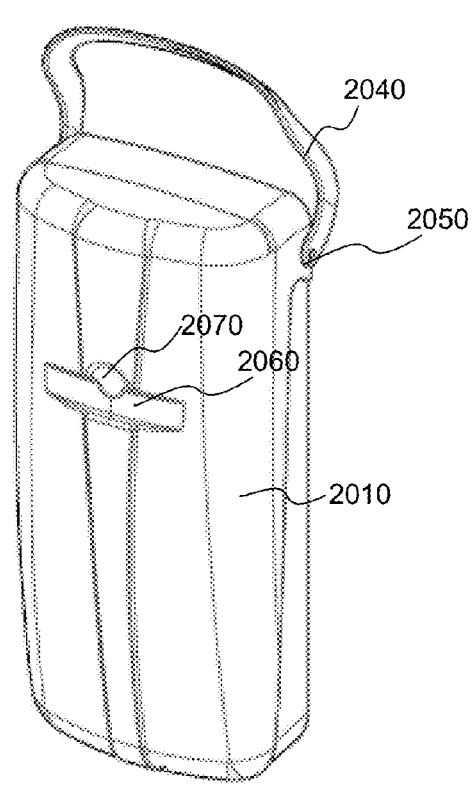
FIG. 20b depicts a side perspective view of a wireless transfer station and a receptacle in accordance with an example.
Figure 20B:
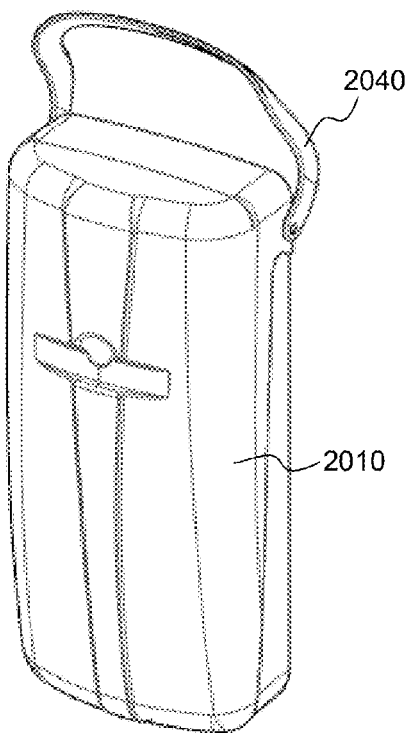
Figure 20A:
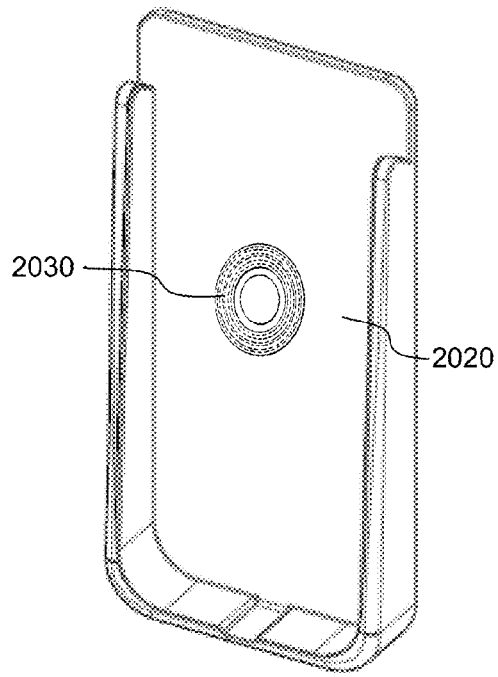
FIG. 20a depicts a side perspective view of a wireless transfer station and a receptacle in accordance with an example.
Figure 20C:
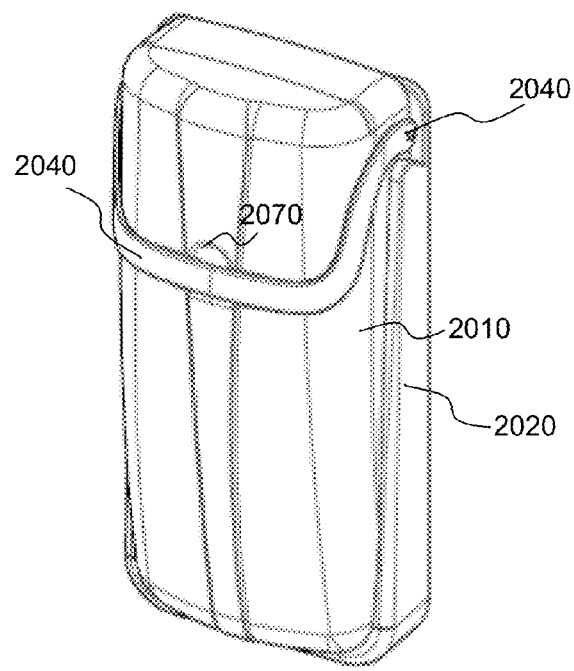
FIG. 20c depicts a side perspective view of a wireless transfer station with a handle coupled to a receptacle in accordance with an example.

FIG. 20a shows a side perspective view of wireless transfer station 2010 and a receptacle 2020. In one embodiment, the wireless transfer station 2010 can include a handle 2040. In another embodiment, the handle 2040 can rotate on a hinge 2050 to enable the handle 2040 to move between a plurality of positions. In one example, the handle can rotate on the hinge 2050 to an open position for lifting or carrying, as shown in FIG. 20a. In another example, the handle can rotate on the hinge 2050 to a closed position for a compact form for use, as shown in FIG. 20c and discussed in the proceeding paragraphs. In another embodiment, the wireless transfer station 2010 can include a handle receiver 2060 to receive the handle 2040 when the handle 2040 is in a closed position. In another embodiment, the handle receiver 2060 can be a recess or a cavity in an outer surface of the wireless transfer station 2010 to enable the handle 2040 to be substantially flush with the remainder of the outer surface of the wireless transfer station 2010. In another embodiment, the handle receiver 2060 can include a lifting recess 2070 configured to enable a user of the wireless transfer station 2010 to lift or grasp the handle 2040 when the handle 2040 is in a closed position. In one example, when the handle 2040 is in a closed position, the user can slide a finger into the lifting recess 2070 and lift the handle 2040 to move the handle to an open position. One advantage of the hinge handle 2040 with the handle receiver 2060 is that the handle 2040 is compact and substantially seamless with the outer surface of the wireless transfer station 2010 when the handle is in a closed position and provides a user a handle to lift or carry the wireless transfer station 2010 when the handle is in an open position.

FIG. 20a further shows the receptacle 2020 can include one or more wireless transfer coils 2030 used to transfer energy between a wireless transfer station 2010 and the receptacle 2020, a device, or another wireless transfer station. In one embodiment the receptacle 2020 can be shaped and formed to align one or more wireless transfer coils of the wireless transfer station 2010 with the one or more wireless transfer coils 2030 of the receptacle 2020. In one embodiment, the receptacle 2020 can be shaped and formed to receive wireless transfer stations of different shapes and/or sizes and align one or more wireless transfer coils of the wireless transfer stations of different shapes and/or sizes with the one or more wireless transfer coils 2030 of the receptacle 2020. In one embodiment the receptacle 2020 can be integrated into another wireless transfer station, such as a plate mounted to a wall or a floor mat.

FIG. 20b shows a side perspective view of a wireless transfer station 2010 with a handle 2040. The wireless transfer station 2010 shown in FIG. 33b is the same as the wireless transfer station 2010 shown in FIG. 20a. FIG. 20c shows a side perspective view of a wireless transfer station 2010 with a handle 2040 coupled to a receptacle 2020. The wireless transfer station 2010 and receptacle 2020 shown in FIG. 20c is the same as the wireless transfer station 2010 and receptacle 2020 shown in FIGS. 20a and 20b.

Figure 21:
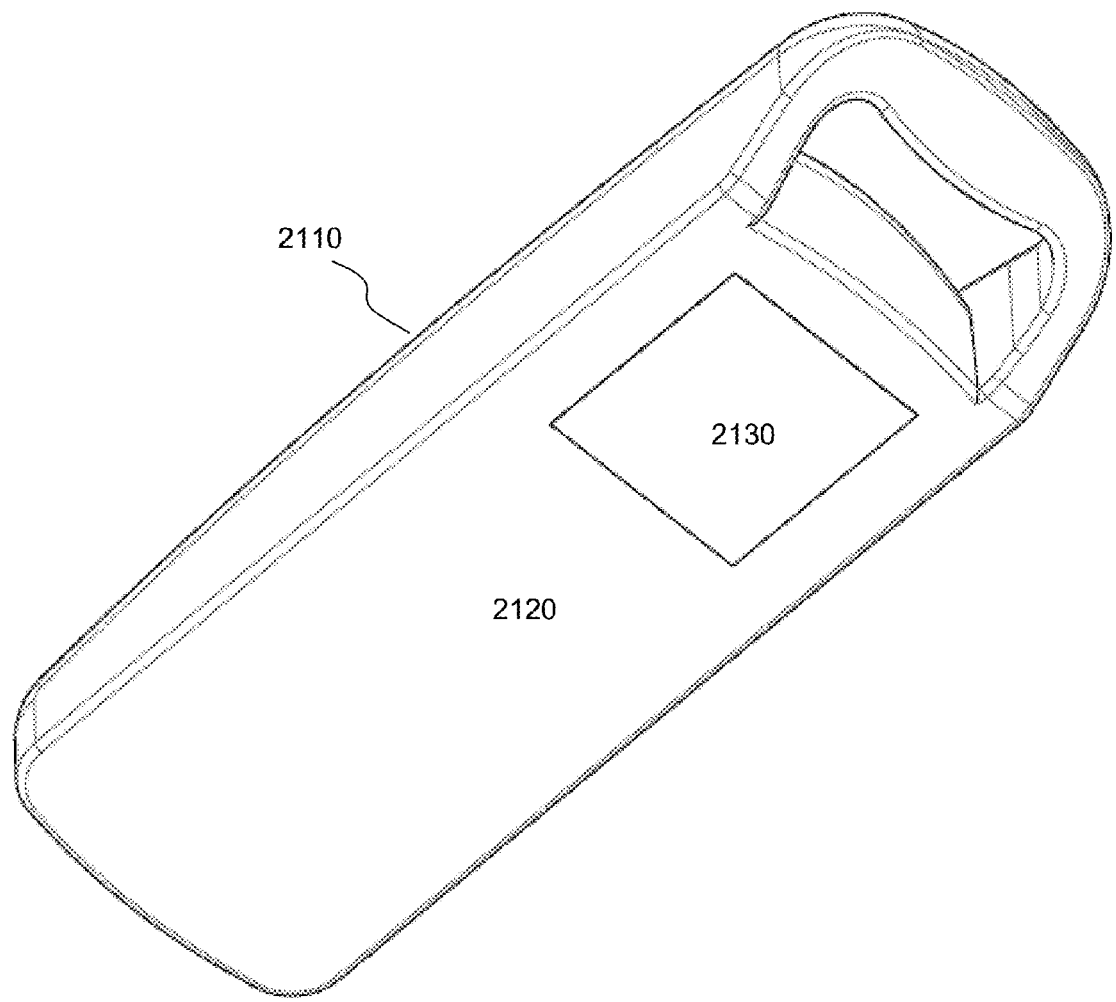
FIG. 21 depicts a wireless transfer station with an outer surface in accordance with an example.

FIG. 21 shows a wireless transfer station 2110 with an outer surface 2120. In one embodiment, the outer surface 2120 of the wireless transfer station 2110 can include a perforated label 2130 to provide for ventilation of gas when an internal pressure of the wireless transfer station 2110 exceeds a selected threshold. In one embodiment, the perforated label can be a one-way label to restrict fluids from entering the wireless transfer station 2110 and enable moisture to be wicked away or released from wireless transfer station 2110.

Figure 22A:
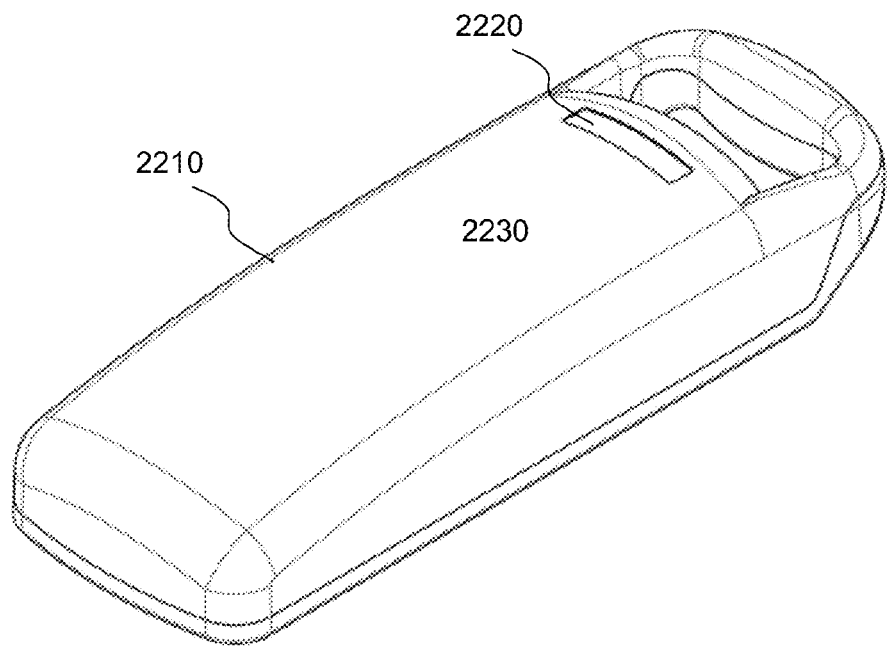
FIG. 22a depicts a top perspective view of the wireless transfer station with a display in accordance with an example.

FIG. 22a shows a top perspective view of the wireless transfer station 2210 with a display 2220. In one embodiment, FIG. 22a shows a display 2220 that can include one or more lighting sources, such as a liquid crystal display (LCD), that can be integrated into an outer surface 2230 of the wireless transfer station 2210 to indicate selected information of the wireless transfer station 2210. In one embodiment, the display 2220 can indicate the energy level information of the wireless transfer station 2210 in selected increments, such as 5 percent energy level increments. In one embodiment, the display 2220 can be substantially flush with the outer surface 2230 and form a hermetic seal with the outer surface 2230.

Figure 22B:
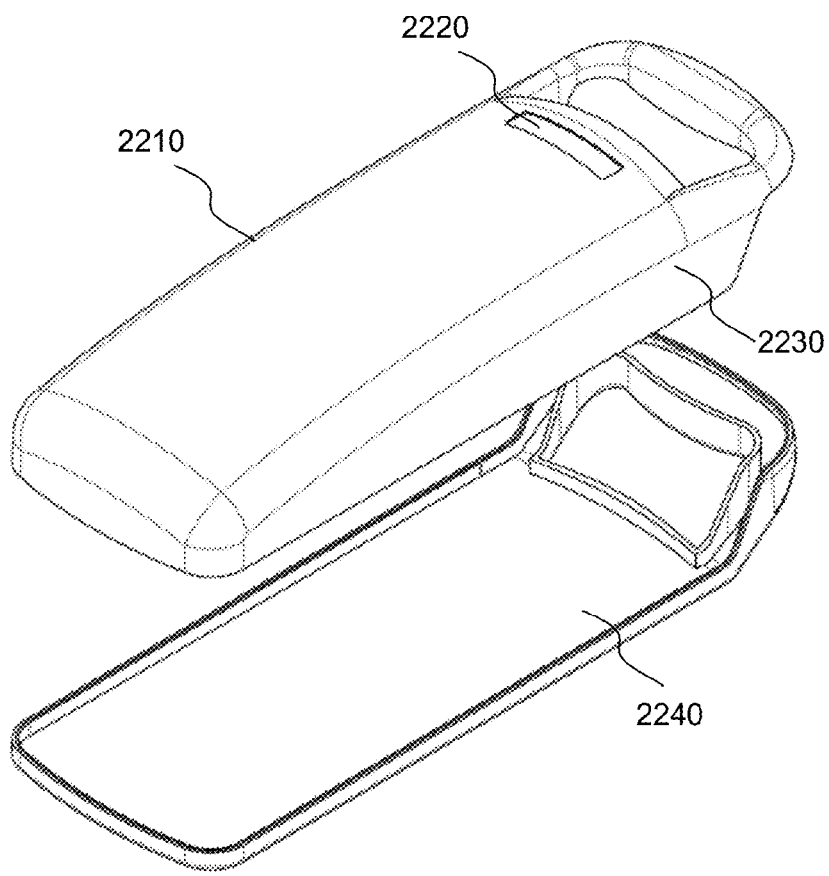
FIG. 22b depicts an exploded view of the wireless transfer station with a display in accordance with an example.

FIG. 22b shows an exploded view of the wireless transfer station 2210 with a display 2220. In one embodiment, the wireless transfer station 2210 can be a waterproof housing enclosure. In another embodiment, the wireless transfer station 2210 can be hermetically sealed. In one example, the wireless transfer station 2210 can be hermetically sealed by placing wireless transfer station components, such as battery energy cells, a power management module, and/or a wireless transfer coil in the wireless transfer station 2210 and sealing a top piece 2230 and a bottom piece 2240 together. In another embodiment, the wireless transfer station 2210 can include more than two pieces that can be sealed together.

In one embodiment, the battery pack case can provide for outgassing of a battery. In an example of lead acid batteries, when a battery is being charged, e.g. the battery is under charge, a charge current can be greater than the current needed to maintain a full state of charge because of chemical inefficiencies of electrolytes and an internal resistance of battery cells. The level of charge current can create an excess of charged electrolytes in water with an electrolyte mix of sulfuric acid. The charged electrolytes can free hydrogen and oxygen from the water. In one embodiment, the battery pack case can outgas the hydrogen and/or oxygen from the battery pack case. In one embodiment, the battery pack case can include ventilation to emit the free hydrogen and oxygen from the battery to prevent an accumulation of hydrogen and/or oxygen. In one embodiment, the battery pack case can include one or more internal air gaps to provide internal ventilation for gas released from one or more battery cells. In another embodiment, the battery pack case can also include one or more vents to release gas from one or more battery cells or the internal air gaps to the exterior of the battery pack.

In one embodiment, the battery pack case can include an escape valve to vent gas. In another embodiment, the battery pack case can include a one-way valve or disc to release gas or pressure while maintaining a hermetic seal. In another embodiment, the battery pack case can include a perforated label to provide for ventilation of gas when an internal pressure of the battery pack case exceeds a selected threshold. In one embodiment, the perforated label can be a one-way label to restrict fluids from entering the battery pack case and enable moisture to be wicked away or released from the battery pack case. In one embodiment, the battery pack can include a moisture detection module configured to detect when moisture within the battery pack case exceeds a selected level. In one embodiment, the battery pack case can include a label which includes one or more weakened areas of the label to enable the label to expel gas and/or pressure when the internal pressure exceeds a selected threshold while maintaining a hermetic seal.

Figure 23A:
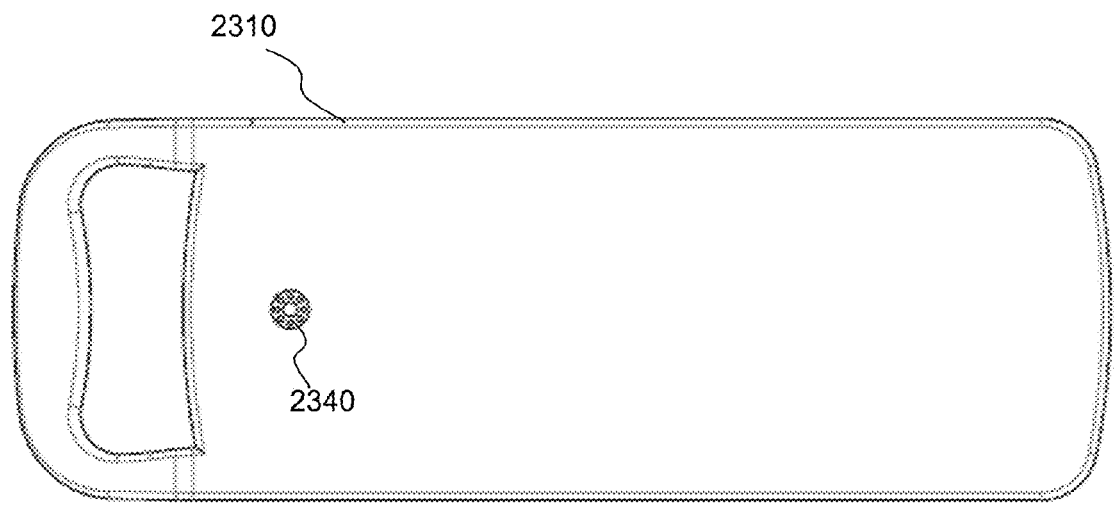
FIG. 23a depicts a top perspective view of the wireless transfer station with a pressure relief valve in accordance with an example.

FIG. 23a shows a top perspective view of the wireless transfer station 2310 with a pressure relief valve 2340. In one embodiment, the wireless transfer station 2310 can include a pressure relief valve 2340 or an escape valve to vent gas. In another embodiment, the battery pack case can include a one-way valve or disc to release gas or pressure while maintaining a hermetic seal.

Figure 23B:
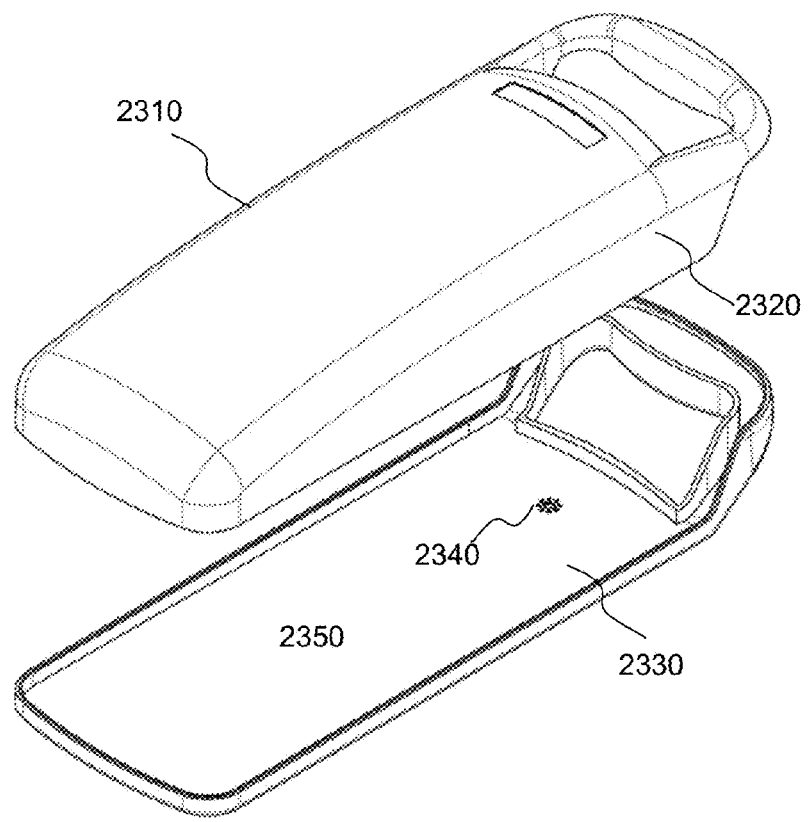
FIG. 23b depicts an exploded view of the wireless transfer station with a valve in accordance with an example.

FIG. 23b shows an exploded view of the wireless transfer station 2310 with a valve 2340. In one embodiment, the valve 2340 can be a pressure relief valve. In one embodiment, the wireless transfer station 2310 can be a waterproof housing enclosure. In another embodiment, the wireless transfer station 2310 can be hermetically sealed. In one example, the wireless transfer station 2310 can be hermetically sealed by placing wireless transfer station components, such as battery energy cells, power management module, and/or a wireless transfer coil in the wireless transfer station 2310 and sealing a top piece 2320 and a bottom piece 2330 together. In another embodiment, the wireless transfer station 2310 can include more than two pieces that can be sealed together. In another embodiment, the valve 2340 can be attached to the bottom piece 2330 or integrated into a surface 2350 of the bottom piece 2330.

Figure 23C:
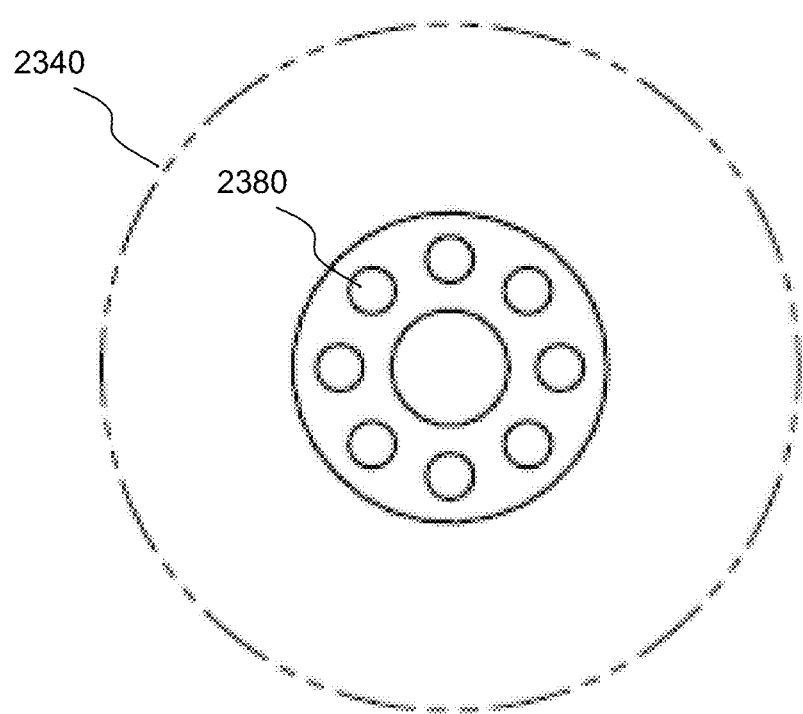
FIG. 23c depicts a top view of a valve in accordance with an example.
Figure 23D:
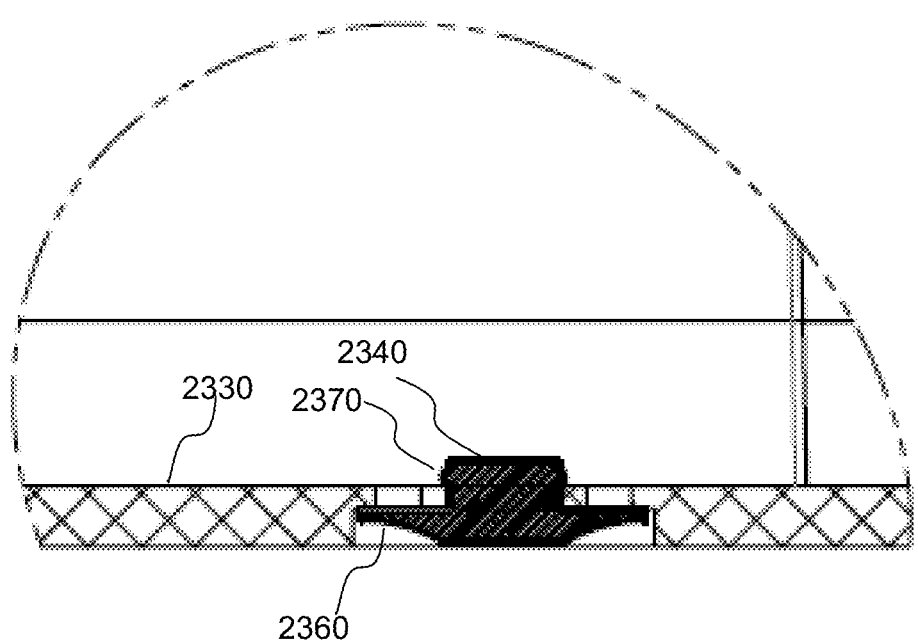
FIG. 23d depicts a side view of a valve in accordance with an example.

FIGS. 23c and 23d show one exemplary embodiment of a valve 2340, as show in FIGS. 23a and 23b. FIG. 23c shows a top view of the valve 2340. In one embodiment, the valve 2340 can be a pressure relief valve. In another embodiment, the valve 2340 can be made of rubber or other elastomeric material that is resiliently deformable. In one embodiment, a portion of the valve 2340 can include one or more openings 2380 extending through the valve 2340, such as for relieving pressure. FIG. 23d shows a side view of a valve 2340. In one embodiment, the valve 2340 can be one piece and comprise an inverted substantially umbrella-shaped or substantially dish-shaped portion 2360 that can engage inside a surface 2350 of the bottom piece 2330 of the wireless transfer station 2310 around an opening 2370.

Figure 24A:
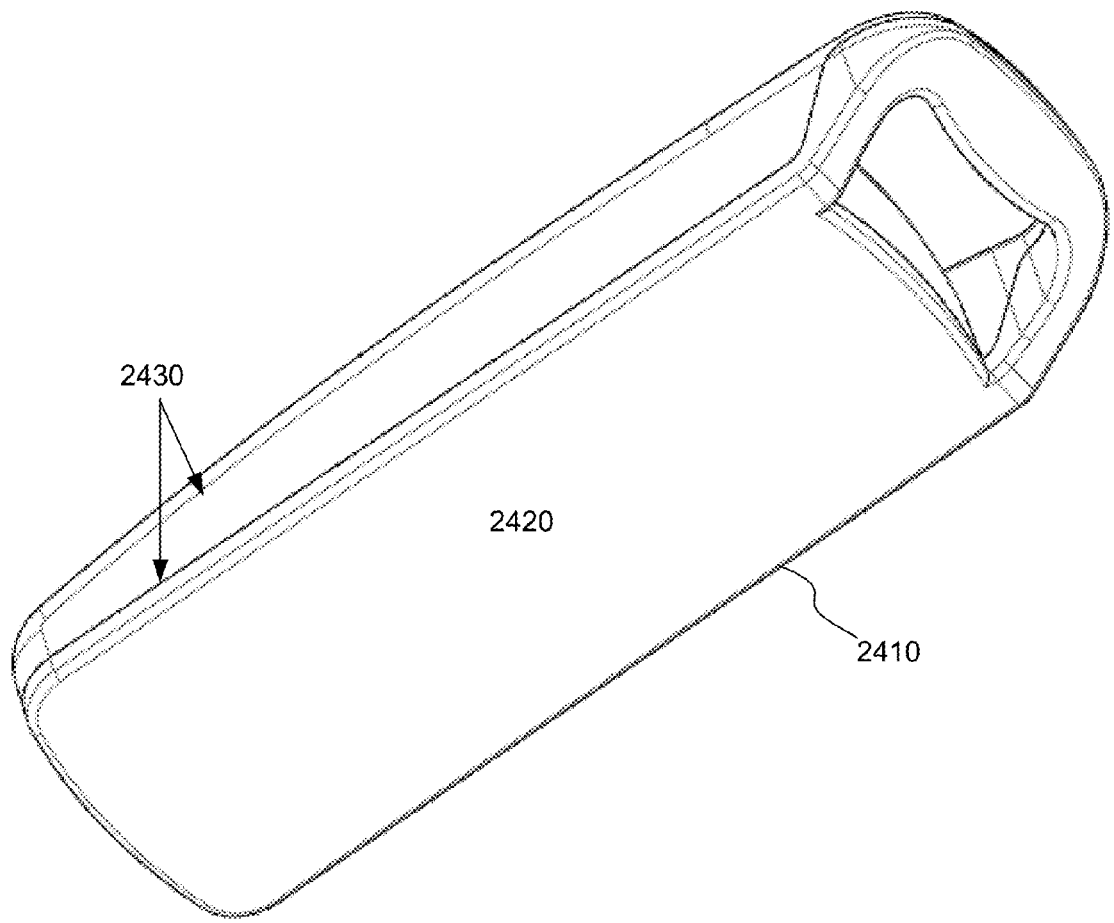
FIG. 24a depicts a bottom perspective view of the wireless transfer station with a molded seal in a seam of a wireless transfer station case in accordance with an example.
Figure 24B:
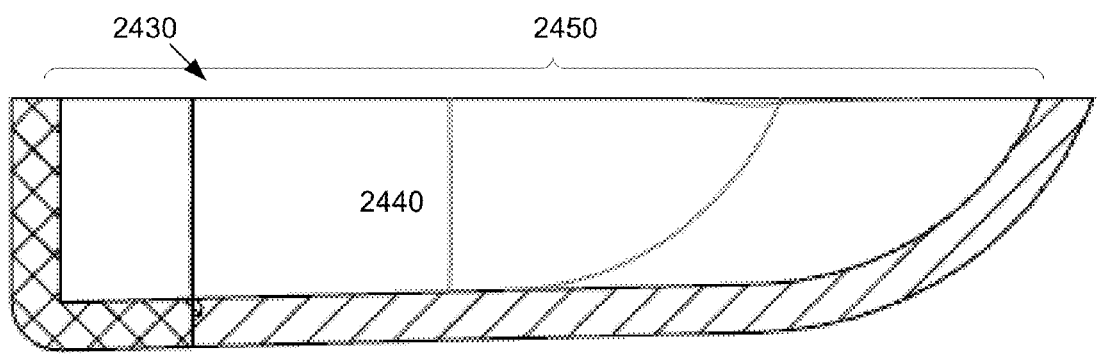
FIG. 24b depicts a seam with a gasket molded or integrated into one of the pieces of the wireless transfer station case in accordance with an example.

FIG. 24a shows a bottom perspective view of the wireless transfer station 2410 with a molded seal in a seam of a wireless transfer station case 2420. In one embodiment, the wireless transfer station case 2420 can include two or more pieces that can be sealed together, as discussed in the preceding paragraphs and shown in FIGS. 22b and 23b. In another embodiment, the wireless transfer station 2410 can be sealed using a gasket, such as a silicon over mold gasket, around one or more seams 2430 of the wireless transfer station 2410, such as exterior seams of the wireless transfer station 2410. FIG. 24b shows a seam 2430 with a gasket 2440 molded or integrated into one of the pieces of the wireless transfer station case 2420 and used to seal the wireless transfer station case 2420 when the pieces of the wireless transfer station case 2420 are put together. In one embodiment, the gasket 2440 can run along a channel 2450 of the seam 2430.

Figure 25:
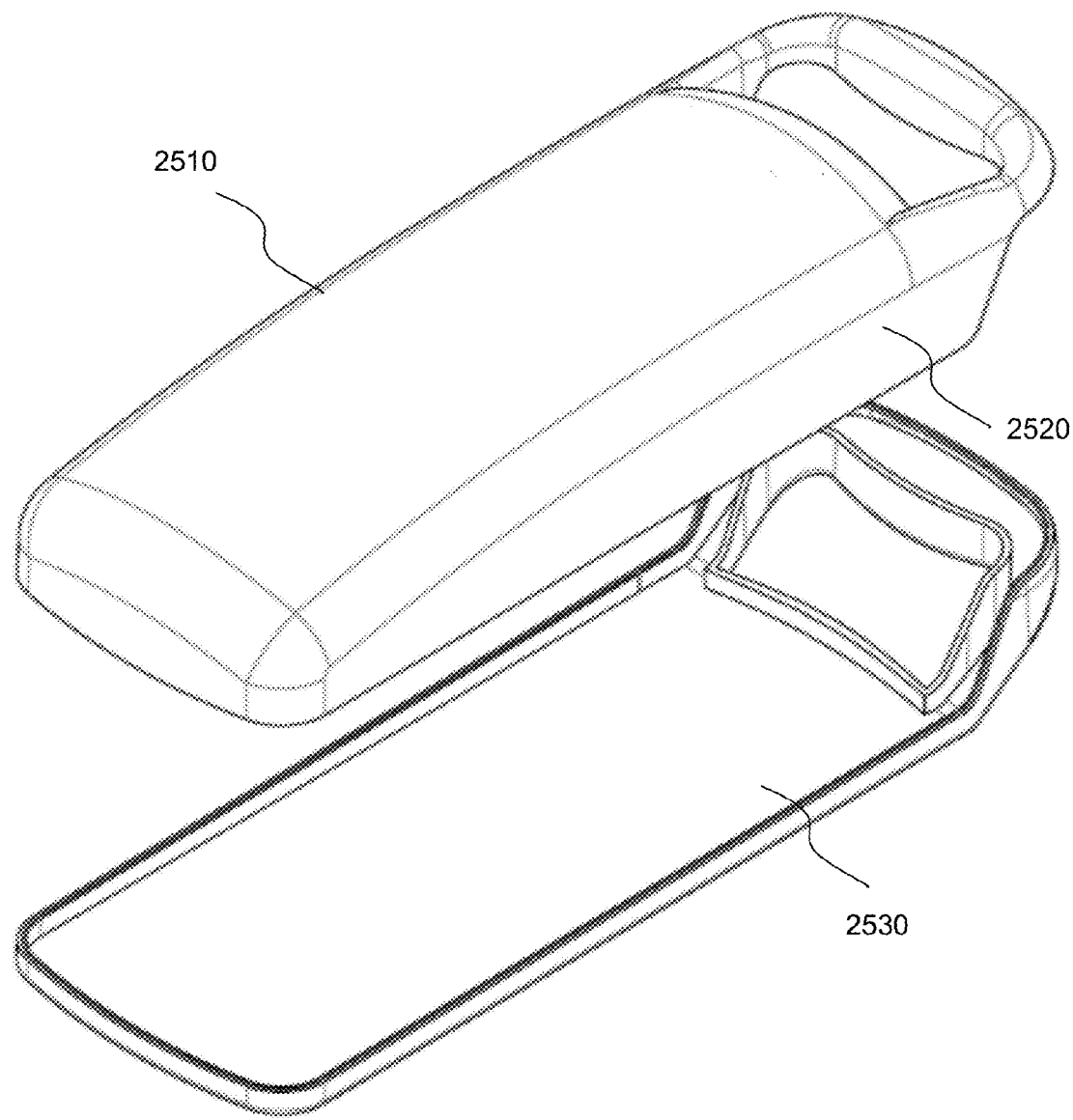
FIG. 25 depicts a wireless transfer station case in accordance with an example.

FIG. 25 shows an exploded view of a wireless transfer station 2510. In one embodiment, the wireless transfer station 2510 can be a waterproof housing enclosure. In another embodiment, the wireless transfer station 2510 can be hermetically sealed. In one example, the wireless transfer station 2510 can be hermetically sealed by placing wireless transfer station components, such as battery energy cells, a power management module, and/or a wireless transfer coil in the wireless transfer station 2510 and sealing a top piece 2520 and a bottom piece 2530 together. In another embodiment, the wireless transfer station 2510 can include more than two pieces that can be sealed together.

In one embodiment, the wireless transfer station 2510 can be a waterproof housing enclosure. In another embodiment, the wireless transfer station 2510 can be hermetically sealed by placing the battery energy cells, a power management module, and/or the wireless transfer station in the wireless transfer station 2510 and using an O-ring to seal two or more pieces, such as top piece 2520 and bottom piece 2530, of the wireless transfer station 2510 together.

Figure 26A:
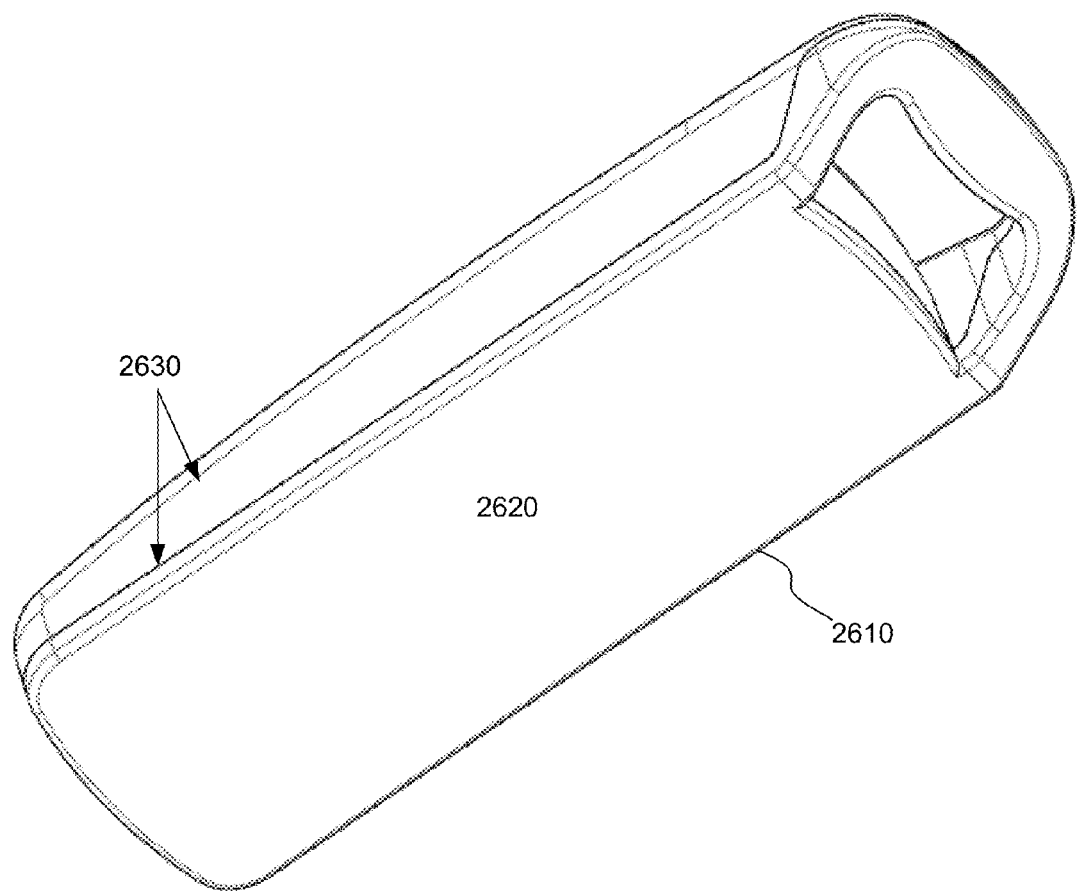
FIG. 26a depicts a bottom perspective view of the wireless transfer station with a molded seal in a seam of a wireless transfer station case in accordance with an example.

FIG. 26a shows a bottom perspective view of the wireless transfer station 2610 with a molded seal in a seam of a wireless transfer station case 2620. In one embodiment, the wireless transfer station case 2620 can include two or more pieces that can be sealed together, as discussed in the preceding paragraphs and shown in FIG. 3. In another embodiment, the wireless transfer station 2610 can be sealed using a gasket, such as a silicon over mold gasket, around one or more seams 2630 of the wireless transfer station 2610, such as exterior seams of the wireless transfer station 2610.

Figure 26B:
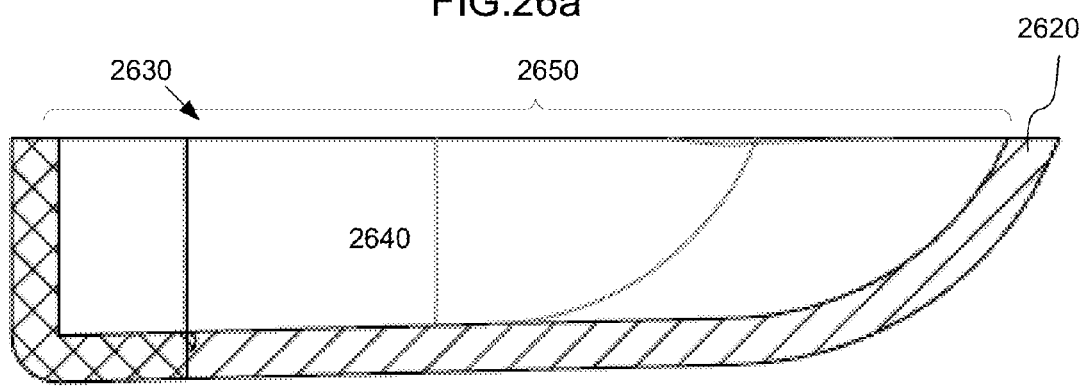
FIG. 26b depicts a seam with a gasket molded or integrated into one of the pieces of a wireless transfer station in accordance with an example.

FIG. 26b shows a seam 2630 with a gasket 2640 molded or integrated into one of the pieces of a wireless transfer station 2620 (as shown in FIG. 26a). In one embodiment, the gasket 2640 can be used to seal the wireless transfer station 2620 when a plurality of pieces of the wireless transfer station 2620 are put together. In one embodiment, the gasket 2640 can run along a channel 2650 of the seam 2630.

In one embodiment, the wireless transfer station is non-sealed or non-hermetically sealed. In another embodiment, as discussed in the preceding paragraphs, the wireless transfer station can be sealed to minimize or eliminate the adhesion and/or growth of potential pathogens or hazard materials. In another embodiment, when a wireless transfer coil is incorporated into the wireless transfer station, a need for exposed electrical connectors, exposed wires, or other unsealed portions of the battery pack can be reduced or eliminated.

One advantage of using a sealed wireless transfer station, such as a sealed a battery pack, can be to reduce or eliminate the retransmission or spreading of pathogens, such as bacterium, viruses, prion, or fungus, in a medical environment by minimizing or eliminating crevasses or seams where pathogens can adhere and/or grow. In one example, when a traditional battery pack and/or a device with an attached traditional battery pack is located in an area of a medical facility, such as a patient's room, and the traditional battery pack is moved to another area of the medical facility, such as another patient's room, pathogens adhere to surfaces of the traditional battery packs, such as at the seams or crevices and/or physical electrical contacts of the traditional battery pack. In one embodiment, the sealed wireless transfer station can reduce or eliminate the retransmission of pathogens by reducing or eliminating crevices, seams, and physical electrical contacts of the wireless transfer station. In one embodiment, the wireless transfer station can be sealed with an anti-bacterial material to reduce or eliminate the adherence of pathogens on the surface of the battery pack. In another embodiment, the wireless transfer station can be sealed or encased with waterproof and/or dustproof material.

Additionally, a traditional battery pack with electrical contacts for receiving and/or transferring energy cannot be fully cleaned because an antibacterial cleaning solution can erode the electrical contacts and/or leak into the unsealed parts of the traditional battery pack. One advantage of a sealed wireless transfer station with wireless transfer coils for transferring energy and/or data can be to enable a user to wash and/or clean the sealed wireless transfer station with antibacterial materials, such as an antibacterial cleaning solution.

In one embodiment, a case of the wireless transfer station can comprise, at least in part, of one or more antibacterial materials. In one example, the antibacterial material can be a plastic, such as a polycarbonate plastic, with a silver additive integrated into the plastic material. In another embodiment, the silver additive can kill bacteria that may adhere to the exterior surface of the wireless transfer station case. In another embodiment, the wireless transfer station case can comprise, at least in part, of ultraviolet (UV) light resilient material (such as a polycarbonate plastic or fiberglass) to enable the repeated use of UV light to kill bacteria adhering to the exterior surface of the battery pack case.

Traditional battery packs also have a risk of electrical short circuiting. In one example, a traditional battery pack has a negative energy terminal and a positive energy terminal. A conductive object that contacts both the negative energy terminal and the positive energy terminal of the traditional battery pack can cause an electrical short. Another advantage of the wireless transfer station with integrated wireless transfer coils for transferring energy can be a reduction or elimination of the risk of electrical shorting through eliminating physical electrical contacts of the wireless transfer station. In one example, the wireless transfer station with integrated wireless transfer coils can transfer energy and/or data without using physical terminal contacts and thereby eliminate traditional physical terminal contacts that cause electrical shorts.

Figure 27:
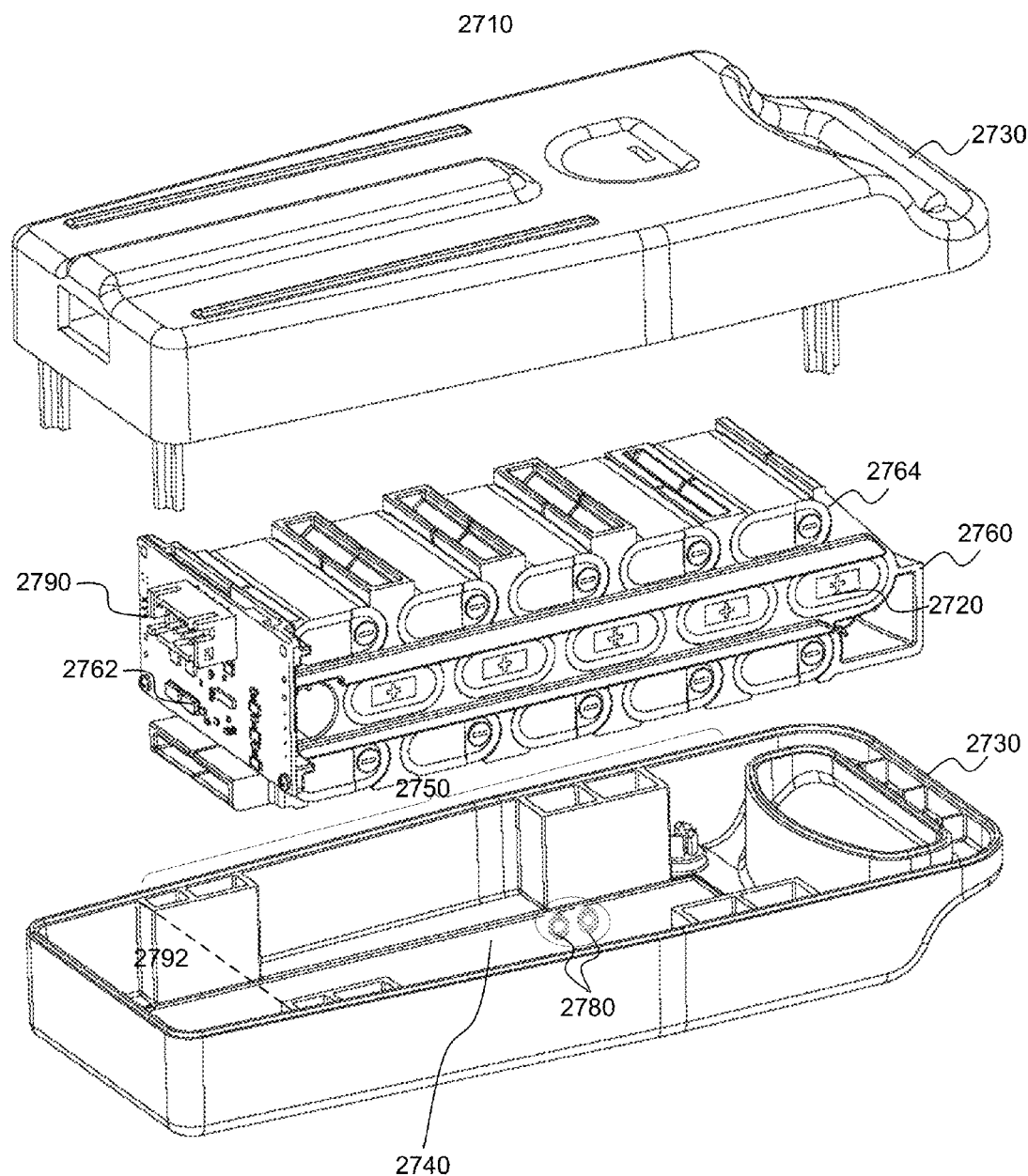
FIG. 27 depicts an exploded view of a battery pack for one or more batteries in accordance with an example.

FIG. 27 shows an exploded view of a battery pack 2710 for one or more batteries 2720. In one embodiment, the battery pack 2710 can include a battery pack housing 2730 with an inner cavity 2740. In another embodiment, the battery pack 2710 can include a battery bay 2750 located within the inner cavity 2740. In another embodiment, the battery bay 2750 can contain a plurality of individual battery cells 2720 in the battery bay 2750 and a shielding receptacle 2760. In another embodiment, the shielding receptacle 2760 can be sized and shaped to receive the plurality of individual battery cells 2720 and separate each of the plurality of individual battery cells 2720 from adjacent individual battery cells. In another embodiment, the shielding receptacle 2760 can comprise a material having a heat deflection rate of greater than 50 degrees Celsius to contain a catastrophic thermal runaway of one or more of the plurality of individual battery cells 2720.

In one embodiment, the battery pack 2710 can include a power management module 2762 configured to regulate an amount of energy received at one or more of the plurality of individual battery cells 2720 and regulate an amount of energy transferred from one or more of the plurality of individual battery cells 2720 to a device. In another embodiment, the shielding receptacle 2760 can include enclosed containers 2764 for one or more of the plurality of individual battery cells 2720. In another embodiment, the battery pack housing 2730 or the shielding receptacle 2760 can further comprise: a Kevlar disc to dissipate heat caused by the catastrophic runaway of the one or more of the plurality of individual battery cells 2720; a one-way perforated label to release pressure caused by the catastrophic runaway of the one or more of the plurality of individual battery cells 2720 and repel liquid and dust; and a pressure release valve to release pressure from one or more of the plurality of individual battery cells 2720, wherein the pressure is caused by the catastrophic runaway of the one or more of the plurality of individual battery cells 2720.

In one embodiment, the one-way perforated label or the pressure release valve can be configured to release pressure from the shielding receptacle 2760 or from the inner cavity 2740 of the battery pack housing 2730 when the pressure exceeds a selected threshold. In another embodiment, the battery pack housing 2730 or the shielding receptacle 2760 can further comprise a one-way vent configured to release pressure from the shielding receptacle 2760 or from the inner cavity 2740 of the battery pack housing 2730 when the pressure exceeds a selected threshold. In another embodiment, the battery pack 2710 can further comprise a liquid cooling system to manage: an internal temperature of the battery pack 2710; an internal temperature of the shielding receptacle 2760; a temperature of one or more battery cells of the plurality of individual battery cells 2720; or the power management module 2762. In another embodiment, the battery pack 2710 can further comprise a temperature sensor configured to: monitor an internal temperature of the battery pack 2710, an internal temperature of the shielding receptacle 2760, or a temperature of one or more battery cells of the plurality of individual battery cells 2720; and provide an indication of an increase in the internal temperature of the battery pack 2710, an internal temperature of the shielding receptacle 2760, or a temperature of one or more battery cells of the plurality of individual battery cells 2720 when the increase exceeds a selected threshold.

In another embodiment, the battery pack 2710 can further comprise: a thermal runaway detector to detect a thermal runaway of one or more battery cells of the plurality of individual battery cells 2720; and a current interrupt device (CID), a chemical fuse, or polymeric positive temperature coefficient (PPTC) device to interrupt a current provided to the one or more battery cells of the plurality of individual battery cells 2720. In another embodiment, the battery pack housing 2730 can further comprise a substantially flat surface, wherein: the one or more wireless transfer coils 2780 are attached to the substantially flat surface or integrated into the substantially flat surface; and the substantially flat surface of the battery pack housing 2730 can be configured to abut a substantially flat surface of a wireless transfer station.

In one embodiment, the battery pack 2710 can further comprise an energy module 2790 configured to: wirelessly receive alternating current (AC) energy from the wireless transfer station; convert the AC energy to direct current (DC) energy; and transfer a selected amount of the DC energy to one or more of the plurality of individual battery cells 2720. In another embodiment, the battery pack 2710 can further comprise a power management bay 2792 located within the inner cavity 2740 of the battery pack housing 2730 and at a location separate from the battery pack bay 2750 and comprise a power management module 2762 to regulate energy transferred between one or more of the plurality of individual battery cells 2720 and a wireless transfer station or a device. In another embodiment, the battery pack 2710 can further comprise one or more connecting links between the power management module 2762 and one or more of the plurality of individual battery cells 2720, and wherein the power management module 2762 can be configured to use the one or more connecting links to monitor a charging of the one or more of the plurality of individual battery cells 2720. In one example, the one or more connecting links can be one or more wires or cables.

Figure 28:
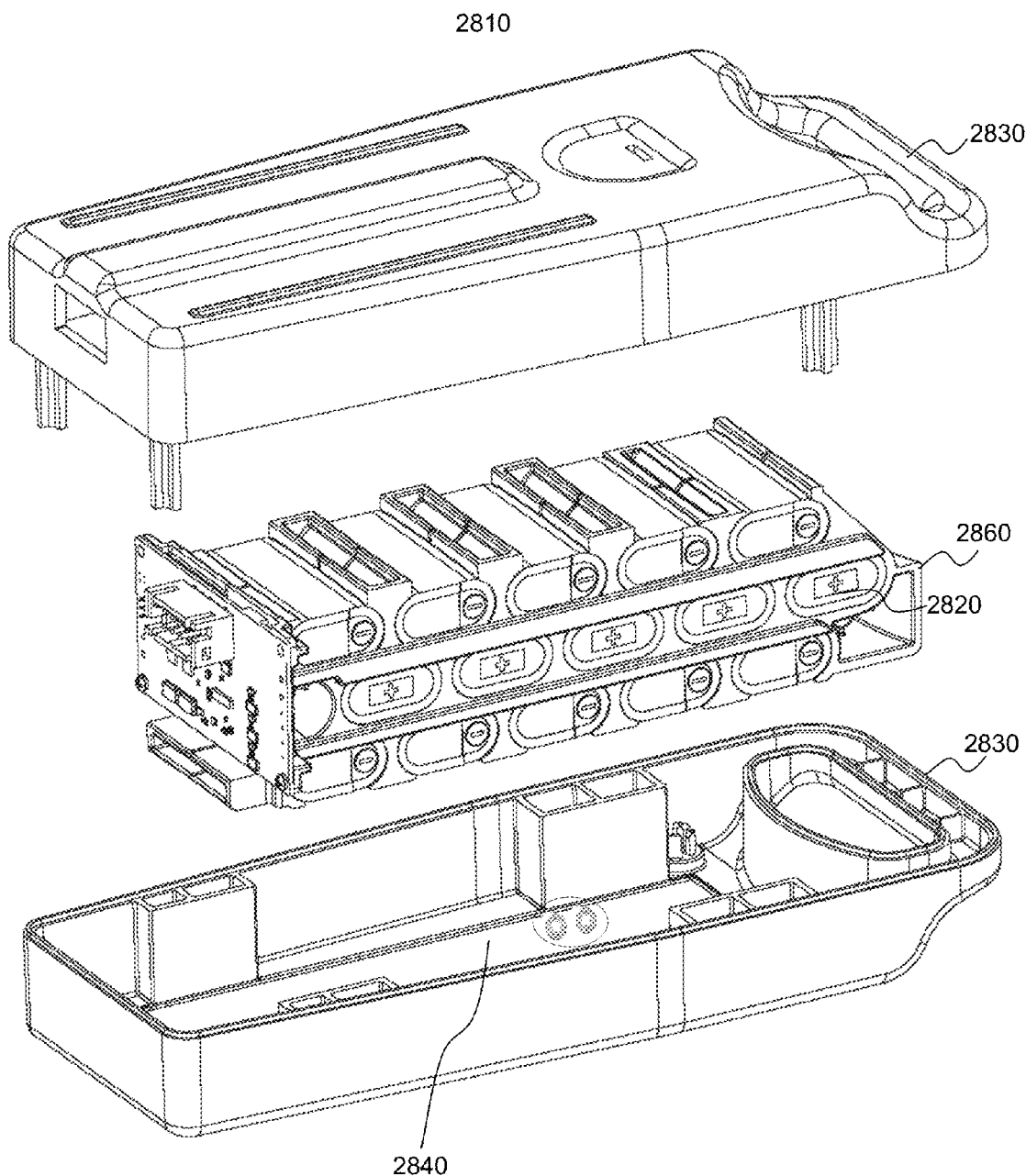
FIG. 28 depicts an exploded view of a battery pack for one or more rechargeable batteries in accordance with an example.

FIG. 28 shows an exploded view of a battery pack 2810 for one or more rechargeable batteries 2820. In one embodiment, the battery pack 2810 can include: a battery pack housing 2830 with an inner cavity 2840; and a battery cell shielding receptacle 2860 located within the inner cavity 2840 of the battery pack housing 2830. In another embodiment the battery cell shielding receptacle 2860 can be sized and shaped to receive a plurality of individual battery cells 2820 and separate each of the plurality of individual battery cells 2820 from adjacent individual battery cells; and comprising a material having a heat deflection rate of greater than 50 degrees Celsius to contain a catastrophic runaway of one or more of the plurality of individual battery cells 2820. In one embodiment, the battery pack housing 2830 can be hermetically sealed to be liquid-proof and dust-proof or sealed to be substantially liquid-proof and dust-proof. In one embodiment, the battery pack housing 2830 can include components in the battery pack housing 2830 that are hermetically sealed to be liquid proof and dust proof or sealed to be substantially liquid proof and dust proof.

In one embodiment, the hermetically sealed battery pack 2810 can further comprise a pressure seal configured to release pressure from the battery pack housing 2830 when the pressure exceeds a selected threshold. In another embodiment, the battery pack housing 2830 or the components in the battery pack housing 2830 are sealed using: an injection material, wherein the injection material is injected into the battery pack housing 2830; or one or more gaskets around one or more seams of the battery pack housing 2830. In another embodiment, the battery pack housing 2830 can further comprise anti-bacterial material to decrease or eliminate a growth or adhesion of pathogens on the battery pack housing 2830. In another embodiment, the anti-bacterial and chemical resistive material can be a polycarbonate plastic with a silver anti-bacterial additive. In another embodiment, the shielding receptacle 2860 can further comprise a cavity or recess configured to receive a portion of one or more battery cells of the plurality of individual battery cells 2820 as the one or more battery cells expand or swell. In another embodiment, the shielding receptacle 2860 can further comprise a flexible material or an expanding material configured to expand as one or more battery cells of the plurality of individual battery cells 2820 expand or swell.

Figure 29:
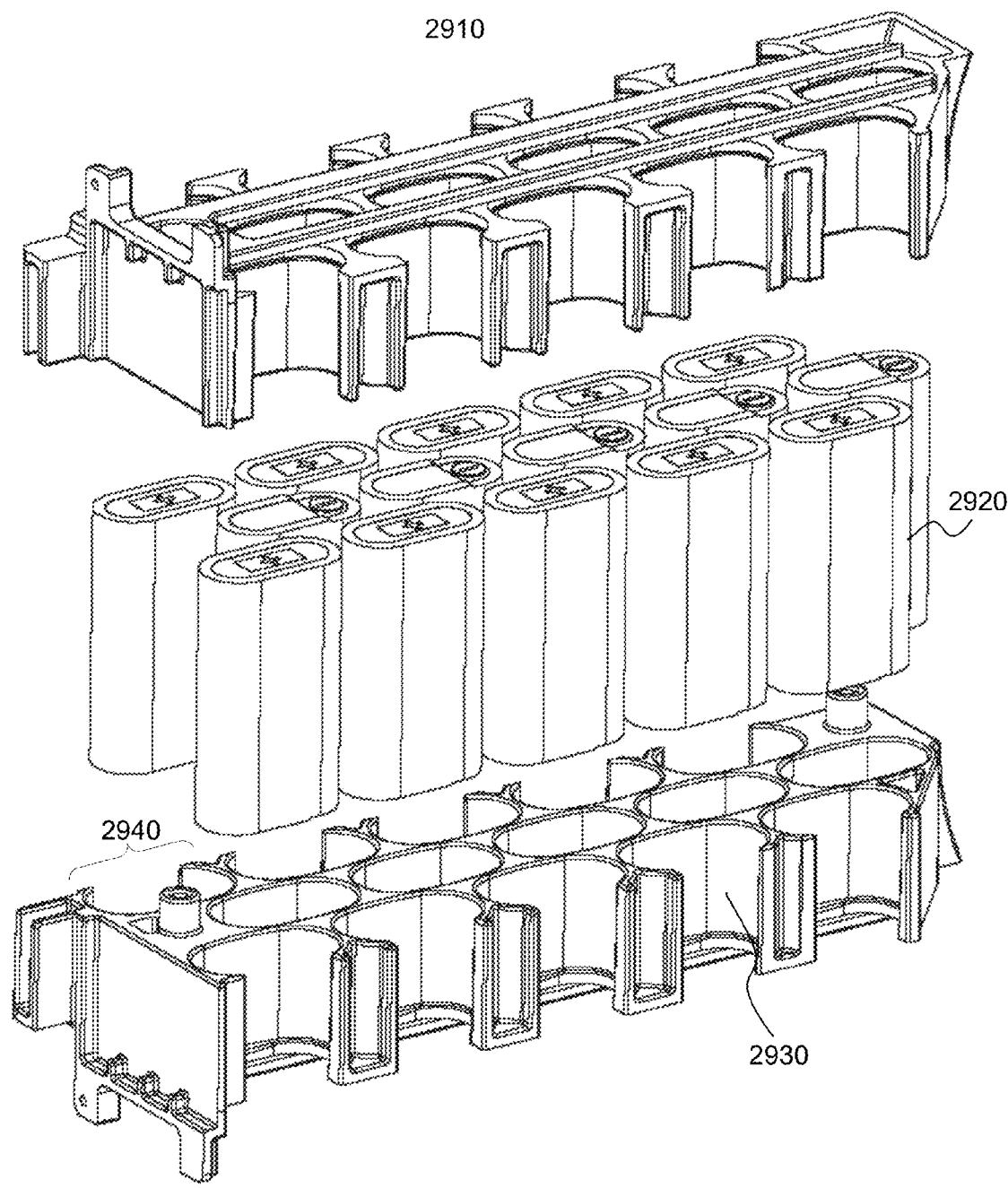
FIG. 29 depicts an exploded view of a thermally shielded receptacle for a rechargeable battery in accordance with an example.

FIG. 29 shows an exploded view of a thermally shielded receptacle 2910 for a rechargeable battery 2920. In one embodiment, the thermally shielded receptacle 2910 can comprise: a material having a heat deflection rate of greater than 50 degrees Celsius to contain a catastrophic runaway of one or more of a plurality of individual battery cells 2920; and the material sized and shaped to receive the plurality of individual battery cells 2920 and separate each of the plurality of individual battery cells 2920 from adjacent individual battery cells.

In one embodiment, the thermally shielded receptacle 2910 can further comprise a layer of heat deflecting material coating an inner surface 2930 of one or more of the shielding receptacles 2940. In another embodiment, the thermally shielded receptacle 2910 can further comprise a thermally conductive material or a phase changing material to absorb heat of greater than 50 degrees Celsius caused by a catastrophic runaway of one or more of the plurality of individual battery cells 2920. In another embodiment, the thermally shielded receptacle 2910 can further comprise a heat shield. In another embodiment, the thermally shielded receptacle 2910 can further comprise a plurality of shielding receptacles 2940 having a honeycomb structure. In another embodiment, a section of the plurality of shielding receptacles 2940 can be offset from another section of the plurality of shielding receptacles 2940 in the honeycomb structure of the thermally shielded receptacle 2910.

Figure 30:
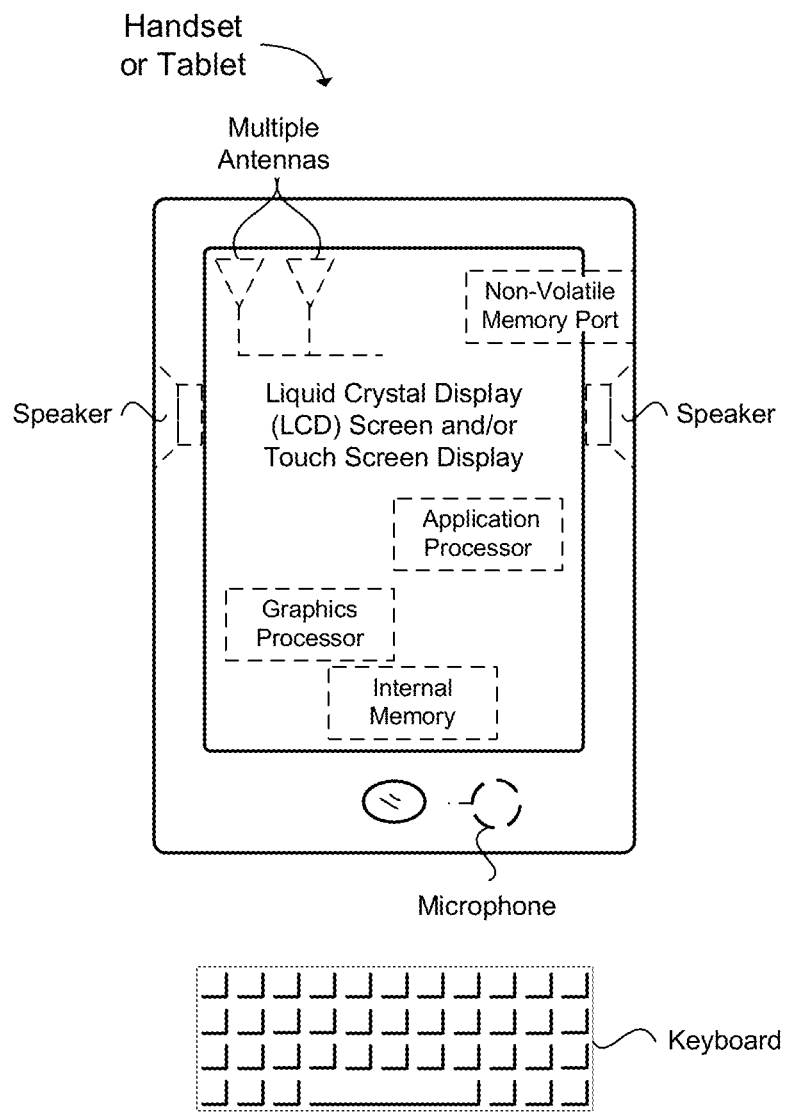
FIG. 30 illustrates a diagram of a device in accordance with an example.

FIG. 30 provides an example illustration of the device, such as a user equipment (UE), a mobile wireless device, a mobile communication device, a tablet, a handset, or other type of wireless device. The wireless device can include one or more antennas configured to communicate with a battery pack. The device can be configured to communicate using at least one wireless communication standard including 3GPP LTE, WiMAX, High Speed Packet Access (HSPA), Bluetooth, and Wi-Fi. The device can communicate using separate antennas for each wireless communication standard or shared antennas for multiple wireless communication standards. The device can communicate in a wireless local area network (WLAN), a wireless personal area network (WPAN), and/or a wireless wide area network (WWAN).

FIG. 30 also provides an illustration of a microphone and one or more speakers that can be used for audio input and output from the device. The display screen can be a liquid crystal display (LCD) screen, or other type of display screen such as an organic light emitting diode (OLED) display. The display screen can be configured as a touch screen. The touch screen can use capacitive, resistive, or another type of touch screen technology. An application processor and a graphics processor can be coupled to internal memory to provide processing and display capabilities. A non-volatile memory port can also be used to provide data input/output options to a user. The non-volatile memory port can also be used to expand the memory capabilities of the device. A keyboard can be integrated with the device or wirelessly connected to the wireless device to provide additional user input. A virtual keyboard can also be provided using the touch screen.

Various techniques, or certain aspects or portions thereof, can take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device can include a processor, a storage medium readable by the processor (including volatile and non-volatile memory and/or storage elements), at least one input device, and at least one output device. The volatile and non-volatile memory and/or storage elements can be a RAM, EPROM, flash drive, optical drive, magnetic hard drive, or other medium for storing electronic data. The base station and mobile station can also include a transceiver module, a counter module, a processing module, and/or a clock module or timer module. One or more programs that can implement or utilize the various techniques described herein can use an application programming interface (API), reusable controls, and the like. Such programs can be implemented in a high level procedural or object oriented programming language to communicate with a computer system. However, the program(s) can be implemented in assembly or machine language, if desired. In any case, the language can be a compiled or interpreted language, and combined with hardware implementations.

It should be understood that many of the functional units described in this specification have been labeled as modules, in order to more particularly emphasize their implementation independence. For example, a module can be implemented as a hardware circuit comprising custom VLSI circuits or gate arrays, off-the-shelf semiconductors such as logic chips, transistors, or other discrete components. A module can also be implemented in programmable hardware devices such as field programmable gate arrays, programmable array logic, programmable logic devices or the like.

Modules can also be implemented in software for execution by various types of processors. An identified module of executable code can, for instance, comprise one or more physical or logical blocks of computer instructions, which can, for instance, be organized as an object, procedure, or function. Nevertheless, the executables of an identified module need not be physically located together, but can comprise disparate instructions stored in different locations which, when joined logically together, comprise the module and achieve the stated purpose for the module.

Indeed, a module of executable code can be a single instruction, or many instructions, and can even be distributed over several different code segments, among different programs, and across several memory devices. Similarly, operational data can be identified and illustrated herein within modules, and can be embodied in any suitable form and organized within any suitable type of data structure. The operational data can be collected as a single data set, or can be distributed over different locations including over different storage devices, and can exist, at least partially, merely as electronic signals on a system or network. The modules can be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention can be referred to herein along with alternatives for the various components thereof. It is understood that such embodiments, examples, and alternatives are not to be construed as defacto equivalents of one another, but are to be considered as separate and autonomous representations of the present invention.

Furthermore, the described features, structures, or characteristics can be combined in any suitable manner in one or more embodiments. In the following description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A battery pack for a battery, the battery pack comprising:
a battery pack housing with an inner cavity;
a battery bay located within the inner cavity;
a shielding receptacle located within the battery bay that is sized and shaped to receive a plurality of individual battery cells and separate each of the plurality of individual battery cells from adjacent individual battery cells, wherein the shielding receptacle consists essentially of a material having a heat deflection rate of greater than 50 degrees Celsius; and
a Kevlar disc located within the inner cavity to dissipate heat caused by a catastrophic runaway of the one or more of the plurality of individual battery cells.

2. The battery pack of claim 1, wherein the battery pack housing or the shielding receptacle further comprises:
a one-way perforated label or a pressure release valve to release pressure caused by the catastrophic runaway of the one or more of the plurality of individual battery cells,
wherein
the one-way perforated label or the pressure release valve is configured to release pressure from the shielding receptacle or from the inner cavity of the battery pack housing when the pressure exceeds a selected threshold.

3. The battery pack of claim 1, further comprising a temperature sensor configured to:
monitor an internal temperature of the battery pack, an internal temperature of the shielding receptacle, or a temperature of one or more battery cells of the plurality of individual battery cells; and
provide an indication of an increase in the internal temperature of the battery pack, an internal temperature of the shielding receptacle, or a temperature of one or more battery cells of the plurality of individual battery cells when the increase exceeds a selected threshold.

4. The battery pack of claim 1, further comprising:
a thermal runaway detector to detect a thermal runaway of one or more battery cells of the plurality of individual battery cells; and
a current interrupt device (CID), a chemical fuse, or polymeric positive temperature coefficient (PPTC) device to interrupt a current provided to the one or more battery cells of the plurality of individual battery cells.

5. A battery pack for a rechargeable battery, comprising:
a battery pack housing with an inner cavity;
a battery cell shielding receptacle located within the inner cavity of the battery pack housing that is sized and shaped to receive a plurality of individual battery cells and separate each of the plurality of individual battery cells from adjacent individual battery cells, the battery cell shielding receptacle comprising a material having a heat deflection rate of greater than 50 degrees Celsius to contain a catastrophic runaway of one or more of the plurality of individual battery cells;

wherein the battery pack housing or components in the battery pack housing are hermetically sealed to be liquid proof and dust proof or sealed to be substantially liquid proof and dust proof; and wherein the hermetically sealed battery pack further comprises a pressure seal configured to release pressure from the battery pack housing when the pressure exceeds a selected threshold.

6. The battery pack of claim 5, wherein the battery pack housing is comprised of an anti-bacterial material to decrease or eliminate a growth or adhesion of pathogens on the battery pack housing.

7. The battery pack of claim 6, wherein the anti-bacterial material is chemically resistant.

8. The battery pack of claim 5, wherein the battery cell shielding receptacle further comprises a swelling cavity or recess configured to receive a portion of one or more battery cells of the plurality of individual battery cells as the one or more battery cells expand or swell.

9. The battery pack of claim 5, wherein the battery cell shielding receptacle further comprises a flexible material configured to expand as one or more battery cells of the plurality of individual battery cells expands or swells.

10. A thermally shielded receptacle for a rechargeable battery, the thermally shielded receptacle comprising:

a material having a heat deflection rate of greater than 50 degrees Celsius to contain a catastrophic runaway of one or more of a plurality of individual battery cells; wherein the thermally shielded receptacle is sized and shaped to receive the plurality of individual battery cells and separate each of the plurality of individual battery cells from adjacent individual battery cells, and the thermally shielded receptacle includes a cavity or recess configured to receive a portion of one or more battery cells of the plurality of individual battery cells as the one or more battery cells expand or swell.

11. A thermally shielded receptacle for a rechargeable battery, the thermally shielded receptacle comprising:

a material having a heat deflection rate of greater than 50 degrees Celsius to contain a catastrophic runaway of one or more of a plurality of individual battery cells, the material being flexible and configured to expand as one or more battery cells of the plurality of individual battery cells expands or swells; wherein the thermally shielded receptacle is sized and shaped to receive the plurality of individual battery cells and separate each of the plurality of individual battery cells from adjacent individual battery cells.

12. The battery pack of claim 1, wherein the battery pack housing is comprised of an anti-bacterial material to decrease or eliminate a growth or adhesion of pathogens on the battery pack housing.

13. The battery pack of claim 12, wherein the anti-bacterial material is chemically resistant.

14. The battery pack of claim 13, wherein the anti-bacterial material is a polycarbonate plastic with a silver anti-bacterial additive.

15. The battery pack of claim 7, wherein the anti-bacterial material is a polycarbonate plastic with a silver anti-bacterial additive.

16. A shielding receptacle for use with a plurality of battery cells, comprising:

a first shielding receptacle section that includes a plurality of first cell pockets that open towards a first face of the first shielding receptacle section; and a second shielding receptacle section that includes a plurality of second cell pockets that open towards a second face of the second shielding receptacle section, each of the plurality of second cell pockets corresponding to one of the plurality of first cell pockets; wherein each of the plurality of first cell pockets and corresponding one of the plurality of second cell pockets define a shielding compartment configured to receive a battery cell when the first face of the first shielding receptacle section is coupled to the second face of the second shielding receptacle section.

17. The apparatus of claim 16, wherein;

the plurality of first cell pockets are aligned in a plurality of rows wherein adjacent rows of the plurality of first cell pockets are aligned such that the plurality of first cell pockets in adjacent rows are offset from each other; and the plurality of second cell pockets are aligned in a plurality of rows wherein adjacent rows of the plurality of second cell pockets are aligned such that the plurality of second cell pockets in adjacent rows are offset from each other.

\* \* \* \* \*